US011564892B2

(12) United States Patent
Niemelä

(10) Patent No.: US 11,564,892 B2
(45) Date of Patent: *Jan. 31, 2023

(54) VIRUS-LIKE PARTICLES FOR PREVENTING THE SPREADING AND LOWERING THE INFECTION RATE OF VIRUSES

(71) Applicant: Finncure Oy, Helsinki (FI)

(72) Inventor: Erik Johan Niemelä, Helsinki (FI)

(73) Assignee: FinnCure Oy, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/684,341

(22) Filed: Mar. 1, 2022

(65) Prior Publication Data

US 2022/0273581 A1   Sep. 1, 2022

Related U.S. Application Data

(63) Continuation-in-part of application No. PCT/FI2021/050259, filed on Apr. 9, 2021.

(30) Foreign Application Priority Data

Apr. 9, 2020  (FI) ...................................... 20205382
Feb. 19, 2021 (FI) ...................................... 20215182

(51) Int. Cl.

| | | |
|---|---|---|
| C07K 16/10 | (2006.01) | |
| C07K 16/28 | (2006.01) | |
| C07K 16/08 | (2006.01) | |
| A61K 39/42 | (2006.01) | |
| A61K 39/215 | (2006.01) | |
| A61K 9/51 | (2006.01) | |
| A61K 9/00 | (2006.01) | |
| A61K 9/50 | (2006.01) | |
| A61K 31/7105 | (2006.01) | |
| A61K 31/711 | (2006.01) | |
| A61K 39/145 | (2006.01) | |
| C07K 14/08 | (2006.01) | |
| C07K 17/00 | (2006.01) | |
| C07K 17/02 | (2006.01) | |
| C07K 17/14 | (2006.01) | |
| A61K 31/56 | (2006.01) | |
| A61K 33/30 | (2006.01) | |
| A61K 9/16 | (2006.01) | |
| A61K 47/69 | (2017.01) | |
| A61K 47/62 | (2017.01) | |
| A61K 39/00 | (2006.01) | |

(52) U.S. Cl.
CPC ............ *A61K 9/5184* (2013.01); *A61K 9/007* (2013.01); *A61K 9/167* (2013.01); *A61K 9/5078* (2013.01); *A61K 9/5089* (2013.01); *A61K 9/51* (2013.01); *A61K 9/5192* (2013.01); *A61K 31/56* (2013.01); *A61K 31/711* (2013.01); *A61K 31/7105* (2013.01); *A61K 33/30* (2013.01); *A61K 39/145* (2013.01); *A61K 39/215* (2013.01); *A61K 47/62* (2017.08); *A61K 47/6929* (2017.08); *C07K 14/08* (2013.01); *C07K 17/00* (2013.01); *C07K 17/02* (2013.01); *C07K 17/14* (2013.01); *A61K 2039/544* (2013.01); *A61K 2039/6093* (2013.01)

(58) Field of Classification Search
CPC .... A61K 9/5184; A61K 9/007; A61K 39/215; C07K 16/10; C12N 2710/12034; C12N 2740/15051; C12N 7/00
See application file for complete search history.

(56) References Cited

U.S. PATENT DOCUMENTS

| | | |
|---|---|---|
| 6,146,632 A | 11/2000 | Momin et al. |
| 6,372,227 B1 | 4/2002 | Garcon et al. |
| 6,544,518 B1 | 4/2003 | Friede et al. |
| 8,058,069 B2 | 11/2011 | Yaworski et al. |
| 8,278,036 B2 | 10/2012 | Kariko et al. |
| 8,691,966 B2 | 4/2014 | Kariko et al. |
| 8,748,089 B2 | 6/2014 | Kariko et al. |
| 8,835,108 B2 | 9/2014 | Kariko et al. |
| 9,012,219 B2 | 4/2015 | Kariko et al. |

(Continued)

FOREIGN PATENT DOCUMENTS

| | | |
|---|---|---|
| WO | WO 86/07540 | 12/1986 |
| WO | WO 2005/020885 | 3/2005 |

(Continued)

OTHER PUBLICATIONS

Chen et al., "Emerging coronaviruses: Genome structure, replication, and pathogenesis", Journal of Medical Virology, pp. 418-423, vol. 92 (2020).

(Continued)

*Primary Examiner* — Barry A Chestnut
(74) *Attorney, Agent, or Firm* — Knobbe, Martens, Olson & Bear, LLP

(57) ABSTRACT

According to some embodiments, a carrier for reducing a likelihood of a pathogen binding to cell structures of a host comprises a core, surface features extending from an exterior surface of the core, wherein the surface features are configured to bind to target areas of cell structures of the host to at least partially block the pathogen from binding to said target areas as a result of competitive inhibition, and a plurality of binding sites along the exterior surface, wherein the binding sites are configured to attract at least one portion of the pathogen, wherein the binding sites are recognizable by the pathogen and are able to be bound by the pathogen, thereby at least partially immobilizing the pathogen and reducing the likelihood of the pathogen binding to target areas of cell structures of the host.

20 Claims, 7 Drawing Sheets

Specification includes a Sequence Listing.

(56) References Cited

U.S. PATENT DOCUMENTS

| | | |
|---|---|---|
| 9,139,554 B2 | 9/2015 | Hope et al. |
| 9,163,213 B2 | 10/2015 | Kariko et al. |
| 9,364,435 B2 | 6/2016 | Yaworski et al. |
| 9,371,511 B2 | 6/2016 | Kariko et al. |
| 9,404,127 B2 | 8/2016 | Yaworski et al. |
| 9,518,272 B2 | 12/2016 | Yaworski et al. |
| 9,567,296 B2 | 2/2017 | Payne et al. |
| 9,580,711 B2 | 2/2017 | Payne et al. |
| 9,669,089 B2 | 6/2017 | Thess et al. |
| 9,750,824 B2 | 9/2017 | Kariko et al. |
| 9,758,795 B2 | 9/2017 | Cullis et al. |
| 9,814,777 B2 | 11/2017 | Manoharan et al. |
| 9,868,692 B2 | 1/2018 | Benenato |
| 9,943,846 B2 | 4/2018 | Cullis et al. |
| 9,950,065 B2 | 4/2018 | Sahin et al. |
| 10,006,007 B2 | 6/2018 | Kariko et al. |
| 10,041,091 B2 | 8/2018 | Cullis et al. |
| 10,064,959 B2 | 9/2018 | Schrum et al. |
| 10,159,652 B2 | 12/2018 | Walsh et al. |
| 10,166,298 B2 | 1/2019 | Ansell et al. |
| 10,221,127 B2 | 3/2019 | Du et al. |
| 10,227,302 B2 | 3/2019 | Payne et al. |
| 10,232,055 B2 | 3/2019 | Kariko et al. |
| 10,233,148 B2 | 3/2019 | Payne et al. |
| 10,266,485 B2 | 4/2019 | Benenato |
| 10,442,756 B2 | 10/2019 | Benenato et al. |
| 10,485,884 B2 | 11/2019 | Sahin et al. |
| 10,576,146 B2 | 3/2020 | Sahin et al. |
| 10,577,403 B2 | 3/2020 | De Fougerolles et al. |
| 10,653,780 B2 | 5/2020 | Hope et al. |
| 10,702,600 B1 | 7/2020 | Ciaramella et al. |
| 10,703,789 B2 | 7/2020 | De Fougerolles et al. |
| 10,780,054 B2 | 9/2020 | Ketterer et al. |
| 10,799,602 B2 | 10/2020 | Baumhof |
| 10,815,463 B2 | 10/2020 | Chivukula et al. |
| 2005/0130127 A1 | 6/2005 | Rottier et al. |
| 2007/0141078 A1 | 6/2007 | D'Hondt et al. |
| 2014/0030808 A1 | 1/2014 | Sahin et al. |
| 2017/0273907 A1 | 9/2017 | Haas et al. |
| 2018/0185516 A1 | 7/2018 | Ansell et al. |
| 2018/0237602 A1 | 8/2018 | Ihalainen et al. |
| 2018/0263907 A1 | 9/2018 | Hefesha et al. |
| 2018/0296663 A1 | 10/2018 | Hipp et al. |
| 2018/0303925 A1 | 10/2018 | Weissman et al. |
| 2019/0002179 A1 | 1/2019 | Rosqvist et al. |
| 2019/0015501 A1 | 1/2019 | Ciaramella et al. |
| 2019/0022247 A1 | 1/2019 | Ansell et al. |
| 2019/0032087 A1 | 1/2019 | Cullis et al. |
| 2019/0083602 A1 | 3/2019 | Roos et al. |
| 2019/0153428 A1 | 5/2019 | Kariko et al. |
| 2019/0274968 A1 | 9/2019 | Weissman et al. |
| 2019/0314496 A1 | 10/2019 | Fotin-Mleczek et al. |
| 2019/0321458 A1 | 10/2019 | Sahin et al. |
| 2019/0336608 A1 | 11/2019 | Baumhof et al. |
| 2019/0351048 A1 | 11/2019 | Rauch |
| 2020/0015567 A1 | 1/2020 | Lau |
| 2020/0046830 A1 | 2/2020 | Hooper et al. |
| 2020/0046838 A1 | 2/2020 | Ansell et al. |
| 2020/0085852 A1 | 3/2020 | Fotin-Mleczek |
| 2020/0109113 A1 | 4/2020 | Payne et al. |
| 2020/0163878 A1 | 5/2020 | Baumhof et al. |
| 2020/0164038 A1 | 5/2020 | De Fougerolles et al. |
| 2020/0172472 A1 | 6/2020 | Du |
| 2020/0179526 A1 | 6/2020 | Baumhof et al. |
| 2020/0197508 A1 | 6/2020 | Bihi et al. |
| 2020/0206362 A1 | 7/2020 | Besin et al. |
| 2020/0246451 A1 | 8/2020 | Mutzke et al. |
| 2020/0283372 A1 | 9/2020 | Du |
| 2020/0297634 A1 | 9/2020 | Karmali et al. |
| 2020/0345831 A1 | 11/2020 | Thess et al. |
| 2021/0113681 A1 | 4/2021 | Nabel et al. |
| 2022/0280439 A1 | 9/2022 | Niemelä |
| 2022/0280635 A1 | 9/2022 | Niemelä |

FOREIGN PATENT DOCUMENTS

| | | |
|---|---|---|
| WO | WO 2008/150276 | 12/2008 |
| WO | WO 2008/154603 | 12/2008 |
| WO | WO 2009/086558 | 7/2009 |
| WO | WO 2010/085509 | 7/2010 |
| WO | WO 2011/036557 | 3/2011 |
| WO | WO 2013/059922 | 5/2013 |
| WO | WO 2013/087083 | 6/2013 |
| WO | WO 2014/153087 | 9/2014 |
| WO | WO 2015/043613 | 4/2015 |
| WO | WO 2015/054639 | 4/2015 |
| WO | WO 2015/164674 | 10/2015 |
| WO | WO 2016/118724 | 7/2016 |
| WO | WO 2016/118725 | 7/2016 |
| WO | WO 2016/156398 | 10/2016 |
| WO | WO 2017/009533 | 1/2017 |
| WO | WO 2017/070626 | 4/2017 |
| WO | WO 2017/165506 | 9/2017 |
| WO | WO 2019/241483 | 12/2019 |
| WO | WO 2020/002598 | 1/2020 |
| WO | WO 2020/012060 | 1/2020 |
| WO | WO 2020/097540 | 5/2020 |
| WO | WO 2020/097548 | 5/2020 |
| WO | WO 2021/089922 | 5/2021 |
| WO | WO 2021/142516 | 7/2021 |
| WO | WO 2021/205077 | 10/2021 |
| WO | WO 2021/205079 | 10/2021 |
| WO | WO 2021/206638 | 10/2021 |
| WO | WO 2021/209992 | 10/2021 |

OTHER PUBLICATIONS

Galvao et al., "Unexpected low-dose toxicity of the universal solvent DMSO", The FASEB Journal, pp. 1317-1330, vol. 28, Issue 3 (Mar. 2014).

International Search Report and Written Opinion issued in PCT/FI2021/050259 dated Jul. 2, 2021.

International Search Report and Written Opinion issued in PCT/FI2021/050261 dated Jul. 22, 2021.

Abagnale et al., "Surface topography enhances differentiation of mesenchymal stem cells towards osteogenic and adipogenic lineages", Biomaterials, pp. 316-326, vol. 61 (Aug. 2015).

Abagnale et al., "Surface Topography Guides Morphology and Spatial Patterning of Induced Pluripotent Stem Cell Colonies", Stem Cell Reports, pp. 654-666, vol. 9, Issue 2 (Aug. 8, 2017).

Abbott et al., "Metrics: Do metrics matter?", Nature, pp. 860-862, vol. 465 (Jun. 16, 2010).

Abo-Zeid et al., "An investigation of rhinovirus infection on cellular uptake of poly (glycerol-adipate) nanoparticles", International Journal of Pharmaceutics, pp. 1-10, vol. 589 (Nov. 15, 2020).

Achterberg et al., "The Nano-Scale Mechanical Properties of the Extracellular Matrix Regulate Dermal Fibroblast Function", Journal of Investigative Dermatology, pp. 1862-1872, vol. 134, Issue 7 (Jul. 1, 2014).

Adachi et al., "Heat shock proteins in neurodegenerative diseases: Pathogenic roles and therapeutic implications", International Journal of Hypothermia, pp. 647-654, vol. 25, Issue 8 (2009).

Adamo et al., "A Roadmap for Academic Health Centers to Establish Good Laboratory Practice-Compliant Infrastructure", Academic Medicine, pp. 279-284, vol. 87, No. 3 (Mar. 2012).

Afkhami et al., "Respiratory mucosal delivery of next-generation COVID-19 vaccine provides robust protection against both ancestral and variant strains of SARS-CoV-2", Cell, pp. 896-915, vol. 185, Issue 5 (Mar. 3, 2022).

Aggarwal, "Signalling pathways of the TNF superfamily: A double-edged sword", Nature Reviews Immunology, pp. 745-756, vol. 3 (Sep. 1, 2003).

Ahmed et al., "Detection of SARS-CoV-2 RNA in commercial passenger aircraft and cruise ship wastewater: a surveillance tool for assessing the presence of COVID-19 infected travellers", Journal of Travel Medicine, pp. 1-11, vol. 27, Issue 6 (2020).

Ahmed et al., "Preliminary Identification of Potential Vaccine Targets for the COVID-19 Coronavirus (SARS-CoV-2) Based on SARS-CoV Immunological Studies", Viruses, 12(3):254 (Feb. 25, 2020).

(56) References Cited

OTHER PUBLICATIONS

Åkerfelt et al., "Heat shock factors: integrators of cell stress, development and lifespan", Nature Reviews Molecular Cell Biology, pp. 1-25, vol. 11, Issue 8 (Aug. 2010).
Akram, "Inanimate surfaces as potential source of 2019-nCoV spread and their disinfection with biocidal agents", Virusdisease, pp. 94-96, vol. 31, Issue 2 (Apr.-Jun. 2020).
Al Awaidy et al., "Middle East Respiratory Syndrome Coronavirus (Mers-cov) in Oman: Current Situation and Going Forward", Oman Medical Journal, pp. 181-183, vol. 34, No. 3 (2019).
Alastalo et al., "Formation of nuclear stress granules involves HSF2 and coincides with the nucleolar localization of Hsp70", Journal of Cell Science, pp. 3557-3570, vol. 116, Issue 17 (2003).
Albanese et al., "The effect of nanoparticle size, shape, and surface chemistry on biological systems", Annual Review of Biomedical Engineering, pp. 1-16, vol. 14 (2012).
Albini et al., "The SARS-CoV-2 receptor, ACE-2, is expressed on many different cell types: implications for ACE-inhibitor- and angiotensin II receptor blocker-based cardiovascular therapies", Internal and Emergency Medicine, pp. 759-766, vol. 15 (2020).
Alharbi et al., "Assessment of the bacterial contamination of hand air dryer in washrooms", Saudi Journal of Biological Sciences, pp. 268-271, vol. 23 (2016).
Ali et al., "Industrial perspective in ocular drug delivery", Advanced Drug Delivery Reviews, pp. 1258-1268, vol. 58, Issue 11 (Nov. 15, 2006).
Alila et al., "Controlled surface modification of cellulose fibers by amino derivatives using N,N'-carbonyldiimidazole as activator", Carbohydrate Polymers, pp. 553-562, vol. 77, Issue 3 (2009).
Allan et al., "Mechanisms of therapy-related carcinogenesis", Nature Reviews Cancer, pp. 943-955, vol. 5 (Nov. 18, 2005).
Alnaqbi et al., "HLA repertoire of 115 UAE nationals infected with SARS-CoV-2", Human Immunology,, pp. 1-9, vol. 83, Issue 1 (Jan. 2022 ).
Alphandéry, "The Potential of Various Nanotechnologies for Coronavirus Diagnosis/Treatment Highlighted through a Literature Analysis", Bioconjugate Chemistry, pp. 1873-1882, vol. 31 (2020).
Altankov et al., "The role of surface zeta potential and substratum chemistry for regulation of dermal fibroblasts interaction", Materials Science & Engineering Technology, pp. 1120-1128, vol. 34, Issue 12 (Dec. 2003).
Amidon et al., "A theoretical basis for a biopharmaceutic drug classification: the correlation of in vitro drug product dissolution and in vivo bioavailability", The AAPS Journal, pp. 894-898, vol. 16 (2014).
Amrhein et al., "Scientists rise up against statistical significance", Nature, Comments, pp. 305-307, vol. 567 (Mar. 21, 2019).
Anand et al., "Cancer is a Preventable Disease that Requires Major Lifestyle Changes", Pharmaceutical Research, pp. 2097-2116, vol. 25, No. 9 (Sep. 2008).
Ananthakrishnan et al., "The Forces Behind Cell Movement", International Journal of Biological Sciences, pp. 303-317, vol. 3, Issue 5 (2007).
Anderson et al., "A framework for the development of effective anti-metastatic agents", Nature Reviews | Clinical Oncology, pp. 185-204, vol. 16 (Mar. 2019).
Andersson et al., "Influences of Material Characteristics on Ibuprofen Drug Loading and Release Profiles from Ordered Micro- and Mesoporous Silica Matrices", Chemistry of Materials, pp. 4160-4167, vol. 16, Issue 21 (Oct. 19, 2004).
Anft et al., "COVID-19 progression is potentially driven by T cell immunopathogenesis", medRxiv 2020.04.28.20083089; doi: https://doi.org/10.1101/2020.04.28.20083089.
Angelova et al., "Rationalizing the design of polymeric biomaterials", Trends in Biotechnology, pp. 409-421, vol. 17, Issue 10 (Oct. 1, 1999).
Angsantikul et al., "Coating nanoparticles with gastric epithelial cell membrane for targeted antibiotic delivery against Helicobater pylori infection", Advanced Therapeutics, 1800016, in 20 pages, vol. 1 (Jun. 2018).
Arduino et al., "Preparation of cetyl palmitate-based PEGylated solid lipid nanoparticles by microfluidic technique", Acta Biomaterialia, pp. 566-578, vol. 121 (Feb. 2021).
Argyo et al., "Multifunctional Mesoporous Silica Nanoparticles as a Universal Platform for Drug Delivery", Chemistry of Materials, pp. 435-451, vol. 26, Issue 1 (2014).
Armstrong et al., "Transepithelial Invasion and Intramesenchymal Infiltration of the Chick Embryo Chorioallantois by Tumor Cell Lines", Cancer Research, pp. 1826-1837, vol. 42 (May 1982).
Arruebo et al., "Assessment of the Evolution of Cancer Treatment Therapies", Cancers, pp. 3279-3330, vol. 3 (2011).
Arts et al., "BCG Vaccination Protects against Experimental Viral Infection in Humans through the Induction of Cytokines Associated with Trained Immunity", Cell Host & Microbe, pp. 89-100, vol. 23, Issue 1 (Jan. 10, 2018).
Atanasov et al., "Discovery and resupply of pharmacologically active plant-derived natural products: A review", Biotechnology Advances, pp. 1582-1614, vol. 33, Issue 8 (Dec. 2015).
Attarwala, "Role of antibodies in cancer targeting", Journal of Natural Science, Biology and Medicine, pp. 53-56, vol. 1, Issue 1 (Jul. 2010).
Awoniyi, "The Petri-Dish Effect", Disaster Medicine and Public Health Preparedness, pp. e1-e2, vol. 14, Issue 3 (Jun. 2020).
A'Yun et al., "Dry heat induced whey protein-lactose conjugates largely improve the heat stability of O/W emulsions", International Dairy Journal, vol. 108, 2020, 104736.
Bae et al., "Targeted drug delivery to tumors: Myths, reality and possibility", Journal of Controlled Release, pp. 198-205, vol. 153, Issue 3 (Aug. 10, 2011).
Baer et al., "Provenance information as a tool for addressing engineered nanoparticle reproducibility challenges", Biointerphases, 04B401, vol. 11 (2016).
Baer, "Guide to Making XPS Measurements on nanparticles", Journal of Vacuum Science & Technology A, 031201, vol. 38 (2020).
Baer, "The Chameleon Effect: Characterization Challenges Due to the Variability of Nanoparticles and Their Surfaces", Frontiers in Chemistry, Article 145, pp. 1-7, vol. 6 (May 2018).
Bagnoli et al., "Cellular FLICE-inhibitory protein (c-FLIP) signalling: A key regulator of receptor-mediated apoptosis in physiologic context and in cancer", The International Journal of Biochemistry & Cell Biology, pp. 210-213, vol. 42, Issue 2 (Feb. 2010).
Baker et al., "ChAdOx1 interacts with CAR and PF4 with implications for thrombosis with thrombocytopenia syndrome", Sciience Advances | Research Article, pp. 1-14, vol. 7, Issue 49 (Dec. 1, 2021).
Bali et al., "An overview of gene therapy in head and neck cancer", Indian Journal of Human Genetics, pp. 282-290, vol. 19, Issue 3 (Jul.-Sep. 2013).
Ballabh et al., "The blood-brain barrier: an overview: structure, regulation, and clinical implication", Neurobiology of Disease, pp. 1-13, vol. 16, Issue 1 (Jun. 2004).
Baltazar et al., "Acidic Nanoparticles Are Trafficked to Lysosomes and Restore an Acidic Lysosomal pH and Degradative Function to Compromised ARPE-19 Cells", PLOS | ONE, pp. 1-10, vol. 7, Issue 12 (Dec. 2012).
Banerjee et al., "Hypothesis testing, type I and type II errors", Industrial Psychiatry Journal, pp. 127-131, vol. 18, Issue 2 (Jul.-Dec. 2009).
Barenholz, "Doxil®—The First FDA-approved nano-drug: Lessons learned", Journal of Controlled Release, pp. 117-134, vol. 160, Issue 2 (Jun. 10, 2012).
Barker et al., "Bioinformatic characterization of angiotensin-converting enzyme 2, the entry receptor for SARS-CoV2", PLoS One, in 29 pages, 15(10), e0240647 (2020).
Baron et al., "Amyotrophic lateral sclerosis-linked FUS/TLS alters stress granule assembly and dynamics", Molecular Neurodegeneration, pp. 1-18, vol. 8, Article No. 30, Research Article | Open Access, (Published Aug. 31, 2013).
Bartrip, "History of asbestos related disease", Postgraduate Medical Journal, pp. 72-76, vol. 80(940) (Feb. 2004).

(56) References Cited

OTHER PUBLICATIONS

Barua et al., "Challenges associated with Penetration of Nanoparticles across Cell and Tissue Barriers: A Review of Current Status and Future Prospects", Nano Today, pp. 223-243, vol. 9, Issue 2 (Apr. 1, 2014).
Bastard et al., "Autoantibodies against type I IFNs in patients with life-threatening COVID-19", Science, pp. 1-17, vol. 370, No. 6515 (Sep. 24, 2020).
Batista et al., "Minimizing disease spread on a quarantined cruise ship: A model of COVID-19 with asymptomatic infections", Mathematical Biosciences, pp. 1-11, vol. 329 (Nov. 2020, 108442).
Batlle et al., "Soluble angiotensin-converting enzyme 2: a potential approach for coronavirus infection therapy?", Clinical Science (London), pp. 543-545, vol. 134, No. 5 (Mar. 13, 2020).
Bazak et al., "Passive targeting of nanoparticles to cancer: A comprehensive review of the literature", Molecular and Clinical Oncology, pp. 904-908, vol. 2, Issue 6 (Nov.-Dec. 2014).
Bean et al., Treatment with ACE-inhibitors is associated with less severe disease with SARS-Covid-19 infection in a multi-site UK acute Hospital Trust, medRxiv 2020.04.07.20056788; doi: https://doi.org/10.1101/2020.04.07.20056788 (2020).
Beck et al., "A New Family of Mesoporous Molecular Sieves Prepared with Liquid Crystal Templates", Journal of the American Chemical Society, pp. 10834-10843, vol. 114 (1992).
Benet, "The Role of BCS (Biopharmaceutics Classification System) and BDDCS (Biopharmaceutics Drug Disposition Classification System) in Drug Development", Journal of Pharmaceutical Sciences, pp. 34-42, vol. 102, Issue 1 (Jan. 2013).
Berbekova et al., "A thematic analysis of crisis management in tourism: A theoretical perspective", Tourism Management, pp. 104342, vol. 86 (2021).
Bergelin et al., "S1P1 and VEGFR-2 form a signaling complex with extracellularly regulated kinase 1/2 and protein kinase C-alpha regulating ML-1 thyroid carcinoma cell migration", Endocrinology, pp. 2994-3005, vol. 151, Issue 7 (Jul. 1, 2010).
Bergman et al., "On the Complexity of Electrostatic Suspension Stabilization of Functionalized Silica Nanoparticles for Biotargeting and Imaging Applications", Journal of Nanomaterials, in 9 pages, vol. 2008, Research Article | Open Access, Article ID 712514, https://doi.org/10.1155/2008/712514 (Apr. 2008).
Bergwerk et al., "Covid-19 Breakthrough Infections in Vaccinated Health Care Workers", The New England Journal of Medicine, pp. 1474-1484, vol. 385 (Oct. 14, 2021).
Bert et al., "Norovirus outbreaks on commercial cruise ships: A systematic review and new targets for the public health agenda", Food and Environmental Virology, pp. 67-74, vol. 6 (2014).
Bettencourt et al., "Identification of antigens presented by MHC for vaccines against tuberculosis", npj Vaccines, in 14 pages, vol. 5, Article No. 2 (2020).
Beutler, "Natural Products as a Foundation for Drug Discovery", Current Protocols in Pharmacology, pp. 1-9, vol. 46, Issue 9 (2009).
Bhakta-Guha et al., "Hormesis: Decoding Two Sides of the Same Coin", Pharmaceuticals (Basel), pp. 865-883, vol. 8 (2015).
Bharti et al., "Mesoporous silica nanoparticles in target drug delivery system: A review", International Journal of Pharmaceutical Investigation, pp. 124-133, vol. 5, No. 3 (Jul. 2015).
Biamonti et al., "Nuclear stress bodies", Cold Spring Harbor Perspectives in Biology, pp. 1-12, vol. 2, Issue 6 (Jun. 2010).
Blanco-Melo et al., "Imbalanced Host Response to SARS-CoV-2 Drives Development of COVID-19", Cell, pp. 1036-1045, vol. 181, Issue 5 (May 28, 2020).
Blum et al., "Pathways of Antigen Processing", Annual Review of Immunology, pp. 443-473, vol. 31 (2013).
Blumenfeld, "Chemotherapy and fertility", Best Practice & Research Clinical Obstetrics & Gynaecology, pp. 379-390, vol. 26, Issue 3 (Jun. 2012).
Boatright et al., "A unified model for apical caspase activation", Molecular Cell, pp. 529-541, vol. 11, Issue 2 (Feb. 1, 2003).
Bobo et al., "Nanoparticle-Based Medicines: A Review of FDA-Approved Materials and Clinical Trials to Date", Pharmaceutical Research, pp. 2373-2387, vol. 33 (2016).
Bojkova et al., "Proteomics of SARS-CoV-2-infected host cells reveals therapy targets", Nature, pp. 469-472, vol. 583 (Jul. 16, 2020).
Bollström et al., "Measuring solvent barrier properties of paper", Measurement Science and Technology, vol. 23, No. 1 (2012).
Bondarenko et al., "Toxicity of Ag, CuO and ZnO nanoparticles to selected environmentally relevant test organisms and mammalian cells in vitro: a critical review", Archives of Toxicology, pp. 1181-1200, vol. 87 (2013).
Boretti et al., "Zinc role in Covid-19 disease and prevention", Vacunas, doi: 10.1016/j.vacun.2021.08.003. (Available online Sep. 7, 2021.
Borzenkov et al., "Fabrication of Inkjet-Printed Gold Nanostars Patterns with Photothermal Properties on Paper Substrate", ACS Applied Materials & Interfaces, pp. 9909-9916, vol. 8 (Mar. 31, 2016).
Borzenkov et al., "Photothermal effect of gold nanostars patterns inkjet-printed on coated paper substrates with different permeability", Beilstein Journal of Nanotechnology, pp. 1480-1485, vol. 7 (2016).
Bowen, "Particle Size Distribution Measurement from Millimeters to Nanometers and from Rods to Platelets", Journal of Dispersion Science and Technology, pp. 631-662, vol. 23, No. 5 (Jan. 1, 2022).
Boyle et al., "Major histocompatibility complex class I-restricted alloreactive CD4 + T cells", Immunology, pp. 54-63, vol. 112, Issue 1 (2004).
Brandenburg et al., "G protein variation in respiratory syncytial virus group A does not correlate with clinical severity", Journal of Clinical Microbiology, pp. 3849-3852, vol. 38, Issue 10 (Oct. 1, 2000).
Brar et al., "Engineered nanoparticles in wastewater and wastewater sludge—Evidence and impacts", Waste Management, pp. 504-520, vol. 30, Issue 3 (Mar. 2010).
Braun et al., "Presence of SARS-CoV-2-reactive T cells in COVID-19 patients and healthy donors", medRxiv, doi: https://doi.org/10.1101/2020.04.17.20061440 (Posted Apr. 22, 2020).
Bray et al., "Global cancer statistics 2018: GLOBOCAN estimates of incidence and mortality worldwide for 36 cancers in 185 countries", CA: A Cancer Journal for Clinicians, pp. 394-424, vol. 68, Issue 6 (Nov./Dec. 2018).
Bremer-Hoffmann et al., "Identification of regulatory needs for nanomedicines", Journal of Interdisciplinary Nanomedicine, pp. 4-15, vol. 3, Issue 1 (Apr. 2018).
Brevet et al., "Mannose-targeted mesoporous silica nanoparticles for photodynamic therapy", Chemical Communications, pp. 1475-1477, vol. 12 (Mar. 28, 2009).
Brinker et al., "Sol-Gel Science: The Physics and Chemistry of Sol-Gel Processing", Academic Press (1990).
Brister et al., "NCBI Viral Genomes Resource", Nucleic Acids Research, pp. D571-D577, vol. 43, Database issue (Jan. 2015).
Brooklyn, "Regulation of cancer cell migration and invasion by sphingosine-1-phosphate", World Journal of Biological Chemistry, pp. 307-312, vol. 1, Issue 10 (Oct. 26, 2010).
Broggi et al., "Type III interferons disrupt the lung epithelial barrier upon viral recognition", Science, 2pgs. 706-712, vol. 369 (Aug. 7, 2020).
Broxmeyer, L., "Is cancer just an incurable infectious disease?", Medical Hypotheses, pp. 986-996, vol. 63, Issue 6 (2004).
Bruun et al., "Engineering a Rugged Nanoscaffold to Enhance Plug-and-Display Vaccination", ACS Nano, pp. 8855-8866, vol. 12 (2018).
Bu et al., "Structural basis for the Receptor Binding Specificity of Norwalk Virus", Journal of Virology, pp. 5340-5347, vol. 82, Issue 11 (Jun. 1, 2008) Virol, 2008, 82(11):5340-5347. doi:10.1128/JVI.00135-08.
Buffin et al., "Influenza A and B virus-like particles produced in mammalian cells are highly immunogenic and induce functional antibodies", Vaccine, pp. 6857-6867, vol. 37, Issue 46 (Oct. 31, 2019).

(56) References Cited

OTHER PUBLICATIONS

Bunyavanich et al., "Nasal Gene Expression of Angiotensin-Converting Enzyme 2 in Children and Adults", JAMA, pp. 2427-2429, vol. 323, No. 23 (Jun. 16, 2020).

Bushman et al., "Population impact of SARS-CoV-2 variants with enhanced transmissibility and/or partial immune escape", pp. 6229-6242, vol. 184, Issue 26 (Dec. 22, 2021).

Butterfield, "Cancer vaccines", BMJ, doi: 10.1136/bmj.h988 (Published online Apr. 22, 2015).

Callaway, "Coronavirus Vaccine Trials Have Delivered Their First results—But Their Promise Is Still Unclear", Nature, pp. 363-364, vol. 581 (May 28, 2020).

Callaway, The Mutation That Helps Delta Spread Like Wildfire, Nature, pp. 472-473, vol. 596 (Aug. 26, 2021).

Carcione et al., "A Simulation of a COVID-19 Epidemic Based on a Deterministic SEIR Model", Frontiers in Public Health, pp. 1-13, vol. 8, Article 230 (May 2020).

Cardona et al., "Current challenges in open-source bioimage informatics", Nature Methods, pp. 661-665, vol. 9 (2012).

Carlsson et al., "Indications that Stockholm has reached herd immunity, given limited restrictions, against several variants of SARS-CoV-2", medRxiv (Posted Jul. 13, 2021) doi: https://doi.org/10.1101/2021.07.07.21260167.

Carmeliet, "VEGF as a key mediator of angiogenesis in cancer", Oncology, pp. 4-10, vol. 69 Suppl. 3 (Nov. 2005).

Carpenter et al., "A call for bioimaging software usability", Nature Methods, pp. 666-670, vol. 9, Issue 7 (Jun. 28, 2012).

Carping et al., "Comparison of the effects of 5- and 6-HOAt on model peptide coupling reactions relative to the cases for the 4- and 7-Isomers", Organic Letters, pp. 2253-2256, vol. 2, No. 15 (Jul. 27, 2000).

Carrilho et al., "Paper Microzone Plates", Analytical Chemistry, pp. 5990-5998, vol. 81, No. 20 (Jul. 2, 2009).

Carrillo-Conde et al., "Mannose-Functionalized "Pathogen-like" Polyanhydride Nanoparticles Target C-Type Lectin Receptors on Dendritic Cells", Molecular Pharmaceutics, pp. 1877-1886, vol. 8, Issue 5 (Sep. 1, 2011).

Caruana et al., "Diagnostic strategies for SARS-CoV-2 infection and interpretation of microbiological results", Clinical Microbiology and Infection, pp. 1178-1182, vol. 26, Issue 9 (Sep. 1, 2020).

Caruso et al., "Interrelated Mechanism by Which the Methide Quinone Celastrol, Obtained from the Roots of Tripterygium wilfordii, Inhibits Main Protease 3CLpro of COVID-19 and Acts as Superoxide Radical Scavenger", in 20 pages, vol. 21, Issue 23, 9266 (Dec. 1, 2020).

Casalino et al., "Shielding and Beyond: The Roles of Glycans in SARS-CoV-2 Spike Protein", Version 1. bioRxiv, Preprint, doi: 10.1101/2020.06.11.146522 (Jun. 11, 2020).

Cascão et al., "Celastrol: A Spectrum of Treatment Opportunities in Chronic Diseases", Frontiers in Medicine, pp. 1-18, vol. 4, Article 69 (Jun. 2017).

Castedo et al., "Cell death by mitotic catastrophe: A molecular definition", Oncogene, pp. 2825-2837, vol. 23 (2004).

Chambers et al., "Dissemination and growth of cancer cells in metastatic sites", Nature Reviews Cancer, pp. 563-572, vol. 2, Issue 8 (Aug. 2002).

Chandler et al., "SARS-CoV-2 exposure in wild white-tailed deer (*Odocoileus virginianus*)", Proceedings of the National Academy of Sciences of the United States of America, in 3 pages, vol. 118, No. 47 (2021).

Chang et al., "Nanoparticle composite TPNT1 is effective against SARS-CoV-2 and influenza viruses", Scientific Reports, in 13 pages, vol. 11, Article No. 8692 (2021).

Charest et al., "Fabrication of substrates with defined mechanical properties and topological features for the study of cell migration" Macro-Molecular Bioscience, pp. 12-20, vol. 2 (2012).

Chatterjee et al., "Nanoparticle-mediated hyperthermia in cancer therapy", Therapeutic Delivery, pp. 1001-1014, 2(8) (2011).

Chen et al., "Acute toxicological effects of copper nanoparticles in vivo", Toxicology Letters, pp. 109-120, vol. 163, Issue 2 (May 25, 2006).

Chen et al., "Biosafety in the preparation and processing of cytology specimens with potential coronavirus (COVID-19) infection", Cancer Cytopathology, pp. 309-316, doi:10.1002/cncy.22280 (May 2020).

Chen et al., "Containing COVID-19 Among 627,386 Persons in Contact With the Diamond Princess Cruise Ship Passengers Who Disembarked in Taiwan: Big Data Analytics", Journal of Medical Internet Research, e19540, vol. 22, No. 5 (2020).

Chen et al., "Development and Challenges of Antimicrobial Peptides for Therapeutic Applications", Antibiotics (Basel), in 20 pages, vol. 9, Issue 1 (Jan. 13, 2020).

Chen et al., "Inkjet Printed Conductive Tracks for Printed Electronics", ECS Journal of Solid State Science and Technology, pp. P3026-P3033, vol. 4 (2015).

Chen et al., "Probing the Dynamics of Doxorubicin-DNA Intercalation during the Initial Activation of Apoptosis by Fluorescence Lifetime Imaging Microscopy (FLIM)", PLOS One, E44947, vol. 7, Issue 9 (Sep. 2012) in 8 pages, www.plosone.org.

Chen et al., "Synthetic virus-like particles prepared via protein corona formation enable effective vaccination in an avian model of coronavirus infection", Biomaterials, pp. 111-118, vol. 106 (Nov. 2016).

Chen et al., "Titanium dioxide nanoparticles induce emphysema-like lung injury in mice", The Faseb Journal, pp. 2393-2395, vol. 20 Issue 13 (2006).

Chen et al., "Treating cancer stem cells and cancer metastasis using glucose-coated gold nanoparticles", International Journal of Nanomedicine, pp. 2065-2077, vol. 10 (2015).

Choquet et al., "Ports closed to cruise ships in the context of COVID-19: What choices are there for coastal states?", Annals of Tourism Research, in 10 pages, vol. 86 (20021).

Chow et al., "Induction of heat shock proteins in differentiated human and rodent neurons by celastrol", Cell Stress & Chaperones, pp. 237-244, vol. 12, Issue 3 (2007).

Chowell et al., "TCR contact residue hydrophobicity is a hallmark of immunogenic CD8+ T cell epitopes", The Proceedings of the National Academy of Sciences, pp. E1754-E1762, vol. 112, Issue 14 (Mar. 23, 2015).

Chu et al., "Physical distancing, face masks, and eye protection to prevent person-to-person transmission of SARS-CoV-2 and COVID-19: a systematic review and meta-analysis", The Lancet, pp. 1973-1987, vol. 395, Issue 10242 (Jun. 27, 2020.

Chung et al., "The effect of surface charge on the uptake and biological function of mesoporous silica nanoparticles in 3T3-L1 cells and human mesenchymal stem cells", Biomaterials, pp. 2959-2966, vol. 28, Issue 19 (Jul. 2007).

Clark et al., "Thyroid cancer: the case for total thyroidectomy", European Journal of Cancer, International Symposium on Controversies in the Management of Differentiated Thyroid Cancer, vol. 24, Issue 2, pp. 305-313 (Feb. 1, 1988).

Codreanu et al., "Successful Control of an Onboard COVID-19 Outbreak Using the Cruise Ship as a Quarantine Facility, Western Australia, Australia", Emerging Infectious Diseases, pp. 1279-1287, vol. 27, No. 5 (May 2021).

Cohen et al., "Influenza A penetrates host mucus by cleaving sialic acids with neuraminidase", Virology Journal, in 13 pages, vol. 10:321 (2013).

Cohen et al., "Mosaic nanoparticles elicit cross-reactive immune responses to zoonotic coronaviruses in mice", Science, pp. 735-741, vol. 371, Issue 6530 (Jan. 12, 2021).

Colleton et al., "Primary Human Immunodeficiency Virus Type 1-Specific CD8+ T-Cell Responses Induced by Myeloid Dendritic Cells", Journal of Virology, pp. 6288-6299, vol. 83, No. 12 (Jun. 2009).

Colson et al., "Culture and identification of a "Deltamicron" SARS-CoV-2 in a three cases cluster in southern France", in 26 pages, medRxiv, doi: https://doi.org/10.1101/2022.03.03.22271812 (2022).

Cooper, "The Development and Causes of Cancer", The Cell: A Molecular Approach, 2nd edition, Chapter 15, Sunderland (MA): Sinauer Associates Publisher (2000).

(56) References Cited

OTHER PUBLICATIONS

Copple et al., "Chemical tuning enhances both potency toward nrf2 and in vitro therapeutic index of triterpenoids", Toxicological Sciences, pp. 462-469, vol. 140, Issue 2 (Aug. 2014).

Corbett et al., "Immune Correlates of Protection by mRNA-1273 Immunization against SARS-CoV-2 Infection in Nonhuman Primates", bioRxiv., doi: https://doi.org/10.1101/2021.04.20.440647 (Posted Apr. 23, 2021).

Costa et al., "Modeling and comparison of dissolution profiles", European Journal of Pharmaceutical Sciences, pp. 123-133, vol. 13, Issue, Issue 2 (May 2001).

Cotto et al., "HSF1 granules: a novel stress-induced nuclear compartment of human cells", Journal of Cell Science, pp. 2925-2934, vol. 110, Issue 23 (Dec. 1997).

Covián et al., "BCG-Induced Cross-Protection and Development of Trained Immunity: Implication for Vaccine Design", Frontiers Immunology, Article 2806, vol. 10 (Nov. 2019).

Crookes-Goodson et al., "Bio-directed synthesis and assembly of nanomaterials", Chemical Society Reviews, pp. 2403-2412, vol. 37 (2008).

Cross et al., "Who funded the research behind the Oxford-AstraZeneca COVID-19 vaccine?", BMJ Global Health, in 11 pgs., vol. 6 (Dec. 22, 2021).

Crux et al., "Human Leukocyte Antigen (HLA) and Immune Regulation: How do Classical and Non-Classical HLA Alleles Modulate Immune Response to Human Immunodeficiency Virus and Hepatitis C Virus Infections?", Frontiers in Immunology, Article 832 in 26 pages (Published Jul. 18, 2017).

Da Silva, "An overview of the impact of COVID-19 in the cruise industry with considerations for Florida", Transportation Research Interdisciplinary Perspectives, in 7 pages, vol. 10, 100391 (2021).

Dahl, "Coronavirus (Covid-19) outbreak on the cruise ship Diamond Princess", International Maritime Health, pp. 5-8, vol. 71, No. 1 (2020).

Daniell et al., "Debulking SARS-CoV-2 in saliva using angiotensin converting enzyme 2 in chewing gum to decrease oral virus transmission and infection", Molecular Therapy, pp. 1966-1978, vol. 30, Issue 5 (May 4, 2022).

Day et al., "Multidisciplinary Approaches Identify Compounds that Bind to Human ACE2 or SARS-CoV-2 Spike Protein as Candidates to Block SARS-CoV-2-ACE2 Receptor Interactions", ASM Journals, mBio, e03681-20, vol. 12, No. 2 (Mar./Apr. 2021).

De Clercq et al., "Approved Antiviral Drugs over the Past 50 Years", Clinical Microbiology Reviews, pp. 695-747, vol. 29, No. 3 (2016).

De Silva et al., "Micro-Patterning of Animal Cells on PDMS Substrates in the Presence of Serum without Use of Adhesion Inhibitors", Biomedical Microdevices, pp. 219-222, vol. 6 (2004).

De Thonel et al., "Implication of Heat Shock Factors in Tumorigenesis: Therapeutical Potential", Cancers, pp. 1158-1181, vol. 3 (2011).

Dee et al., "Human Rhinovirus Infection Blocks Severe Acute Respiratory Syndrome Coronavirus 2 Replication Within the Respiratory Epithelium: Implications for COVID-19 Epidemiology", The Journal of Infectious Diseases, pp. 31-38, vol. 224, Issue 1 (Jul. 2021).

Del Agua et al., "Conducting Polymer Scaffolds Based on Poly(3,4-ethylenedioxythiophene) and Xanthan Gum for Live-Cell Monitoring", ACS Omega, pp. 7424-7431, vol. 3 (2018).

Delaugerre et al., "Prevention of SARS-CoV-2 transmission during a large, live, indoor gathering (SPRING): a non-inferiority, randomised, controlled trial", The Lancet, Infectious Diseases, pp. 341-348, vol. 22 (Mar. 2022).

Denesyuk et al., "NBCZone: Universal three-dimensional construction of eleven amino acids near the catalytic nucleophile and base in the superfamily of (chymo)trypsin-like serine fold proteases", International Journal of Biological Macromolecules, pp. 399-411, vol. 153 (2020).

Denisenko et al., "Mitotic catastrophe and cancer drug resistance: A link that must to be broken", Drug Resistance Updates, pp. 1-12, vol. 24 (2016).

Depellegrin et al., "The effects of COVID-19 induced lockdown measures on maritime settings of a coastal region", Science of the Total Environment, 140123, in 8 pages, vol. 740 (2020).

Derda et al., "Paper-supported 3D cell culture for tissue-based bioassays", The Proceedings of the National Academy of Sciences, pp. 18457-18462, vol. 106, No. 44 (Nov. 3, 2009).

Desai et al., "Design considerations for mesoporous silica nanoparticulate systems in facilitating biomedical applications", Mesoporous Biomater, pp. 16-43, vol. 1 (2014).

Desai, "Challenges in Development of Nanoparticle-Based Therapeutics", The AAPS Journal, pp. 282-295, vol. 14, No. 2 (Jun. 2012).

Devaux et al., "ACE2 receptor polymorphism: Susceptibility to SARS-CoV-2, hypertension, multi-organ failure, and COVID-19 disease outcome", Journal of Microbiology, Immunology and Infection, pp. 425-435, vol. 53, Issue 3 (Jun. 2020).

Diamond et al., "The Challenges of Vaccine Development against a New Virus during a Pandemic", Cell Host & Microbe, pp. 699-703, vol. 27, Issue 5 (2020).

Discher et al., "Tissues cells feel and respond to the stiffness of their substrate", Science, pp. 1139-1143, vol. 310, Issue 5751 (Nov. 18, 2005).

Doerfler, "Adenoviral Vector DNA- and SARS-CoV-2 mRNA-Based Covid-19 Vaccines: Possible Integration into the Human Genome—Are Adenoviral Genes Expressed in Vector-based Vaccines?", Virus Research, 198466 in 7 pages, vol. 302 (2021).

Döhla et al., "SARS-CoV-2 in environmental samples of quarantined households". medRxiv 2020.05.28.20114041; doi: https://doi.org/10.1101/2020.05.28.20114041 (2020).

Dolgin, "mRNA flu shots move into trials", Nature Reviews, Drug Discovery, pp. 801-803, vol. 20 (Nov. 2021).

Dolgin, "Publisher Correction: Treg engineers take aim at autoimmunity", Nature Biotechnology, p. 131, vol. 40 (Jan. 2022).

Domènech et al., "Cruise Passengers' Spatial Behaviour and Expenditure Levels at Destination", Tourism Planning & Development, pp. 17-36, vol. 17, No. 1 (2020).

Dong et al., "An interactive web-based dashboard to track COVID-19 in real time", The Lancet Infectious Diseases, pp. 533-534, vol. 20, Issue 5 (May 1, 2020).

Dooley et al., "Pooling analysis of scanning probe images", Surface Science, pp. 206-220, vol. 406, Issues 1-3 (May 31, 1998).

Dou et al., Overview of Proteasome Inhibitor-Based Anti-cancer Therapies: Perspective on Bortezomib and Second Generation Proteasome Inhibitors versus Future Generation Inhibitors of Ubiquitin-Proteasome System, Current Cancer Drug Targets, pp. 517-536, vol. 14, Issue 6 (2014).

Drozdetskiy et al., "JPred4: a protein secondary structure prediction server", Nucleic Acids Research, pp. W389-W394, vol. 43, Issue W1 (Jul. 1, 2015).

Dubey et al., "Heat shock proteins: a therapeutic target worth to consider", Veterinary World, pp. 46-51, vol. 8 (2015).

Dubois et al., "Colorimetric Method for Determination of Sugars and Related Substances", Analytical Chemistry, pp. 350-356, vol. 28, Issue 3 (Mar. 1, 1956).

Dubrez et al., "IAP proteins as targets for drug development in oncology", OncoTargets and Therapy, pp. 1285-1304, vol. 6 (2013).

Duineveld, "The stability of ink-jet printed lines of liquid with zero receding contact angle on a homogeneous substrate", Journal of Fluid Mechanics, pp. 175-200, vol. 477 (2003).

Durocher et al., "High-level and high-throughput recombinant protein production by transient transfection of suspension-growing human 293-EBNA1 cells", Nucleic Acids Research, p. e9, vol. 30, No. 2 (Jan. 15, 2002).

Eckelman et al., "The human anti-apoptotic proteins cIAP1 and cIAP2 bind but do not inhibit caspases", The Journal of Biological Chemistry, Enzyme Catalysis and Regulation, pp. 3254-3260, vol. 281, Issue 6 (Feb. 2006).

Edwards et al., "Academic Research in the 21st Century: Maintaining Scientific Integrity in a Climate of Perverse Incentives and Hypercompetition", Environmental Engineering Science, pp. 51-61, vol. 34, No. 1 (2017).

(56) References Cited

OTHER PUBLICATIONS

El-Faham et al., "Novel Proton Acceptor Immonium-Type Coupling Reagents: Application in Solution and Solid-Phase Peptide Synthesis", Organic Letters, pp. 4475-4477, vol. 9, Issue 22 (2007).
Eliceiri et al., "Biological imaging software tools", Nature Methods, pp. 697-710, vol. 9 (2012).
Elmore, "Apoptosis: a review of programmed cell death" Toxicologic Pathology, pp. 495-516, vol. 35, Issue 4 (2007).
Elnakat et al., "Distribution, functionality and gene regulation of folate receptor isoforms: implications in targeted therapy", Advanced Drug Delivery, pp. 1067-1084, vol. 56, Issue 8 (Apr. 29, 2004).
Emami et al., "Drying Technologies for the Stability and Bioavailability of Biopharmaceuticals", Pharmaceutics, vol. 10, 131 in 22 pages (2018).
Engelking, Larry R., "Chapter 6—Enzyme Kinetics" Editor: Larry R. Engelking, Textbook of Veterinary Physiological Chemistry (Third Edition), pp. 32-38 (2015) ISBN 9780123919090.
Eshbach et al., "Receptor-Mediated Endocytosis in the Proximal Tubule", Annual Review of Physiology, pp. 425-448, vol. 79 (2017).
Esparza et al., "High affinity nanobodies block SARS-CoV-2 spike receptor binding domain interaction with human angiotensin converting enzyme", Scientific Reports, vol. 10, Article No. 22370, in 13 pages (2020).
Esposito et al., "Chemotherapy against cancer during pregnancy: A systematic review on neonatal outcomes", Medicine, pp. 1-6, vol. 95, Issue 38 (2016).
Etienne-Manneville, "Actin and microtubules in cell motility: which one is in control?", Traffic, pp. 470-477, vol. 5, Issue 7 (Jul. 2004).
Falconnet et al., "Surface engineering approaches to micropattern surfaces for cell-based assays". Biomaterials, pp. 3044-3063, vol. 27, Issue 16 (Jun. 2006).
Fan et al., "Acute respiratory distress syndrome advances in diagnosis and treatment", The Journal of the American Medical Association, pp. 698-710, vol. 319, Issue 7 (2018).
Fang et al., "How many infections of COVID-19 there will be in the 'Diamond Princess'—Predicted by a virus transmission model based on the simulation of crowd flow". arXi, 10616 (2002).
Fantini et al., "Structural dynamics of SARS-CoV-2 variants: A health monitoring strategy for anticipating Covid-19 outbreaks", The Journal of Infection, pp. 197-206, vol. 83, Issue 2 (Aug. 2021).
Farokhzad et al., "Impact of Nanotechnology on Drug Delivery", ACS Nano, pp. 16-20, Vo. 3, Issue 1 (2009).
Faulkner, "Towards a framework for tourism disaster management", Tourism Management, pp. 135-147, vol. 22, Issue 2 (Apr. 2001).
Feikin et al., "Estimating the Percentage of a Population Infected with SARS-CoV-2 Using the Number of Reported Deaths: A Policy Planning Tool", Pathogens, 838, in 11 pages, vol. 9 (2020).
Feng et al., "COVID-19 with Different Severities: A Multicenter Study of Clinical Features", American Journal of Respiratory and Critical Care Medicine, pp. 130-1388, vol. 201, No. 11 (Jun. 1, 2020).
Feng et al., "Multi-Epitope Vaccine Design Using an Immunoinformatic Approach for SARS-CoV-2", Pathogens, in 16 pages, vol. 10, Issue 6 (2021).
Fenton et al., "Multidimensional scaling and tourism research", Annals of Tourism Research, pp. 236-254, vol. 15, Issue 2 (1988).
Finzi, "Treatment of SARS-CoV-2 with high dose oral zinc salts: A report on four patients", International Journal of Infectious Diseases, pp. 307-309, vol. 99 (Oct. 1, 2020).
Firth et al., "Using a real-world network to model localized COVID-19 control strategies", Nature Medicine, pp. 1616-1622, vol. 26 (Oct. 2020).
Fisher et al., "Community and Close Contact Exposures Associated with COVID-19 Among Symptomatic Adults ≥18 Years in 11 Outpatient Health Care Facilities United States, 2020", Morbidity and Mortality Weekly Report, pp. 1258-1264, vol. 69, No. 36 (Sep. 11, 2020).

Fleri et al., "The Immune Epitope Database and Analysis Resource in Epitope Discovery and Synthetic Vaccine Design", Frontiers in Immunology, pp. 1-16., vol. 8, Article 278 (Mar. 2017).
Flora et al., "26—Medical Countermeasures—Chelation Therapy" Handbook of Arsenic Toxicology, pp. 589-626, ISBN: 978-0-12-418688-0, Academic Press (2015).
Florindo et al., "Immune-mediated approaches against COVID-19", Nature Nanotechnology, pags. 630-645,vol. 15 (2020).
Floyd et al., "Profiling risk perceptions of tourists", Annals of Tourism Research, pp. 1051-1054, vol. 31, No. 4 ref. 6 (2004).
Fosgerau et al., "Peptide therapeutics: current status and future directions", Drug Discovery Today, pp. 122-128, vol. 20, Issue 1 (Jan. 2015).
Franchi et al., "The inflammasome: a caspase-1-activation platform that regulates immune responses and disease pathogenesis", Nature Immunology, pp. 241-247, vol. 10 (2009).
Franco et al., "Limits and prospects of the "incremental approach" and the European legislation on the management of risks related to nanomaterials", Regulatory Toxicology and Pharmacology, pp. 171-183, vol. 48, Issue 2 (Jul. 2007).
Frimat et al., "Plasma stencilling methods for patterning", Analytical and Bioanalytical Chemistry, pp. 601-609, vol. 395 (2009).
Fröhlich, "The role of surface charge in cellular uptake and cytotoxicity of medical nanoparticles", International Journal of Nanomedicine, pp. 5577-5591, vol. 7 (2012).
Fu et al., "The absorption, distribution, excretion and toxicity of mesoporous silica nanoparticles in mice following different exposure routes", Biomaterials, pp. 2565-2575, vol. 34, Issue 10 (Mar. 2013).
Fuentes-Prior et al., "The protein structures that shape caspase activity, specificity, activation and inhibition", Biochemical Journal, pp. 201-232, vol. 384 (2004).
Fujiwara et al., "Anthracycline Antibiotics", Critical Reviews in Biotechnology, pp. 133-157, vol. 3, Issue 2 (1985).
Funke et al., "Natural killer cells in HIV-1 infection: a double-edged sword", AIDS Reviews, pp. 67-76, vol. 13, Issue 2 (Apr.-Jun. 2011).
Gaikwad et al., "Antibody-Dependent Complement Responses toward SARS-CoV-2 Receptor-Binding Domain Immobilized on "Pseudovirus-like" Nanoparticles", ACS Nano, (May 4, 2022) acsnano.2c02794.
Gallo et al., "The central role of the nasal microenvironment in the transmission, modulation, and clinical progression of SARS-CoV-2 infection", Mucosal Immunology, pp. 305-316, vol. 14 (2021).
Galluzzi et al., "Molecular definitions of cell death subroutines: recommendations of the Nomenclature Committee on Cell Death 2012", Cell Death and Differentiation, pp. 107-120, vol. 19 (2012).
Galluzzi et al., "Non-apoptotic functions of apoptosis-regulatory proteins", EMBO Reports, pp. 322-330, vol. 13, No. 4 (2012).
Galm et al., "Antitumor Antibiotics: Bleomycin, Enediynes, and Mitomycin", Chemical Reviews, pp. 739-758, pp. 105, Issue 2 (2005).
Gao et al., "Ancestral SARS-CoV-2-specific T cells cross-recognize the Omicron variant", Nature Medicine, pp. 472-476, vol. 28 (Mar. 2022).
Gao et al., "Development of an inactivated vaccine candidate for SARS-CoV-2", Science, pp. 77-81, vol. 369 (2020).
Gary-Bobo et al., "Cancer therapy improvement with mesoporous silica nanoparticles combining targeting, drug delivery and PDT", International Journal of Pharmaceutics, pp. 509-515, vol. 423—Issue 2 (Feb. 28, 2012) 10.1016/j.ijpharm.2011.11.045.
Gaviria et al., "A network analysis of COVID-19 mRNA vaccine patents", Nature Biotechnology, pp. 546-548, vol. 39 (2021).
Ge et al., "Celastrol causes apoptosis and cell cycle arrest in rat glioma cells", Neurological Research, pp. 94-100, vol. 32, Issue 1: Neuromyology II (2010).
Ge et al., "Low-cost, abundant, binary sulfides as promising thermoelectric materials", Materials Today, pp. 227-239, vol. 19, Issue 4 (May 2016).
Geng et al., "Thio-glucose bound gold nanoparticles enhance radio-cytotoxic targeting of ovarian cancer", Nanotechnology, 285101, vol. 22, No. 28 (2011).
Gerlowski et al., "Microvascular permeability of normal and neoplastic tissues", Microvascular Research, pp. 288-305, vol. 31, Issue 3 (May 1986).

(56) References Cited

OTHER PUBLICATIONS

Ghaffari et al., "Inhibition of H1N1 influenza virus infection by zinc oxide nanoparticles: another emerging application of nanomedicine", Journal of Biomedical Science, in 10 pages, 26:70 (2019) https://doi.org/10.1186/S12929-019-0563-4.

Gialeli et al., "Roles of matrix metalloproteinases in cancer progression and their pharmacological targeting", The FEBS Journal, pp. 16-27, vol. 278, Issue 1 (Jan. 2011).

Giang et al., "Prodrug applications for targeted cancer therapy", The American Association of Pharmaceutical Scientists Journal, pp. 899-913, vol. 16, No. 5 (Sep. 2014).

Gil et al., "Nanopharmacy: Inorganic nanoscale devices as vectors and active compounds", Pharmacological Research, pp. 115-125, vol. 62, Issue 2 (Aug. 2010).

Gilstrap et al., "Initiation, Continuation, or Withdrawal of Angiotensin-Converting Enzyme Inhibitors/Angiotensin Receptor Blockers and Outcomes in Patients Hospitalized With Heart Failure With Reduced Ejection Fraction", Journal of the American Heart Association, in 21 pages, vol. 6, Issue 2 (Feb. 2, 2017).

Godbey et al., "Size matters: molecular weight affects the efficiency of poly(ethylenimine) as a gene delivery vehicle", Journal of Biomedical Materials Research, pp. 268-275, vol. 45, Isue 3 (Jun. 5, 1999).

Goel et al., "Synthesis and biomedeal application of copper sulfide nanoparticles: from sensors to theranostics", Small, pp. 631-645, vol. 10, Issue 4 (Feb. 26, 2014).

Goel et al., "VEGF targets the tumour cell", Nature Reviews Cancer, pp. 871-882, vol. 13 (2013).

Golstein et al., "Cell death by necrosis: towards a molecular definition", Trends in Biochemical Sciences, pp. 37-43, vol. 32, Issue 1 (Jan. 1, 2007).

Goñi, "The basic structure and dynamics of cell membranes: An update of the Singer-Nicolson model", Biochimica et Biophysica Acta, pp. 1467-1476, vol. 1838, Issue 6 (Jun. 2014).

González Ordóñez et al., "Risk of venous thromboembolism associated with the insertion/deletion polymorphism in the angiotensin-converting enzyme gene", Blood Coagulation and Fibrinolysis, pp. 485-490, vol. 11, Issue 5 (Jul. 2000).

Gonzalez-Rodriguez et al., "Dynamics of Receptor-Mediated Nanoparticle Internalization into Endothelial Cells", . PLoS One, in 23 pages, vol. 10, Issue 4 (2015) e0122097. doi: 10.1371/journal.pone.0122097.

Goodsell, "The molecular perspective: methotrexate", Stem Cells, pp. 314-315, vol. 17, Issue 5 (1999).

Gordon et al., "Immortality, but not oncogenic transformation, of primary human cells leads to epigenetic reprogramming of DNA methylation and gene expression", Nucleic Acids Research, pp. 3529-3541, vol. 42, Issue 6 (Apr. 1, 2014).

Gorshkov et al., "Quantum Dot-Conjugated SARS-CoV-2 Spike Pseudo-Virions Enable Tracking of Angiotensin Converting Enzyme 2 Binding and Endocytosis", ACS Nano, pp. 12234-12247, vol. 14 (2020).

Gottesman et al., "Multidrug resistance in cancer: role of ATP-dependent transporters", Nature Reviews Cancer, pp. 48-58, vol. 2 (2002).

Gould et al., "Contributing Factors in Restaurant-Associated Foodborne Disease Outbreaks, FoodNet Sites, 2006 and 2007", Journal of Food Protection, pp. 1824-1828, vol. 76, Issue 11 (Nov. 1, 2013).

Gouveia et al., "Good manufacturing practices for medicinal products for human use", Journal of Pharmacy & BioAllied Sciences, pp. 87-96, vol. 7, Issue 2 (2015).

Graziano et al., "Norovirus Attachment and Entry", Viruses, in 13 pages, vol. 11 (2019).

Greaney et al., "Complete Mapping of Mutations to the SARS-CoV-2 Spike Receptor-Binding Domain that Escape Antibody Recognition", Cell Host & Microbe, pp. 44-57.E9, vol. 29, Issue 1 (Jan. 13, 2021).

Greenwood et al., "Chemistry of the Elements, 2nd Edition", Butterworth-Heinemann, (Nov. 11, 1997) Paperback ISBN: 9780750633659.

Grey et al., "Wound assessment", BMJ, pp. 285-288, vol. 332 (2006).

Griffiths et al., "IGF1R is an entry receptor for respiratory syncytial virus", Nature, pp. 615-619, vol. 583 (2020).

Grifoni et al., "A Sequence Homology and Bioinformatic Approach Can Predict Candidate Targets for Immune Responses to SARS-CoV-2", Cell Host & Microbe, pp. 671-680, vol. 27, Issue 4 (Apr. 8, 2020).

Grifoni et al., "Targets of T Cell Responses to SARS-CoV-2 Coronavirus in Humans with COVID-19 Disease and Unexposed Individuals", Cell, pp. 1489-1501, vol. 181, Issue 7 (Jun. 25, 2020).

Gudmundsdottir et al., "Inactivation of SARS-CoV-2 and HCoV-229E in vitro by ColdZyme® a medical device mouth spray against the common cold", Journal of Medical Virology, pp. 1792-1795, vol. 93, Issue 3 (Mar. 2021).

Guertler et al., "The WST survival assay: an easy and reliable method to screen radiation-sensitive individuals", Radiation Protection Dosimetry, pp. 487-490, vol. 143, Issue 2-4 (Feb. 2011).

Gumbiner, "Cell Adhesion: The Molecular Basis of Tissue Architecture and Morphogenesis", Cell, pp. 345-357, vol. 84, Issue 3 (Feb. 9, 1996).

Guo et al., "Fundamentals and Applications of Nanomaterials", ISBN:-13: 978-1-59693-262-3, Artech House Publishers, Norwood, MA (2009).

Gurunathan et al., "Antiviral Potential of Nanoparticles—Can Nanoparticles Fight Against Coronaviruses?", Nanomaterials, in 29 pages, 1645, vol. 10, Issue 9 (2020).

Gutkin et al., "RNA delivery with a human virus-like particle", Nature Biotechnology, pp. 1514-1515, vol. 39 (2021).

Gyrd-Hansen et al., "IAPs: from caspase inhibitors to modulators of NF-kappaB, inflammation and cancer", Nature Reviews Cancer, pp. 561-574, vol. 10 (2010).

Ha, "Dietary Salt Intake and Hypertension", Electrolyte Blood Press, pp. 7-18, vol. 12 (2014).

Haabeth et al., "An mRNA SARS-CoV-2 Vaccine Employing Charge-Altering Releasable Transporters with a TLR-9 Agonist Induces Neutralizing Antibodies and T Cell Memory", ACS Central Science, pp. 1191-1204, vol. 7 (2021).

Hadjadj et al., "Impaired type I interferon activity and inflammatory responses in severe COVID-19 patients", Science, pp. 718-724, vol. 369, Issue 6504 (Jul. 13, 2020).

Haghi et al., "Advanced Nanotube and Nanofiber Materials", Nanotechnology Science and Technology, Novinka, ISBN: 978-1-62081-170-2 (Jul. 2012).

Hamdi et al., "Investigating the Internalization and COVID-19 Antiviral Computational Analysis of Optimized Nanoscale Zinc Oxide", ACS Omega, pp. 6848-6860, vol. 6 (2021).

Hammerstedt et al., "Commercialization of basic research from within the university and return of value to the public", Animal Reproduction Science, pp. 158-178, vol. 105, 1-2 (2008).

Han et al., "Computational Design of ACE2-Based Peptide Inhibitors of SARS-CoV-2", ACS Nano, pp. 5143-5147, vol. 14 (2020).

Han et al., "Protein-modified hollow copper sulfide nanoparticles carrying indocyanine green for photothermal and photodynamic therapy", Journal of Materials Chemistry B, pp. 105-112, Issue 1 (2016).

Hanahan et al., "The Hallmarks of Cancer", Cell, pp. 57-70, vol. 100, Issue 1 (Jan. 7, 2000).

Handy et al., "The ecotoxicology of nanoparticles and nanomaterials: current status, knowledge gaps, challenges, and future needs", Ecotoxicology, pp. 315-325, vol. 17 (2008).

Hanke et al., "An alpaca nanobody neutralizes SARS-CoV-2 by blocking receptor interaction", nature Communications, in 9 pages, vol. 11:4420 (2020).

Hao et al., "In vitro degradation behavior of silica nanoparticles under physiological conditions", Journal of Nanoscience and Nanotechnology, pp. 6346-6354, vol. 12, No. 8 (2012).

Harndahl et al., Peptide-MHC class I stability is a better predictor than peptide affinity of CTL immunogenicity, European Jourmnal of Immunology, pp. 1405-1416, vol. 42, Issue 6 (2012).

Hartig, "Basic Image Analysis and Manipulation in ImageJ", Current Protocols in Molecular Biology, pp. 1-14, Chapter14 (2013).

(56) References Cited

OTHER PUBLICATIONS

Hartung, "Rebooting the Generally Recognized as Safe (GRAS) Approach for Food Additive Safety in the US", Altex, pp. 3-25, vol. 35, No. 1 (2018).

Harvey et al., "SARS-CoV-2 variants, spike mutations and immune escape", Nature Reviews Microbiology, pp. 409-424, vol. 19 (Jul. 2021).

Hasnidawani et al., "Synthesis of ZnO Nanostructures Using Sol-Gel Method", Procedia Chemistry, pp. 211-216, vol. 19 (2016).

Hatmal et al., "Comprehensive Structural and Molecular Comparison of Spike Proteins of SARS-CoV-2, SARS-CoV and MERS-CoV, and Their Interactions with ACE2" Cells, in 37 pages, 2638, vol. 9 (2020).

He et al., "In vivo biodistribution and urinary excretion of mesoporous silica nanoparticles: effects of particle size and PEGylation", Small, pp. 271-280, vol. 7, Issue 2 (2011).

He et al., "Single-component, self-assembling, protein nanoparticles presenting the receptor binding domain and stabilized spike as SARS-CoV-2 vaccine candidates", Science Advances, in 17 pages, vol. 7, eabf1591, (Mar. 19, 2021).

He et al., "Temporal dynamics in viral shedding and transmissibility of COVID-19", Nature Medicine, pp. 672-675, vol. 26 (2020).

He et al., "The three-stage in vitro degradation behavior of mesoporous silica in simulated body fluid", Microporous and Mesoporous Materials, pp. 314-320, vol. 131 (2010).

Heskin et al., "Caution required with use of ritonavir-boosted PF-07321332 in COVID-19 management", The Lancet, pp. 21-22, vol. 399, Issue 10319 (Jan. 1, 2022).

Heus et al., "Importance of intellectual property generated by biomedical research at universities and academic hospitals", Journal of Clinical and Translational Research, pp. 250-259, vol. 3, Issue 2 (2017).

Heymann, Data sharing and outbreaks: best practice exemplified, The Lancet, pp. 469-470, vol. 3955, Issue 10223 (Feb. 15, 2020).

Hilgendorf et al., "The retinoblastoma protein induces apoptosis directly at the mitochondria", Genes & Development, pp. 1003-1015, vol. 27 (2013).

Hillaireau et al., "Nanocarriers' entry into the cell: relevance to drug delivery", Cellular and Molecular Life Sciences, pp. 2873-2896, vol. 66 (2009).

Hillen et al., "Structure of replicating SARS-CoV-2 polymerase", Nature, pp. 154-156, vol. 584 (Aug. 6, 2020).

Hoffmann et al., "SARS-CoV-2 Cell Entry Depends on ACE2 and TMPRSS2 and Is Blocked by a Clinically Proven Protease Inhibitor", Cell, pp. 271-280, vol. 181, Issue 2 (2020).

Hoffmann et al., "SARS-CoV-2 variants B.1.351 and P.1 escape from neutralizing antibodies", Cell, pp. 2384-2393, vol. 184, Issue 9 (Apr. 29, 2021).

Hoffmann et al., "Silica-based mesoporous organic-inorganic hybrid materials", Angewandte Chemie International Edition, A Journal of the German Chemical Society, pp. 3216-3251, vol. 45, Issue 20 (May 12, 2006).

Holland et al., "Cruising through a pandemic: The impact of COVID-19 on intentions to cruise", Transportation Research Interdisciplinary Perspectives, in 15 pages, 100328, vol. 9 (2021).

Holland, "Risk perceptions of health and safety in cruising", AIMS Geosciences, pp. 422-436, vol. 6, Issue 4 (2020).

Holmberg et al., "Formation of nuclear HSF1 granules varies depending on stress stimuli", Cell Stress & Chaperones, pp. 219-228, vol. 5, Issue 3 (2000).

Homer-Vanniasinkam et al., "The continuing challenges of translational research: clinician-scientists' perspective", Cardiology Research and Practice, vol. 2012, Article ID 246710, in 5 pages (2012).

Hongmei, "Extrinsic and Intrinsic Apoptosis Signal Pathway Review", Ntuli, T. M., editor. Apoptosis and Medicine [Internet]. London: IntechOpen; 2012 [cited Jun. 22, 2022]. Available from: https://www.intechopen.com/chapters/38236 doi: 10.5772/50129.

Horejs, "From lipids to lipid nanoparticles to mRNA vaccines", Nature Review Materials, pp. 1075-1076, vol. 6 (2021).

Hortobagyi, "Overview of treatment results with trastuzumab (Herceptin) in metastatic breast cancer", Seminars in Oncology, pp. 43-47, vol. 28, Supplement 18 (Dec. 2001).

Hosseini et al., "Cholesterol-rich lipid-mediated nanoparticles boost of transfection efficiency, utilized for gene editing by CRISPR-Cas9", International Journal of Nanomedicine, pp. 4353-4366, vol. 14 (2019).

Hou et al., "SARS-CoV-2 Reverse Genetics Reveals a Variable Infection Gradient in the Respiratory Tract", Cell, pp. 429-446, vol. 182, Issue 2 (Jul. 23, 2020).

Housman et al., "Drug Resistance in Cancer: An Overview", pp. 1769-1792, vol. 6, Issue 3 (2014).

Hu et al., "Recent advances of cocktail chemotherapy by combination drug delivery systems", Advanced Drug Delivery Reviews, pp. 19-34, vol. 98 (2016).

Huang et al., "Applications of nanoparticle drug delivery systems for the reversal of multidrug resistance in cancer", Oncology Letters, pp. 11-15, vol. 12, Issue 1 (Jul. 2016).

Huang et al., "Copper Sulfide Nanoparticles with Phospholipid-PEG Coating for In Vivo Near-Infrared Photothermal Cancer Therapy", Chemistry, an Asian Journal, pp. 370-376, vol. 10, Issue 2 (Feb. 2015).

Huang et al., "Novel Peptide Inhibitors of Angiotensin-converting Enzyme 2*", Journal of Biological Chemistry, pp. 15532-15540, vol. 278, Issue 18 (May 2003).

Huang et al., "Taking Account of Asymptomatic Infections in Modeling the Transmission Potential of the COVID-19 Outbreak on the Diamond Princess Cruise Ship", medRxiv, Apr. 22, 2020, 20074286; doi: https://doi.org/10.1101/2020.04.22.20074286.

Huang et al., "The promotion of human malignant melanoma growth by mesoporous silica nanoparticles through decreased reactive oxygen species", Biomaterials, pp. 6142-6153, vol. 31, Issue 24 (Aug. 2010).

Huang et al., "The Toxicity of Nanoparticles Depends on Multiple Molecular and Physicochemical Mechanisms", International Journal of Molecular Sciences, in 13 pages, vol. 18, 2702 (2017).

Huennekens, "The methotrexate story: a paradigm for development of cancer chemotherapeutic agents", Advances in Enzyme Regulation, pp. 397-419, vol. 34 (1994).

Humphrey et al., "VMD: Visual molecular dynamics", Journal of Molecular Graphics, pp. 33-38, vol. 14, Issue 1 (Feb. 1996).

Huo et al., "Neutralization of SARS-CoV-2 by Destruction of the Prefusion Spike", Cell Host & Microbe, pp. 445-454, vol. 28, Issue 3 (Sep. 9, 2020).

Hussain et al., "Acylation of Cellulose with N,N'-Carbonyldiimidazole-Activated Acids in the Novel Solvent Dimethyl Sulfoxide/Tetrabutylammonium Fluoride", Macromolecular Rapid Communications, pp. 916-920, vol. 25, Issue 9 (May 2004).

Hystad et al., "Towards a destination tourism disaster management framework: Long-term lessons from a forest fire disaster", Tourism Management, pp. 151-162, vol. 29, Issue 1 (Feb. 2008).

Ihalainen et al., "Paper-supported nanostructured ultrathin gold film electrodes—Characterization and functionalization", Applied Surface Science, pp. 321-329, vol. 329 (Feb. 2015).

Ihalainen et al., "Topographical, chemical, thermal and electrostatic properties of latex films", Colloids and Surfaces A Physicochemical and Engineering Aspects, pp. 320-330, vol. 354 (2010).

Ikuma et al., "When nanoparticles meet biofilms—interactions guiding the environmental fate and accumulation of nanoparticles", Frontiers in Microbiology, in 6 pages, vol. 6, Article 591 (2015).

Irmler et al, "Inhibition of death receptor signals by cellular FLIP", Nature, pp. 190-195, vol. 388 (Jul. 10, 1997).

Ishizuka et al., "Quantitating T Cell Cross-Reactivity for Unrelated Peptide Antigens", The Journal of Immunology, pp. 4337-4345, vol. 183, Issue 7 (Oct. 1, 2009).

Ito et al., "The cruise industry and the COVID-19 outbreak", Transportation Research Interdisciplinary Perspectives, 100136, in 11 pages, vol. 5 (May 2020).

Izquierdo et al., "Overexpression of the ABC transporter TAP in multidrug-resistant human cancer cell lines", British Journal of Cancer, pp. 1961-1967, vol. 74 (1996).

(56) References Cited

OTHER PUBLICATIONS

Jacob et al., "The Impact of Research Grant Funding on Scientific Productivity", Journal of Public Economics, pp. 1168-1177, vol. 95 (2011).
Jacobs et al., "Human rhinoviruses", Clinical Microbiology Reviews, pp. 135-162, vol. 26, Issue 1 (Jan. 2013).
Jafri et. Al, "Roles of telomeres and telomerase in cancer, and advances in telomerase-targeted therapies", Genome Medicine, Article No. 69, in 18 pages, vol. 8 (2016).
Jain, "The Handbook of Nanomedicine Third Edition", ISBN: 978-1-4939-6965-4 (Jan. 2017).
Jain, "Understanding barriers to drug delivery: high resolution in vivo imaging is key", Clinical Cancer Research, pp. 1605-1606, vol. 5, Issue 7 (1999).
Järnström et al., "Roughness of pigment coatings and its influence on gloss", Applied Surface Science, pp. 5741-5749, vol. 254, Issue 18 (Jul. 15, 2008).
Jensen et al., "Miniaturized Plate Readers for Low-Cost, High-Throughput Phenotypic Screening", Journal of Laboratory Automation, pp. 51-55, vol. 20, Issue 1 (2015).
Jiang et al., "SARS-CoV-2 Spike Impairs DNA Damage Repair and Inhibits V(D)J Recombination In Vitro", Viruses, 2056 in 10 pages, vol. 13 (2021).
Jiang et al., "Bacterial toxicity comparison between nano- and micro-scaled oxide particles", Environmental Pollution, pp. 1619-1625, vol. 157, Issue 5 (May 2009).
Jing et al., "SARS-CoV-2 infection causes immunodeficiency in recovered patients by downregulating CD19 expression in B cells via enhancing B-cell metabolism", Signal Transduction and Targeted Therapy, Article No. 345, vol. 6 (2021).
Jo et al., "Design and Fabrication of Streptavidin-Functionalized, Fluorescently Labeled Polymeric Nanocarriers", Langmuir, pp. 15783-15794, vol. 34, Issue 51 (2018).
Jo et al., "Natural Product Celastrol Destabilizes Tubulin Heterodimer and Facilitates Mitotic Cell Death Triggered by Microtubule-Targeting Anti-Cancer Drugs", PLoS One, e10318 in 12 pages, vol. 5, Issue 4 (Apr. 2010).
Johansson et al., "SARS-CoV-2 Transmission From People Without COVID-19 Symptoms", JAMA Network Open, e2035057 in 8 pages, vol. 4, Issue 1 (2021).
Johnson et al., "NCBI Blast: a better web interface", Nucleic Acids Rsearch, pp. W5-W9, vol. 36 (2008).
Jolly et al., "In vivo binding of active heat shock transcription factor 1 to human chromosome 9 heterochromatin during stress", The Journal of Cell Biology, pp. 775-781, vol. 156, No. 5 (Mar. 4, 2002).
Jorgensen et al., "Comparison of simple potential functions for simulating liquid water", AIP The Journal of Chemical Physics, pp. 926-935, vol. 79, Issue 2 (1983).
Joyce et al., "SARS-CoV-2 ferritin nanoparticle vaccines elicit broad SARS coronavirus immunogenicity", Cell Reports, 110143, vol. 37, Issue 12 (Dec. 21, 2021) DOI:https://doi.org/10.1016/j.celrep.2021.110143.
Justus et al., "In vitro cell migration and invasion assays", Journal of Visualized Experiments, 51046, vol. 88 (Jun. 1, 2014) doi: 10.3791/51046.
Juvonen et al., "Biocompatibility of printed paper-based arrays for 2-D cell cultures", Acta Biomaterialia, pp. 6704-6710, vol. 9, Issue 5 (May 2013).
Juvonen et al., "Enhanced protein adsorption and patterning on nanostructured latex-coated paper", Colloids and SurfacesB: Biointerfaces, pp. 261-269, vol. 118 (Jun. 1, 2014).
Juvonen et al., "Protein and bacterial interactions with nanostructured polymer coatings", Colloids and Surfaces B: Biointerfaces, pp. 527-535, vol. 136 (Dec. 1, 2015).
Kain et al., "The chick embryo as an expanding experimental model for cancer and cardiovascular research", Developmental Dynamics, pp. 216-228, vol. 243, Issue 2 (Feb. 2014).
Kalepua et al., "Insoluble drug delivery strategies: review of recent advances and business prospects", Acta Pharmaceutica Sinica B, pp. 442-453, vol. 5, Issue 5 (Sep. 2015).
Kalhori et al., "FTY720 (Fingolimod) attenuates basal and sphingosine-1-phosphate-evoked thyroid cancer cell invasion", Endocrine-Related Cancer, pp. 457-468, vol. 23, Issue 5 (2016).
Kalil et al., "Influenza virus-related critical illness: pathophysiology and epidemiology", Critical Care, Article No. 258, vol. 23 (2019) https://doi.org/10.1186/s13054-019-2539-x.
Kalluri et al., "The basics of epithelial-mesenchymal transition", Journal of Clinical Investigation, pp. 1420-1428, vol. 119, No. 6 (Jun. 2009).
Kamyshny et al., "Metal-based Inkjet Inks for Printed Electronics", The Open Applied Physics Journal, pp. 19-36, vol. 4 (2011).
Kanekiyo et al., "Mosaic nanoparticle display of diverse influenza virus hemagglutinins elicits broad B cell responses", Nature Immunology, pp. 362-372, vol. 20 (2019).
Kanekiyo et al., "Rational Design of an Epstein-Barr Virus Vaccine Targeting the Receptor-Binding Site", Cell, pp. 1090-1100, vol. 162 (Aug. 27, 2015).
Kang et al., "Rapid Development of SARS-CoV-2 Spike Protein Receptor-Binding Domain Self-Assembled Nanoparticle Vaccine Candidates", ACS Nano, pp. 2738-2752, vol. 15 (2021).
Kang et al., "Rapid development of SARS-CoV-2 receptor binding domain-conjugated nanoparticle vaccine candidate", bioRxiv, pp. 1-52 (2020).
Kankaanpää et al., "BioImageXD: an open, general-purpose and high-throughput image-processing platform", Nature Methods, pp. 683-689, vol. 9 (2012).
Kanojia et al., "Developments in the formulation and delivery of spray dried vaccines", Human Vaccines & Immunotherapeutics, pp. 2364-2378, vol. 13, No. 10 (2017).
Kapoor et al., "Post-Translational Modifications Optimize the Ability of SARS-CoV-2 Spike for Effective Interaction with Host Cell Receptors", bioRxiv, https://doi.org/10.1101/2021.12.02.470852 (2021).
Karaman et al., "Shape engineering vs organic modification of inorganic nanoparticles as a tool for enhancing cellular internalization", Nanoscale Research Letters, pp. 1-14, vol. 7:358 (2012).
Karjalainen et al., "A Raft-derived, Pak1-regulated Entry Participates in alpha2beta1 Integrin-dependent Sorting to Caveosomes", Molecular Biology of the Cell, pp. 2857-2869, vol. 19, No. 7 (Jul. 2008).
Karlsson et al., "Copper Oxide Nanoparticles Are Highly Toxic: A Comparison between Metal Oxide Nanoparticles and Carbon Nanotubes", Chemical Rsearch in Toxicology, pp. 1726-1732, vol. 21, No. 9 (2008).
Karlsson et al., "Size-dependent toxicity of metal oxide particles—A comparison between nano- and micrometer size", Toxicology Letters, pp. 112-118, vol. 188, Issue 2 (Jul. 24, 2009).
Katsoularis et al., "Risk of acute myocardial infarction and ischaemic stroke following COVID-19 in Sweden: a self-controlled case series and matched cohort study", The Lancet, pp. 599-607, vol. 398, Issue 10300 (Aug. 14, 2021).
Kaur et al., "COVID-19 Vaccine: A comprehensive status report", Virus Research, 198114, in 12 pages, vol. 288 (Oct. 15, 2020).
Kaur et al., "Formulation of Biocompatible Vancomycin Conjugated Gold Nanoparticles for Enhanced Antibacterial Efficacy", 2022, ES Energy & Environment, pp. 34-44, vol. 15 (2022).
Kaur et al., "In vitro studies on radiosensitization effect of glucose capped gold nanoparticles in photon and ion irradiation of HeLa cells", Nuclear Instruments and Methods in Physics Research B, pp. 7-11, vol. 301 (Apr. 2013).
Kayala et al., "Learning to Predict Chemical Reactions", Journal of Chemical Information and Modeling, pp. 2209-2222, vol. 51, Issue 9 (2011).
Kennedy et al., "Evaluation of Folate Conjugate Uptake and Transport by the Choroid Plexus of Mice", Pharmaceutical Research, pp. 714-719, vol. 20 (2003).
Kermi et al., "Regulation of DNA Replication in Early Embryonic Cleavages", Genes, 8, 42 in 21 pages, (2017) doi:10.3390/genes8010042.
Kerr et al., "Apoptosis: a basic biological phenomenon with wide-ranging implications in tissue kinetics", British Journal of Cancer, pp. 239-257, vol. 26, Issue 4 (Aug. 1972).

(56) References Cited

OTHER PUBLICATIONS

Kettiger et al., "Comparative safety evaluation of silica-based particles", Toxicology in Vitro, pp. 355-363, vol. 30, Issue 1, Part B (Dec. 25, 2015).
Khan et al., "Inkjet-Printed Flexible Gold Electrode Arrays for Biolelectronic Interfaces", Advanced Functional Materials, pp. 1004-1013, vol. 26, Issue 7 (Feb. 16, 2016).
Khan et al., "Visualizing in deceased COVID-19 patients how SARS-CoV-2 attacks the respiratory and olfactory mucosae but spares the olfactory bulb", Cell, pp. 5932-5949, vol. 184, Issue 24 (Nov. 24, 2021).
Kim et al., "Development of Spike Receptor-Binding Domain Nanoparticles as a Vaccine Candidate against SARS-CoV-2 Infection in Ferrets", Microbial Pathogenesis, e00230-21, in 13 pages, Research Article, vol. 12, No. 2 (Mar. 2, 2010).
Kim et al., "Effects of COVID-19 on preferences for private dining facilities in restaurants", Journal of Hospitality and Tourism, pp. 67-70, vol. 45 (2020).
Kim et al., "Lethal effect of adriamycin on the division cycle of HeLa cells", Cancer Research, pp. 323-325, vol. 32, Issue 2 (Feb. 1972).
Kim et al., "Post microtextures accelerate cell proliferation and osteogenesis", Acta Biomaterialia, pp. 160-169, vol. 6, Issue 1 (Jan. 2010).
Kim et al., "The Recent Progress in Quantitative Medical Image Analysis for Computer Aided Diagnosis Systems", Healthcare Informatics Research, pp. 143-149, vol. 17, Issue 3 (2011).
Kimbrell, "Governance of nanotechnology and nanomaterials: principles, regulation, and renegotiating the social contract", Journal of Law, Medicine & Ethics, pp. 706-723, vol. 37, Issue 4 (2009).
Kiseleva et al., "COVID-19 Shuts Doors to Flu but Keeps Them Open to Rhinoviruses", Biology,733 in 22 pages, vol. 10 (2021).
Kiss et al., "Structural analysis of respiratory syncytial virus reveals the position of M2-1 between the matrix protein and the ribonucleoprotein complex", Journal of Virology, pp. 7602-7617, vol. 88, No. 13 (Jul. 2014).
Koehler et al., "Defining and managing COVID-19-associated pulmonary aspergillosis: the 2020 ECMM/ISHAM consensus criteria for research and clinical guidance", The Lancet, pp. E149-E162, vol. 21, Issue 6 (Jun. 1, 2021).
Koenig et al., "Structure-guided multivalent nanobodies block SARS-CoV-2 infection and suppress mutational escape", Science, 371, 691 in 17 pages (2021).
Kohyama et al., "Efficient induction of cytotoxic T lymphocytes specific for severe acute respiratory syndrome (SARS)-associated coronavirus by immunization with surface-linked liposomal peptides derived from a non-structural polyprotein 1a", Antiviral Research, pp. 168-177, vol. 84, Issue 2 (Nov. 2009).
Kojima et al., "Protective immunity after recovery from SARS-CoV-2 infection", The Lancet, pp. 12-14, vol. 22, Issue 1 (Jan. 1, 2022).
Koletsas et al., "Thyroid transcription factor-1 expression in invasive and non-invasive urothelial carcinoma", Hippokratia, pp. 154-157, vol. 21 (2017).
Komuro et al., "Inkjet printed (bio)chemical sensing devices", Analytical and Bioanalytical Chemistry, pp. 5785-5805, vol. 405 (2013).
Kong et al., "Enhancement of radiation cytotoxicity in breast-cancer cells by localized attachment of gold nanoparticles", Small, pp. 1537-1543, vol. 4, Issue 9 (2008).
Konno et al., "SARS-CoV-2 ORF3b is a potent interferon antagonist whose activity is further increased by a naturally occurring elongation variant", Cell Reports, vol. 32, Issue 12, pp. 1-16 (2020).
Korber et al., "Tracking Changes in SARS-CoV-2 Spike: Evidence that D614G Increases Infectivity of the COVID-19 Virus", Cell, pp. 812-827, vol. 182, Issue 4 (2020).
Kou et al., "The endocytosis and intracellular fate of nanomedicines: Implication for rational design", Asian Journal of Pharmaceutical Sciences, pp. 1-10, vol. 8, Issue 1 (Feb. 2013).
Krakowiak et al., "Hsf1 and Hsp70 constitute a two-component feedback loop that regulates the yeast heat shock response", Elife, e31668 in 17 pages, vol. 7 (Feb. 2, 2018).
Kramer et al., "In vitro cell migration and invasion assays", Mutation Research/Reviews in Mutation Research, pp. 10-24, vol. 752, Issue 1 (Jan.-Mar. 2013).
Krammer, "SARS-CoV-2 vaccines in development", Nature, pp. 516-527, vol. 586 (2020).
Krause et al., "Rapid Microfluidic Immunoassays of Cancer Biomarker Proteins Using Disposable Inkjet-Printed Gold Nanoparticles Arrays", ChemistryOpen Communications, pp. 141-145, vol. 2, Issue 4 (Aug. 2013).
Kresge et al., "Ordered mesoporous molecular sieves synthesized by a liquid-crystal template mechanism", Nature, pp. 710-712, vol. 359 (1992).
Krile et al., "Forecasting the operational activities of the sea passenger terminal using intelligent technologies", Transport Problems, pp. 27-36, vol. 13, Issue 1 (Mar. 2018).
Kroemer G, et al., "Classification of cell death: recommendations of the Nomenclature Committee on Cell Death 2009", Cell Death & Differentiation, pp. 3-11, vol. 16 (2009).
Krogh et al., "Predicting transmembrane protein topology with a hidden markov model: application to complete genomes", Journal of Molecular Biology, pp. 567-580, vol. 305, Issue 3 (Jan. 19, 2001).
Kroll et al., "Current in vitro methods in nanoparticle risk assessment: Limitations and challenges", pp. 370-377, vol. 72, Issue 2 (Jun. 2009).
Kroll et al., "Cytotoxicity screening of 23 engineered nanomaterials using a test matrix of ten cell lines and three different assays" Particle and Fibre Toxicology, 8:9 in 19 pages (2011).
Krysko et al., "Apoptosis and necrosis: Detection, discrimination and phagocytosis", Methods, pp. 205-221, vol. 44, Issue 3 (Mar. 2008).
Ku et al., "Copper Sulfide Nanoparticles As a New Class of Photoacoustic Contrast Agent for Deep Tissue Imaging at 1064 nm", ACS Nano, pp. 7489-7496, vol. 6, Issue 8 (2012).
Kue et al., "Small Molecules for Active Targeting in Cancer", Medicinal Research Reviews, pp. 494-575, vol. 36, Issue 3 (May 2016).
Kularatne et al., "Targeting of Nanoparticles: Folate Receptor", In: Grobmyer, S., Moudgil, B. (eds) Cancer Nanotechnology. Methods in Molecular Biology, pp. 249-265, vol. 624. Humana Press. https://doi.org/10.1007/978-1-60761-609-2_17.
Kumar et al., "Synthesis and conjugation of ZnO nanoparticles with bovine serum albumin for biological applications", Applied Nanoscience, pp. 141-144, vol. 3 (2013).
Kura et al., "Outbreak of Legionnaires disease on a cruise ship linked to spa-bath filter stones contaminated with Legionella pneumophila serogroup 5", Epidemiology & Infection, pp. 385-391, vol. 134 (2006).
Kuster et al., "SARS-CoV2: should inhibitors of the renin-angiotensin system be withdrawn in patients with COVID-19?" European Heart Journal, pp. 1801-1803, vol. 41 (May 14, 2020).
Kuthati et al., "Functionalization of mesoporous silica nanoparticles for targeting, biocompatibility, combined cancer therapies and theragnosis", Journal of Nanoscience and Nanotechnology, pp. 2399-2430, vol. 13 (2013).
Kwon et al., "Silica-based mesoporous nanoparticles for controlled drug delivery", Journal of Tissue Engineering, First Published Sep. 3, 2013, Research Article, https://doi: 10.1177/2041731413503357.
Kyte et al., "A simple method for displaying the hydropathic character of a protein", Journal of Molecular Biology, pp. 105-132, vol. 157, Issue 1 (May 5, 1982).
Lam et al., "SARS-CoV-2 spike protein predicted to form complexes with host receptor protein orthologues from a broad range of mammals", Scientific Reports, Article No. 16471, in 14 pages, vol. 10 (2020).
Lamas-Barreiro et al., "Angiotensin II suppression in SARS-CoV-2 infection: a therapeutic approach", Nefrologia (Engl Ed). May-Jun. 2020;40(3):213-216. English, Spanish. doi: 10.1016/j.nefro.2020.04.006. Epub Apr. 30, 2020. PMID: 32456945; PMCID: PMC7190491.

(56) References Cited

OTHER PUBLICATIONS

Landry et al., "Tumor-stroma interactions differentially alter drug sensitivity based on the origin of stromal cells", Molecular Systems Biology, e8322 in 15 pages, vol. 14, Issue 8, (Aug. 1, 2018).
Lane, "The unseen world: reflections on Leeuwenhoek (1677) 'Concerning little animals'", Philosophical Transactions of the Royal Society B, vol. 370, Issue 1666 (Apr. 19, 2015).
Långstedt et al., "Customer perceptions of COVID-19 countermeasures on passenger ships during the pandemic", Transportation Research Interdisciplinary Perspectives, 1005182, vol. 13 (2022).
Larsen et al., "Large-scale validation of methods for cytotoxic T-lymphocyte epitope prediction", BMC Bioinformatics, in 12 pages, 8:424 (2007).
Larsen et al., "Modeling the Onset of Symptoms of COVID-19", Frontiers in Public Health, Article 473 in 14 pages, vol. 8 (Aug. 13, 2020).
Lauster et al., "Phage capsid nanoparticles with defined ligand arrangement block influenza virus entry", Nature Nanotechnology, pp. 373-379, vol. 15 (2020).
Lawanprasert et al., "Inhalable SARS-CoV-2 Mimetic Particles Induce Pleiotropic Antigen Presentation", Biomacromolecules, pp. 1158-1168, vol. 23 (2022).
Le Bourhis, "Glass—Mechanics and Technology, 2nd Edition", in 30 pgs., Wiley-VCH, Weinheim, Germany (2008) ISBN: 978-3-527-31549-9.
Leak, "Heat shock proteins in neurodegenerative disorders and aging", Journal of Cell Communication and Signaling, pp. 293-310, vol. 8 (2014).
Leamon et al., "Folate-mediated targeting: from diagnostics to drug and gene delivery", Drug Discovery Today, pp. 44-51, vol. 6, Issue 1 (Jan. 1, 2001).
Leamon et al., "Folate-targeted chemotherapy", Advanced Drug Delivery Reviews, pp. 1127-1141, vol. 56, Issue 8 (Apr. 29, 2004).
Ledford, "'Killer' Immune Cells Still Recognize Omicron Variant", Nature, p. 307, vol. 601 (Jan. 20, 2022).
Lee et al., "Multiscale modeling of dendrimers and their interactions with bilayers and polyelectrolytes", Molecules, pp. 423-438, vol. 14 (2009).
Lee et al., "Oncogenes and Tumor Suppressor Genes", Cold Spring Harbor Perspectives in Biology, 2010, 2(10): a003236.
Lee et al., "Three-Dimensional Cell Culture Matrices: State of the Art", Tissue Engineering Part B: Reviews, pp. 61-86, vol. 14, Issue 1 (Mar. 10, 2008).
Lee et al., "Uniform mesoporous dye-doped silica nanoparticles decorated with multiple magnetite nanocrystals for simultaneous enhanced magnetic resonance imaging, fluorescence imaging, and drug delivery", Journal of the American Chemical Society, pp. 552-557, vol. 132 (2010).
Lehnert et al., "Cell behaviour on micropatterned substrata: limits of extracellular matrix geometry for spreading and adhesion", Journal of Cell Science, pp. 41-52, vol. 117 Part 1 (Jan. 1, 2004).
Leong et al., "On the issue of transparency and reproducibility in nanomedicine", Nature Nanotechnology, pp. 629-635, vol. 14 (2019).
Lerman et al., "The Evolution of Polystyrene as a Cell Culture Material", Tissue Engineering Part B, pp. 359-372, vol. 24 (2018).
Letko et al., "Functional assessment of cell entry and receptor usage for SARS-CoV-2 and other lineage B betacoronaviruses", Nature Microbiology, pp. 562-569, vol. 5 (2020).
Levin et al., "Waning Immune Humoral Response to BNT162b2 Covid-19 Vaccine over 6 Months", New England Journal of Medicine, pp. E84(1)-e84(11), vol. 385:24 (Dec. 9, 2021).
Li et al., "A synthetic nanobody targeting RBD protects hamsters from SARS-CoV-2 infection", Article No. 4635, vol. 12 (2021).
Li et al., "Activation of topoisomerase II-mediated excision of chromosomal DNA loops during oxidative stress", Genes & Development, pp. 1553-1560, vol. 13 (1999).
Li et al., "Antitumor activity of celastrol nanoparticles in a xenograft retinoblastoma tumor mode", International Journal of Nanomedicine, pp. 2389-2398, vol. 7 (2012).
Li et al., "Association of Renin-Angiotensin System Inhibitors With Severity or Risk of Death in Patients With Hypertension Hospitalized for Coronavirus Disease 2019 (COVID-19) Infection in Wuhan, China", JAMA Cardiology, pp. 825-830, vol. 5 (2020).
Li et al., "Cell-mimicking nanodecoys neutralize SARS-CoV-2 and mitigate lung injury in a non-human primate model of COVID-19" Nature Nanotechnology, pp. 942-951, vol. 16 (Aug. 2021).
Li et al., "Copper sulfide nanoparticles for photothermal ablation of tumor cells", Nanomedicine, pp. 1161-1171, vol. 5 (2010).
Li et al., "Epitope-based peptide vaccines predicted against novel coronavirus disease caused by SARS-CoV-2", Virus Research, 198082, vol. 288 (Oct. 15, 2020).
Li et al., "Glucose-Conjugated Chitosan Nanoparticles for Targeted Drug Delivery and Their Specific Interaction with Tumor Cells", Frontiers of Materials Sciences, pp. 363-372, vol. 8 (Dec. 2014).
Li et al., "Inkjet printing for biosensor fabrication: combining chemistry and technology for advanced manufacturing", Lab on a Chip, pp. 2538-2558, vol. 15 (2015).
Li et al., "The Horizon of Materiobiology: A Perspective on Material-Guided Cell Behaviors and Tissue Engineering", Chemical Reviews. pp. 4376-4421, vol. 117 (2017).
Li et al., "The MERS-CoV Receptor DPP4 as a Candidate Binding Target of the SARS-CoV-2 Spike", iScience, 101160, vol. 23, Issue 6 (Jun. 26, 2020).
Li et al., "Transmission Routes Analysis of SARS-CoV-2: A Systematic Review and Case Report", . Frontiers in Cell and Developmental Biology, vol. 8, Article 618 (Jul. 2020).
Liang et al., "Pulmonary Delivery of Biological Drugs", Pharmaceutics, 2020, 12(11):1025. https://doi.org/10.3390/pharmaceutics12111025.
Liao et al., "Interactions of Zinc Oxide Nanostructures with Mammalian Cells: Cytotoxicity and Photocatalytic Toxicity", International Journal of Molecular Sciences, 21 (17):6305 (2020) doi: 10.3390/ijms21176305.
Liberti et al., "The Warburg Effect: How Does it Benefit Cancer Cells?" Trends in Biochemical Sciences, Opinion Special Issue: Mitochondria & Metabolism, pp. 211-218, vol. 41, Issue 3 (2016).
Lidén, "The European Commission Tries to Define Nanomaterials", Annals of Occupational Hygiene, pp. 1-5, vol. 55 (2011).
Lin et al., "Celastrol Inhibits Dopaminergic Neuronal Death of Parkinson's Disease through Activating Mitophagy", Antioxidants, (Basel), Dec. 31, 2019, 9(1):37. doi: 10.3390/antiox9010037.
Lin et al., "Association of HLA class I with severe acute respiratory syndrome coronavirus infection", BMC Medical Genetics, pp. 1-7, 4:9 (2003).
Liong et al., "Multifunctional Inorganic Nanoparticles for Imaging, Targeting, and Drug Delivery", ACS Nano, pp. 889-896, vol. 2 (2008).
Liu et al., "A Versatile and Robust Microfluidic Platform Toward High Throughput Synthesis of Homogeneous Nanoparticles with Tunable Properties", Advanced Materials, pp. 2298-2304, vol. 27 (2015) https://doi.org/10.1002/adma.201405408.
Liu et al., "Aerodynamic analysis of SARS-CoV-2 in two Wuhan hospitals", Nature, pp. 557-560, vol. 582 (2020).
Liu et al., "An emergency responding mechanism for cruise epidemic prevention-taking COVID-19 as an example", Marine Policy, 2020, 119:104093. doi: 10.1016/j.marpol.2020.104093.
Liu et al., "Anti-hypertensive Angiotensin II receptor blockers associated to mitigation of disease severity in elderly COVID-19 patients", 2020, medRxiv, doi: https://doi.org/10.1101/2020.03.20.20039586.
Liu et al., "Atomic structure of a rhinovirus C, a virus species linked to severe childhood asthma", Proceedings of the National Academy of Sciences of the United States of America, pp. 8997-9002, vol. 113, No. 32 (Jul. 11, 2016).
Liu et al., "Potential inhibitors against 2019-nCoV coronavirus M protease from clinically approved medicines", Journal of Genetics and Genomics, pp. 119-121, vol. 47 (2020).
Liu et al., "Renal clearable inorganic nanoparticles: a new frontier of bionanotechnology", Materials Today, pp. 477-486, vol. 16, Issue 12 (Dec. 2013).

(56) References Cited

OTHER PUBLICATIONS

Liu et al., "Structural insights into the binding of hepatitis B virus core peptide to HLA-A2 alleles: Towards designing better vaccines", European Journal of Immunology, pp. 2097-2106, vol. 41 (2011).

Liu et al., "The Main Anticancer Bullets of the Chinese Medicinal Herb, Thunder God Vine", Molecules, pp. 5283-5297, vol. 16 (2011).

Liu et al., "Tourism crisis management: Can the Extended Parallel Process Model be used to understand crisis responses in the cruise industry?", Tourism Management, pp. 310-321, vol. 55 (Aug. 2016).

Liu et al., "Two-Step Self-Assembly of Hierarchically-Ordered Nanostructures", Journal of Materials Chemistry A, pp. 11688-11699, vol. 3, Issue 22 (2015).

Liu et al., "Vimentin contributes to epithelial-mesenchymal transition cancer cell mechanics by mediating cytoskeletal organization and focal adhesion maturation", Oncotarget, pp. 15966-15983, vol. 6 (2018).

Liu, "The history of monoclonal antibody development—Progress, remaining challenges and future innovations", Annals of Medicine and Surgery, pp. 113-116, vol. 3, Issue 4 (Dec. 2014).

Locasale et al., "Altered metabolism in cancer", BMC Biology, Article No. 88 (2010).

Lokman et al., "Chick chorioallantoic membrane (CAM) assay as an in vivo model to study the effect of newly identified molecules on ovarian cancer invasion and metastasis", International Journal of Molecular Sciences, pp. 9959-9970, vol. 13 (2012).

London et al., "Rosetta FlexPepDock web server—High resolution modeling of peptide-protein interactions", Nucleic Acids Research, W249-W253, vol. 39 (2011).

López-Alonso et al., "Carbodiimide EDC Induces Cross-Links That Stabilize RNase A C-Dimer against Dissociation: EDC Adducts Can Affect Protein Net Charge, Conformation, and Activity", Bioconjugate Chemistry, pp. 1459-1473, vol. 20 (2009).

López-Sagaseta et al., "Self-assembling protein nanoparticles in the design of vaccines", Computational and Structural Biotechnology Journal, pp. 58-68, vol. 14 (2015).

Loveridge et al., "The Sphingosine Kinase 1 Inhibitor 2-(p-hydroxyanilino)-4-(p-chlorophenyl)thiazole Induces Proteasomal Degradation of Sphingosine Kinase 1 in Mammalian Cells", Journal of Biological Chemistry, Signal Transduction, pp. 38841-38852, vol. 285, Issue 50 (Dec. 2010).

Lu et al., "COVID-19 Outbreak Associated with Air Conditioning in Restaurant, Guangzhou, China, 2020", Emerging Infectious Diseases, pp. 1628-1631, vol. 26 (2020).

Lu et al., "Size Effect on Cell Uptake in Well-Suspended, Uniform Mesoporous Silica Nanoparticles", Small, pp. 1408-1413, vol. 5 (2009).

Lucas et al., "Protein deposition from dry powder inhalers: fine particle multiplets as performance modifiers", Pharmaceutical Research, pp. 562-569, vol. 15 (1998).

Lund et al., "Definition of supertypes for HLA molecules using clustering of specificity matrices", Immunogenetics, pp. 797-810, vol. 55 (2004).

Lunenfeld et al., "The clinical consequences of an ageing world and preventive strategies", Best Practice & Research Clinical Obstetrics & Gynaecology, pp. 643-659, vol. 27, Issue 5 (Oct. 2013).

Luu et al., "Pannexin-1 channel opening is critical for COVID-19 pathogenesis", iScience, Dec. 17, 2021, 24(12):103478.

Lyngse et al., "SARS-CoV-2 Omicron VOC Transmission in Danish Households", medRxiv, 2021, 12.27 21268278; doi: https://doi.org/10.1101/2021.12.27.21268278.

Maacha et al., "Evaluation of Tumor Cell Invasiveness In Vivo: The Chick Chorioallantoic membrane Assay", Methods in Molecular Biology, pp. 71-77, vol. 1749 (2018).

Määttänen et al., "A low-cost paper-based inkjet-printed platform for electrochemical analyses", Sensors and Actuators B: Chemical, pp. 153-162, vol. 177 (2013).

Määttänen et al., "Hierarchically structured self-supported latex films for flexible and semi-transparent electronics", Applied Surface Science, pp. 37-44, vol. 364 (2016).

Määttänen et al., "Printed paper-based arrays as substrates for biofilm formation" AMB Express, pp. 32-44, vol. 4, Article No. 32 (2014).

Mafham et al., "What is the association of COVID-19 with heart attacks and strokes?", The Lancet, pp. 561-563, vol. 398, Issue 10300 (2021).

Maghsoodi, "Role of Solvents in Improvement of Dissolution Rate of Drugs: Crystal Habit and Crystal Agglomeration", Advanced Pharmaceutical Bulletin, pp. 13-18, vol. 5, Issue 1 (2015).

Maier et al., "ff14SB: Improving the Accuracy of Protein Side Chain and Backbone Parameters from ff99SB", Journal of Chemical Theory and Computation, pp. 3696-3713, vol. 11, Issue 8 (2015).

Mainzer, "Interdisciplinarity and innovation dynamics. On convergence of research, technology, economy, and society", Poiesis & Praxis, pp. 275-289, vol. 7 (2011).

Mäkelä et al., "Intranasal inhibitor blocks Omicron and other variants of SARS-CoV-2", bioRxiv, 2021, 12.28 474326; doi: https://doi.org/10.1101/2021.12.28.474326.

Malhotra et al., "Classical chemotherapy: mechanisms, toxicities and the therapeutic window", Cancer Biology & Therapy, pp. 1-3, vol. 2, Suppl. 1 (Published online: Mar. 1, 2003).

Mallapaty, "Antibody tests suggest that coronavirus infections vastly exceed official counts", Nature, Apr. 17, 2020; Update Apr. 19, 2020; Correction Apr. 22, 2020, doi: https://doi.org/10.1038/d41586-020-01095-0.

Mamaeva et al., "Inhibiting Notch Activity in Breast Cancer Stem Cells by Glucose Functionalized Nanoparticles Carrying γ-secretase Inhibitors", Molecular Therapy, pp. 926-936, vol. 24, Issue 5 (2016).

Mamaeva et al., "Mesoporous silica nanoparticles as drug delivery systems for targeted inhibition of Notch signaling in cancer", Molecular Therapy, pp. 1538-1546, vol. 19, Issue 8 (2011).

Maponga et al., "Persistent SARS-CoV-2 Infection with Accumulation of Mutations in a Patient with Poorly Controlled HIV Infection" in 12 pages, (PostedJan. 21, 2022) Available at SSRN: https://ssrn.com/abstract=4014499 or http://dx.doi.org/10.2139/ssrn.4014499.

Marcussen, "Visualizing the network of cruise destinations in the Baltic Sea—a multidimensional scaling approach", Scandinavian Journal of Hospitality and Tourism, pp. 1-15, vol. 17 (2016).

Marrison et al., "Ptychography—a label free, high-contrast imaging technique for live cells using quantitative phase information", Scientific Reports, vol. 3, Article No. 2369, in 7 pages (2013).

Martin et al., "Surface Functionalization of Nanomaterials with Dendritic Groups: Toward Enhanced Binding to Biological Targets" Journal of the American Chemical Society, pp. 734-741, vol. 131 (2009).

Martinez et al., "Diagnostics for the Developing World: Microfluidic Paper-Based Analytical Devices", Analytical Chemistry, pp. 3-10, vol. 82 (2010).

Mary et al., "Rationale for COVID-19 Treatment by Nebulized Interferon-β-1b-Literature Review and Personal Preliminary Experience", Frontiers in Pharmacology, Hypothesis and Theory Article (Nov. 30, 2020) doi: 10.3389/fphar.2020.592543.

Matsumura et al., "A new concept for macromolecular therapeutics in cancer chemotherapy: mechanism of tumoritropic accumulation of proteins and the antitumor agent smancs", Cancer Research, pp. 6387-6392, vol. 46 (1986).

Mayer et al., "Hsp70 chaperones: Cellular functions and molecular mechanism", Cellular and Molecular Life Sciences, pp. 670-684, vol. 62 (2005).

Maynard, "Don't define nanomaterials", Nature, p. 31, vol. 475 (Jul. 7, 2011).

Mazzu-Nascimento et al., "Towards low-cost bioanalytical tools for sarcosine assays for diagnostics", Analytical Methods, pp. 7312-7318, vol. 8 (2016).

McCallum et al., "SARS-CoV-2 immune evasion by the B.1.427/B.1.429 variant of concern", Science, pp. 648-654, vol. 373 (2021).

(56) References Cited

OTHER PUBLICATIONS

McCallum et al., "Structure-guided covalent stabilization of coronavirus spike glycoprotein trimers in the closed conformation", Nature Structural & Molecular Biology, pp. 942-949, vol. 27 (2020).

McCraw et al., "Structural analysis of influenza vaccine virus-like particles reveals a multicomponent organization", Scientific Reports, Article No. 10342 vol. 8 (2018).

McKechnie et al., "The Innate Immune System: Fighting on the Front Lines or Fanning the Flames of COVID-19?" Cell Host & Microbe, pp. 863-869, vol. 27 (2020).

McLachlan, "The angiotensin-converting enzyme 2 (ACE2) receptor in the prevention and treatment of COVID-19 are distinctly different paradigms", Clinical Hypertenion, in 3 pages, 26:14 (2020).

McNerney, "Diagnostics for Developing Countries", Diagnostics, pp. 200-209, vol. 5 (2015).

Medhi et al., "Nanoparticle-Based Strategies to Combat COVID-19", ACS Applied Nano Materials, pp. 8557-8580, vol. 3 (2020).

Meijerman et al., "Combined action and regulation of phase II enzymes and multidrug resistance proteins in multidrug resistance in cancer", Cancer Treatment Reviews, pp. 505-520, vol. 34 (2008).

Mendillo et al., "HSF1 Drives a Transcriptional Program Distinct from Heat Shock to Support Highly Malignant Human Cancers", Cell, pp. 549-562, vol. 150, Issue 3 (2012).

Meng et al., "Renin-angiotensin system inhibitors improve the clinical outcomes of COVID-19 patients with hypertension", Emerging Microbes & Infections, pp. 757-760, vol. 9, Issue 1 (2020).

Merad et al., "Pathological inflammation in patients with COVID-19: a key role for monocytes and macrophages", Nature Reviews Immunology, pp. 355-362, vol. 20 (2020).

Micheau et al., "NF-kappaB signals induce the expression of c-FLIP", Molecular and Cellular Biology, pp. 5299-5305, vol. 21, No. 16 (2001).

Migliorini et al., "Association between HLA genotypes and COVID-19 susceptibility, severity and progression: a comprehensive review of the literature", European Journal of Medical Research, 26(1):84, in 9 pages (2021).

Miller et al., "c-Myc and cancer metabolism", Clinical Cancer Research, pp. 5546-5553, vol. 18 (2012).

Miller et al., "Risk factors for metastatic disease at presentation with osteosarcoma: an analysis of the SEER database", The Journal of Bone and Joint Surgery, in 8 pages, 95(13):e89 (2013).

Moghaddam et al., "Enhanced Cellular Uptake of Nanoparticles by Increasing the Hydrophobicity of Poly(lactic Acid) through Copolymerization with Cell-Membrane-Lipid Components", Chemical Communications, pp. 14605-14608, vol. 51, Issue 78 (2015).

Monsé et al., "Concentration-dependent systemic response after inhalation of nano-sized zinc oxide particles in human volunteers", Particle and Fibre Toxicology, in 11 pages (2018) https://doi.org/10.1186/S12989-018-0246-4.

Monteil et al., "Inhibition of SARS-CoV-2 Infections in Engineered Human Tissues Using Clinical-Grade Soluble Human ACE2", Cell, pp. 905-913, vol. 181, Issue 4 (2020).

Moore et al., "Vaccination and non-pharmaceutical interventions for COVID-19: a mathematical modelling study", The Lancet, pp. 793-802, vol. 21, Issue 6 (2021).

Morand et al., "Biodiversity and COVID-19: A report and a long road ahead to avoid another pandemic", One Earth, pp. 920-923, vol. 4 (2021).

Morawaska et al., "How can airborne transmission of COVID-19 indoors be minimised?", Environment International, 105832, in 7 pages, vol. 142 (Sep. 2020).

Morimoto, "Regulation of the heat shock transcriptional response: cross talk between a family of heat shock factors, molecular chaperones, and negative regulators", Genes and Development, pp. 3788-3796, vol. 12 (1998).

Mortera et al., "Cell-induced intracellular controlled release of membrane impermeable cysteine from a mesoporous silica nanoparticle-based drug delivery system", Chemical Communications, pp. 3219-3221, Issue 22 (2009).

Mosadegh et al., "Three-dimensional model for cardiac ischemia", Advanced Healthcare Materials, pp. 1036-1043, vol. 3, Issue 7 (Jul. 2014).

Moubarak et al., "The death receptor antagonist FLIP-L interacts with Trk and is necessary for neurite outgrowth induced by neurotrophins", The Journal of Neuroscience, pp. 6094-6105, vol. 30(17) (Apr. 28, 2010).

Moulahoum et al., "How should diagnostic kits development adapt quickly in COVID 19-like pandemic models? Pros and cons of sensory platforms used in COVID-19 sensing", Talanta, 121534, in 11 pages, vol. 222 (2021).

Muhsin et al., "Effects of Chemical Conjugation of I-Leucine to Chitosan on Dispersibility and Controlled Release of Drug from a Nanoparticulate Dry Powder Inhaler Formulation", Molecular Pharmaceutics, pp. 1455-1466, vol. 13 (2016).

Muller et al., "The determination and interpretation of the therapeutic index in drug development" Nature Reviews Drug Discovery, pp. 751-761, vol. 11 (2012).

Mulpuru et al., "Immunoinformatic based identification of cytotoxic T lymphocyte epitopes from the Indian isolate of SARS-CoV-2", Scientific Reports, 11:4516, in 9 pages (2021).

Muralidharan et al., "Inhalable nanoparticulate powders for respiratory delivery", Nanomedicine: Nanotechnology, Biology and Medicine, pp. 1189-1199, vol. 11, Issue 5 (Jul. 2015).

Murrell et al., "Forcing cells into shape: the mechanics of actomysin contractility", Nature Reviews Molecular Cell Biology, pp. 486-498, vol. 16 (2015).

Myers, "Why bioimage informatics matters", Nature Methods, pp. 659-660, 9:7 (Jun. 28, 2012).

Nagase et al., "Apoptosis Induction in HL-60 cells and Inhibition of Topoisomerase II by Triterpene Celastrol", Bioscience Biotechnology Biochemistry, pp. 1883-1887, vol. 67, Issue 9 (2003).

Nagata, "Apoptosis and Clearance of Apoptotic Cells", Annual Review of Immunology, pp. 489-517, vol. 36 (2018).

Nakajima et al., "Mechanism of Amide Formation by Carbodiimide for Bioconjugation in Aqueous Media", Bioconjugate Chemistry, pp. 123-130, vol. 6 (1995).

Nakamura et al., "Direct synthesis of monodispersed thiol-functionalized nanoporous silica spheres and their application to a colloidal crystal embedded with gold nanoparticles" Journal of Materials Chemistry, pp. 3726-3732, Issue 35 (2007).

Nakanishi et al., "Genetic instability in cancer cells by impaired cell cycle checkpoints", Cancer Science, pp. 984-989, vol. 97, Issue 10 (Oct. 2006).

Nam et al., "Cellular uptake mechanism and intracellular fate of hydrophobically modified glycol chitosan nanoparticles", Journal of Controlled Release, pp. 259-267, vol. 135, Issue 3 (May 5, 2009).

Narni-Mancinelli et al., "Clues that natural killer cells help to control COVID", Nature, pp. 226-227, vol. 600 (Dec. 9, 2021).

Nasr et al., "PAMAM dendrimers as aerosol drug nanocarriers for pulmonary delivery via nebulization", International Journal of Pharmaceutics, pp. 242-250, vol. 461, Issues 1-2 (Jan. 30, 2014).

Nature Methods, "The quest for quantitative microscopy", p. 627, vol. 9, No. 7 (Jul. 2012).

Nature, "COVID research: a year of scientific milestones", doi: https://doi.org/10.1038/d41586-020-00502-w (May 5, 2021).

Negahdaripour et al., "Harnessing self-assembled peptide nanoparticles in epitope vaccine design", Biotechnology Advances, pp. 575-596, vol. 35 (2017).

Neufurth et al., "The inorganic polymer, polyphosphate, blocks binding of SARS-CoV-2 spike protein to ACE2 receptor at physiological concentrations", Biochemical Pharmacology, 114215 in 10 pages, vol. 182 (Dec. 2020).

Ng et al., "Immunogenetics in SARS: A case-control study", Hong Kong Medical Journal, pp. 29-33, vol. 16, No. 5, Supplement 4 (Oct. 2010).

Ng et al., "Memory T cell responses targeting the SARS coronavirus persist up to 11 years post-infection", Vaccine, pp. 2008-2014, vol. 34, Issue 17 (Apr. 12, 2016).

Ng et al., "Paper-based cell culture platform and its emerging biomedical applications", Materials Today, pp. 32-44, vol. 20, Issue 1 (Jan.-Feb. 2017).

(56) References Cited

OTHER PUBLICATIONS

Nguyen et al., "Protein-based antigen presentation platforms for nanoparticle vaccines", NPJ Vaccines, vol. 6, Article No. 70 (2021).
Nguyen et al., "Diagnosis and Treatment of Patients with Thyroid Cancer", American Health & Drug Benefits, pp. 30-40, vol. 8, No. 1 (Feb. 2015).
Nguyen et al., "Human Leukocyte Antigen Susceptibility Map for Severe Acute Respiratory Syndrome Coronavirus 2", Journal of Virology, e00510-20 in 12 pages, vol. 94, Issue 13 (Jul. 2020).
Nguyen et al., "Metastasis: from dissemination to organ-specific colonization", Nature Reviews Cancer, pp. 274-284, vol. 9 (2009).
Nicoletti et al., "A rapid and simple method for measuring thymocyte apoptosis by propidium iodide staining and flow cytometry", Journal of Immunological Methods, pp. 271-279, vol. 139, Issue 2 (Jun. 3, 1991).
Niemelä et al., "Managing passenger flows for seaborne transportation during COVID-19 pandemic", Journal of Travel Medicine, pp. 1-4, vol. 28, 7 (2021).
Niemelä et al., "Nanoparticles carrying fingolimod and methotrexate enables targeted induction of apoptosis and immobilization of invasive thyroid cancer", European Journal of Pharmaceutics and Biopharmaceutics, pp. 1-9, vol. 148 (Mar. 2020).
Niemelä et al., "Quantitative bioimage analytics enables measurement of targeted cellular stress response induced by celastrol-loaded nanoparticles", Cell Stress and Chaperones, pp. 735-748, vol. 24 (2019).
Niemelä et al., "Sugar-decorated mesoporous silica nanoparticles as delivery vehicles for the poorly soluble drug celastrol enables targeted induction of apoptosis in cancer cells", European Journal of Pharmaceutics and Biopharmaceutics, pp. 11-21, vol. 96 (Oct. 2015).
Niemelä, "Nanoparticles as Targeting System for Cancer Treatment : From idea towards reality", in 112 pages (2019) https://urn.fi/URN:ISBN:978-952-12-3855-0.
Nishiura, "Backcalculating the Incidence of Infection with COVID-19 on the Diamond Princess", Journal of Clinical Medicine, 657 in 4 page, vol. 9 (2020).
Nogrady, "How Kids' Immune System Can Evade COVID", Nature, p. 382, vol. 588 (Dec. 17, 2020).
Nowak-Sliwinska et al., "The chicken chorioallantoic membrane model in biology, medicine and bioengineering", Angiogenesis, pp. 779-804, vol. 17 (2014).
Oates et al., "Role of Titanium Surface Topography and Surface Wettability on Focal Adhesion Kinase Mediated Signaling in Fibroblasts", Materials, pp. 893-907—vol. 4 (2011).
O'Brien et al., "Mortality within 30 days of chemotherapy: a clinical governance benchmarking issue for oncology patients", British Journal of Cancer, pp. 1632-1636, vol. 95 (2006).
Oh et al., "Endocytosis and exocytosis of nanoparticles in mammalian cells", International Journal of Nanomedicine, pp. 51-63, vol. 9, Supplement I (2014).
Oheim, "High-throughput microscopy must reinvent the microscope rather than speed up its functions", British Journal of Pharmacology, pp. 1-4, vol. 152 (2007).
Orkhan et al., "RBD and ACE2 Embedded Chitosan Nanoparticles as a Prevention Approach for SARS-COV 2", 2Biomedical Journal of Scientific & Technical Research, pp. 29193-29197 (2021) ISSN: 2574-1241, DOI: 10.26717/BJSTR.2021.37.005960.
Orrenius et al., "Cell Death Mechanisms and Their Implications in Toxicology", Toxicological Sciences, pp. 3-19, vol. 119, Issue 1 (Jan. 2011).
O'Shannessy et al., "Expression of folate receptors alpha and beta in normal and cancerous gynecologic tissues: correlation of expression of the beta isoform with macrophage markers", Journal of Ovarian Research, in 9 pages, vol. 8 (2015).
Ossowski et al., "Experimental model for quantitative study of metastasis", Cancer research, pp. 2300-2309, vol. 40 (1980).
Ou et al., "Emergence of SARS-CoV-2 spike RBD mutants that enhance viral infectivity through increased human ACE2 receptor binding affinity", bioRxiv preprint doi: https://doi.org/10.1101/2020.03.15.991844.
Ou et al., "V367F mutation in SARS-CoV-2 spike RBD emerging during the early transmission phase enhances viral infectivity through increased human ACE2 receptor binding affinity", bioRxiv 2020.03.15.991844; doi: https://doi.org/10.1101/2020.03.15.991844.
Outlaw et al., "Inhibition of Coronavirus Entry In Vitro and Ex Vivo by a Lipid-Conjugated Peptide Derived from the SARS-CoV-2 Spike Glycoprotein HRC Domain", ASM Journals, mBio, e01935-20, in 14 pages, vol. 11, Issue 5 (Sep./Oct. 2020).
Owens et al., "Opsonization, biodistribution, and pharmacokinetics of polymeric nanoparticles", International Journal of Pharmaceutics, pp. 93-102, vol. 307, Issue 1 (Jan. 3, 2006).
Oxtoby et al., "Imaging plus X: multimodal models of neurodegenerative disease", Current Opinion in Neurology, pp. 371-379, vol. 30 (2017).
Ozaki et al., "Role of p53 in Cell Death and Human Cancers", Cancers, pp. 994-1013, vol. 3 (2011).
Paaby et al., "The many faces of pleiotropy", Trends in Genetics, pp. 66-73, vol. 29, Issue 2 (Feb. 1, 2013).
Paatero et al., "Analyses in zebrafish embryos reveal that nanotoxicity profiles are dependent on surface-functionalization controlled penetrance of biological membranes", Scientific Reports, in 13 pages, vol. 7, Article No. 8423 (2017).
Pace et al., "Zinc-binding cysteines: diverse functions and structural motifs", Biomolecules, pp. 419-434, vol. 4 (2014).
Padma, "An overview of targeted cancer therapy", BioMedicine, pp. 1-6, vol. 5, No. 4, Article 1 (Dec. 2015).
Palika et al., "An antiviral trap made of protein nanofibrils and iron oxyhydroxide nanoparticles", Nature Nanotechnology, pp. 918-925, vol. 16 (Aug. 2021).
Pallavicini et al., "Self-assembled monolayers of gold nanostars: a convenient tool for Near-IR photothermal biofilm eradication", Chemical Communications, pp. 1969-1971, Issue 16 (2014).
Palumbo et al., "Systemic cancer therapy: achievements and challenges that lie ahead", Frontiers in Pharmacology, pp. 1-9, vol. 4, Article 57 (May 2013).
Pan et al., "Perceptions of cruise travel during the COVID-19 pandemic: Market recovery strategies for cruise businesses in North America", Tourism Management, 104275, in 11 pages, vol. 85 (2021).
Panchariya et al., "Zinc2+ ion inhibits SARS-CoV-2 main protease and viral replication in vitro", bioRxiv 2021.06.15.448551; doi: https://doi.org/10.1101/2021.06.15.448551, https://www.biorxiv.org/content/10.1101/2021.06.15.448551v1.
Papaccio et al., "Concise Review: Cancer Cells, Cancer Stem Cells, and Mesenchymal Stem Cells: Influence in Cancer Development", Stem Cells Translational Medicine, pp. 2115-2125, vol. 6 (2017).
Papathanassis, "The growth and development of the cruise sector: A perspective article", Tourism Review, pp. 130-135, 75(1) (2019) doi: 10.1108/TR-02-2019-0037.
Papp et al., "Inhibition of Influenza Virus Infection by Multivalent Sialic-Acid-Functionalized Gold Nanoparticles", Small, pp. 2900-2906, vol. 6, Issue 24 (Dec. 2010).
Park et al., "Immunogenicity and protective efficacy of an intranasal live-attenuated vaccine against SARS-CoV-2", iScience, 102941 in 27 pages, vol. 24, Issue 9 (Sep. 24, 2021).
Park et al., "Pharmacokinetics and biodistribution of recently-developed siRNA nanomedicines", Advanced Drug Delivery Reviews, pp. 93-109, vol. 104 (Sep. 1, 2016).
Park et al., "Self-assembled nanoplatform for targeted delivery of chemotherapy agents via affinity-regulated molecular interactions", Biomaterials, pp. 7766-7775, vol. 31, Issue 30 (Oct. 2010).
Parker et al., "Folate receptor expression in carcinomas and normal tissues determined by a quantitative radioligand binding assay", Analytical Biochemistry, pp. 284-293, vol. 338, Issue 2 (Mar. 2005).
Paulos et al., "Ligand binding and kinetics of folate receptor recycling in vivo: impact on receptor-mediated drug delivery", Molecular Pharmacology, pp. 1406-1414, vol. 66, Issue 6 (Dec. 1, 2004).

(56) References Cited

OTHER PUBLICATIONS

Pedersen et al., "Solid lipid nanoparticles can effectively bind DNA, streptavidin and biotinylated ligands", European Journal of Pharmaceutics and Biopharmaceutics, pp. 155-162, vol. 62, Issue 2 (Feb. 2006).
Peng et al., "[Clinical characteristics and outcomes of 112 cardiovascular disease patients infected by 2019-nCoV]", Zhonghua Xin Xue Guan Bing Za Zhi. 48(0):E004.
Peng et al., "HSP90 inhibitor, celastrol, arrests human monocytic leukemia cell U937 at G0/G1 in thiol-containing agents reversible way", Molecular Cancer, in 13 pages, 9:79 (2010) doi:10.1186/1476-4598-9-79.
Pennington-Gray, "Reflections to move forward: Where destination crisis management research needs to go", Tourism Management Perspectives, pp. 136-139, vol. 25 (2018).
Pernet, "Null hypothesis significance testing: a short tutorial", F1000Res, 2004, 4:621. doi: 10.12688/f1000research.6963.3.
Perreault et al., "Different toxicity mechanisms between bare and polymer-coated copper oxide nanoparticles in Lemna gibba", Environmental Pollution, pp. 219-227, vol. 185 (Feb. 2014).
Pessi et al., "Controlled Expansion of Supercritical Solution: A Robust Method to Produce Pure Drug Nanoparticles With Narrow Size-Distribution", Journal of Pharmaceutical Sciences, pp. 2293-2297, vol. 105, Issue 8 (Aug. 1, 2016).
Peter et al., "The Inhibitory Effect of a Coronavirus Spike Protein Fragment with ACE2", Biophysical Journal, pp. 1001-1010, vol. 119 (Mar. 16, 2021).
Pettersen et al., "UCSF Chimera—A visualization system for exploratory research and analysis", Journal of Computational Chemistry, pp. 1605-1612, vol. 25, issue 13 (Oct. 2004).
Petti et al., "Laboratory medicine in Africa: a barrier to effective health care", Clinical Infectious Diseases, pp. 377-382, vol. 42, Issue 3 (2006).
Piai et al., "Structural basis of transmembrane coupling of the HIV-1 envelope glycoprotein", Nature Communications, 11:2317, in 12 pages (2020.
Piepenbrink et al., "Therapeutic activity of an inhaled potent SARS-CoV-2 neutralizing human monoclonal antibody in hamsters", Cell Reports Meicine, 100218 in 21 pages, vol. 2, Issue 3 (Mar. 16, 2021).
Pillai, "Nanomedicines for Cancer Therapy: An Update of FDA Approved and Those under Various Stages of Development", SOJ Pharmacy & Pharmaceutical Sciences, in 13 pages, Open Access, (2014), 1. doi: 10.15226/2374-6866/1/2/00109.
Piras et al., "Changes in Microtubule Phosphorylation during Cell Cycle of HeLa Cells", Proceedings of the National Academy of Sciences of the United States of America, pp. 1161-1165, vol. 72 (1975).
Pirkkala et al., "Roles of the heat shock transcription factors in regulation of the heat shock response and beyond", The FASEB Journal, pp. 1118-1131, vol. 15, Issue 7 (May 2001).
Pizam et al., "The Relationship Between Risk-Taking, Sensation-Seeking, and the Tourist Behavior of Young Adults: A Cross-Cultural Study", Journal of Travel Research, pp. 251-260, vol. 42, Issue 3 (2004).
Pokhrel et al., "Natural variants in SARS-CoV-2 Spike protein pinpoint structural and functional hotspots with implications for prophylaxis and therapeutic strategies", Scientific Reports, vol. 11, Article No. 13120 in 10 pages (2021).
Popat et al., "Enzyme-Responsive Controlled Release of Covalently Bound Prodrug from Functional Mesoporous Silica Nanospheres", Angewandte Chemie, International Edition, pp. 12486-12489, vol. 51, Issue 50 (Dec. 7, 2012).
Popat et al., "Mesoporous silica nanoparticles for bioadsorption, enzyme immobilisation, and delivery carriers", Nanoscale, pp. 2801-2018, vol. 3, Issue 7 (Jul. 1011).
Porta et al., "Folic acid-modified mesoporous silica nanoparticles for cellular and nuclear targeted drug delivery", Advanced Healthcare Materials, pp. 281-286, vol. 2, Issue 2 (Feb. 2013).

Pradhan et al., "A Review of Current Interventions for COVID-19 Prevention", Archives of Medical Research, pp. 363-374, vol. 51, Issue 5 (Jul. 2020).
Prather et al., "Reducing transmission of SARS-CoV-2", Science, pp. 1422-1424, vol. 368, No. 6498 (May 27, 2020).
Preissner et al., "Drug Cocktail Optimization in Chemotherapy of Cancer", PLoS One, e51020, in 7 pages, vol. 7, Issue 12 (Dec. 2012).
Public Health England. Investigation of novel SARS-CoV-2 variant, 2020, Variant of Concern 202012/01 Technical briefing 2-28. PHE: London.
Qi et al., "Intranasal Nanovaccine Confers Homo- and Hetero-Subtypic Influenza Protection", Small, e1703207, vol. 14, Issue 13 (Mar. 27, 2018).
Qiao et al., "SARS-CoV-2 Mpro inhibitors with antiviral activity in a transgenic mouse model", Science, pp. 1374-1378, vol. 371 (2021).
Quinn et al., "Delivering nitric oxide with nanoparticles", Journal of Controlled Release, pp. 190-205, vol. 205 (May 10, 2015).
Radic et al., "Fear and Trembling of Cruise Ship Employees: Psychological Effects of the COVID-19 Pandemic", International Journal of Environmental Research and Public Health, pp. 1-17, vol. 17 (2020).
Radic, "Towards an understanding of a child's cruise experience", Current Issues in Tourism, pp. 237-252, vol. 22, Issue 2 (2019).
Rahikainen et al., Overcoming Symmetry Mismatch in Vaccine Nanoassembly through Spontaneous Amidation, Angewandte Chemie International Edition, pp. 321-330, vol. 60 (2021).
Rajan et al., "Silver nanoparticle ink technology: state of the art", Nanotechnology, Science and Applications, pp. 1-13, vol. 9 (2016).
Ramachandran et al., "SARS-CoV-2 infection enhances mitochondrial PTP complex activity to perturb cardiac energetics", iScience, 103722, in 24 pages, vol. 25 (Jan. 21, 2022).
Ramadan et al., "Hollow Copper Sulfide Nanoparticle-Mediated Transdermal Drug Delivery", Small, pp. 3143-3150, vol. 8 (2012).
Ramirez et al., "Potential chemotherapy side effects: what do oncologists tell parents?", Pediatric Blood & Cancer, pp. 497-502, vol. 52, Issue 4 (Apr. 2009).
Ranga et al., "Immunogenic SARS-CoV-2 Epitopes: In Silico Study Towards Better Understanding of COVID-19 Disease—Paving the Way for Vaccine Development", Vaccines, 408, in 19 pages, vol. 8 (2020).
Rannard et al., "The Selective Reaction of Primary Amines with Carbonyl Imidazole Containing Compounds: Selective Amide and Carbamate Synthesis", Organic Letters, pp. 2117-2120, vol. 2, Issue 14 (2000).
Rasmussen et al., "Pan-specific prediction of peptide-MHC Class I complex stability, a correlate of T Cell Immunogenicity", Journal of Immunology, pp. 1517-1524, vol. 197, No. 4 (2016).
Ray et al., "Aptamers for Targeted Drug Delivery", Pharmaceuticals (Basel), pp. 1761-1778, vol. 3 (2010).
Reboud et al., "Paper-based microfluidics for DNA diagnostics of malaria in low resource underserved rural communities" pp. 4834-4842, vol. 116, No. 11 (Mar. 12, 2019).
Ren et al., "Alterations in the human oral and gut microbiomes and lipidomics in COVID-19", BMJ, Gut Journal, pp. 1253-1265, vol. 70 (2021).
Rentsch et al., "Covid-19 Testing, Hospital Admission, and Intensive Care Among 2,026,227 United States Veterans Aged 54-75 Years, 2020", medRxiv, in 32 pages, doi: https://doi.org/10.1101/2020.04.09.20059964.
Rhea et al., "The S1 protein of SARS-CoV-2 crosses the blood-brain barrier in mice", Nature Neuroscience, pp. 368-378, vol. 24 (Mar. 2021).
Rhoades et al., "Acute SARS-CoV-2 infection is associated with an increased abundance of bacterial pathogens, including Pseudomonas aeruginosa in the nose", Cell Reports, 109367, in 13 pages, vol. 36, Issue 9 (Aug. 31, 2021).
Rice et al., "Matrix stiffness induces epithelial-mesenchymal transition and promotes chemoresistance in pancreatic cancer cells", Oncogenesis, 2017, 7, e352.
Ridler et al., "Picture Thresholding Using an Iterative Selection Method", IEEE Transactions on Systems, p. 311, vol. 9 (1979).

(56) References Cited

OTHER PUBLICATIONS

Riihimäki et al., "Comparison of survival of patients with metastases from known versus unknown primaries: survival in metastatic cancer", BMC Cancer, 2013, 13:36. doi: 10.1186/1471-2407-13-36.
Ripperger et al., "Detection, prevalence, and duration of humoral responses to SARS-CoV-2 under conditions of limited population exposure", medRxiv, pp. 1-44 (2020).
Ritchie et al., "A review of research on tourism risk, crisis and disaster management: Launching the annals of tourism research curated collection on tourism risk, crisis and disaster management", Annals of Tourism Research, 102812, vol. 79 (Nov. 2019).
Robbiani, et al., "Convergent antibody responses to SARS-CoV-2 in convalescent individuals", Nature, pp. 437-442, vol. 584 (2020) https://doi.org/10.1038/s41586-020-2456-9.
Robergs, "Lessons from Popper for science, paradigm shifts, scientific revolutions and exercise physiology", BMJ Open Sport & Exercise Medicine, 3(1):e000226. doi:10.1136/bmjsem-2017-000226. (2017).
Robinson et al., "IPD-IMGT/HLA Database", Nucleic Acids Research, pp. D948-D955, vol. 48 (2020).
Rodrigues et al., "Functionalizing Ferritin Nanoparticles for Vaccine Development", Pharmaceutics, 1621, in 25 pages, vol. 13 (2021).
Roe et al., "PTRAJ and CPTRAJ: Software for processing and analysis of molecular dynamics trajectory data", Journal of Schemical Theory and Computation, pp. 3084-3095, vol. 9 (2013).
Rose et al., "The RCSB Protein Data Bank: new resources for research and education", Nucleic Acids Research, pp. D475-D482, vol. 14 Issue D1 (Jan. 2013).
Rosenholm et al., "Amino-functionalization of large-pore mesoscopically ordered silica by a one-step hyperbranching polymerization of a surface-grown polyethyleneimine", Chemical Communications, pp. 3909-3911, Issue 37 (2006).
Rosenholm et al., "Cancer-cell targeting and cell-specific delivery by mesoporous silicananoparticles", Journal of Materials Chemistry, pp. 2707-2013, vol. 20, Issue 14 (2010).
Rosenholm et al., "Hyperbranching Surface Polymerization as a Tool for Preferential Functionalization of the Outer Surface of Mesoporous Silica", Chemical Materials, pp. 1126-1133, vol. 20 (2008).
Rosenholm et al., "Targeted Intracellular Delivery of Hydrophobic Agents using Mesoporous Hybrid Silica Nanoparticles as Carrier Systems", Nano Letters, pp. 3308-3311, vol. 9 (2009).
Rosenholm et al., "Targeting of Porous Hybrid Silica Nanoparticles to Cancer Cells", ACS Nano, pp. 197-206, vol. 3 (2009).
Rosenholm et al., "Towards establishing structure-activity relationships for mesoporous silica in drug delivery applications", Journal of Controlled Release, pp. 157-164, vol. 128, Issue 2 (Jun. 4, 2008).
Rosenholm et al., "Towards multifunctional, targeted drug delivery systems using mesoporous silica nanoparticles—opportunities & challenges", Nanoscale, pp. 1870-1883, vol. 2, Issue 10 (2010).
Rosenholm, J.M. et al., "Cancer-cell-specific induction of apoptosis using mesoporous silica nanoparticles as drug-delivery vectors", Small, 2010, 6(11):1234-41. doi: 10.1002/smll.200902355.
Roshmi et al., "Effect of biofabricated gold nanoparticle-based antibiotic conjugates on minimum inhibitory concentration of bacterial isolates of clinical origin" Gold Bull, pp. 63-71, vol. 48 (2015) https://doi.org/10.1007/s13404-015-0162-4.
Rosqvist et al., "A low-cost paper-based platform for fast and reliable screening of cellular interactions with materials", Journal of Materials Chemistry B, pp. 1146-1156, vol. 8, No. 6 (Feb. 14, 2020).
Rosqvist et al., "Human dermal fibroblast proliferation controlled by surface roughness of two-component nanostructured latex polymer coatings", Colloids and Surfaces B: Biointerfaces, pp. 136-144, vol. 174 (Feb. 2019).
Rossi, et al., "Characteristics and outcomes of a cohort of SARS-CoV-2 patients in the Province of Reggio Emilia, Italy", 2020, medRxiv. 2020.2004.2013.20063545.
Roth et al., "Norovirus mechanisms of immune antagonism", Current Opinion in Virology, pp. 24-30, vol. 16 (Feb. 2016).
Rueden et al., "ImageJ2: ImageJ for the next generation of scientific image data", BMC Bioinformatics, 18(1):529. doi: 10.1186/s12859-017-1934-z. (2017).
Rundle et al., "Hand hygiene during COVID-19: Recommendations from the American Contact Dermatitis Society", Journal of the American Academy of Dermatology, pp. 1730-1737, vol. 83, No. 6 (2020).
Sader et al., "Antimicrobial activity of dalbavancin and comparators against *Staphylococcus aureus* causing pneumonia in patients with and without cystic fibrosis", International Journal of Infectious Diseases, pp. 69-71, vol. 107 (2021).
Safa, "c-FLIP, A Master Anti-Apoptotic Regulator", Experimental Oncology, pp. 176-184, vol. 34 (2012).
SAGE Handbook of Mixed Methods in Social & Behavorial Research, 2nd Edition, "Mapping the Developing Landscape of Mixed Methods Research", Chapter 1, Part 1, pp. 45-68, Tashakkori et al. Editors, SAGE Publications Ltd., (2010).
Saini et al., "An Appraisal of Proliferation and Apoptotic Markers in Papillary Thyroid Carcinoma: An Automated Analysis", PLoS One, 2016, 11(2):e0148656. doi: 10.1371/journal.pone.0148656.
Salminen et al., "Celastrol: Molecular targets of Thunder God Vine", Biochemical and Biophysical Research Communications, pp. 439-442, vol. 394, Issue 3 (Apr. 9, 2010).
Samelson, et al. "BRD2 inhibition blocks SARS-CoV-2 infection by reducing transcription of the host cell receptor ACE2", Nature Cell Biology, pp. 24-34, vol. 24 (Jan. 2022).
Sanberg et al., "Changing the academic culture: Valuing patents and commercialization toward tenure and career advancement", Proceedings of the National Academy of Sciences of the United States of America, pp. 6542-6547, vol. 111, No. 18 (May 6, 2014).
Sanchez-Mazas, "HLA studies in the context of coronavirus outbreaks", Swiss Medical Weekly, in 5 pages, (2020).
Sandqvist et al., "Heterotrimerization of Heat-Shock Factors 1 and 2 Provides a Transcriptional Switch in Response to Distinct Stimuli", Molecular Biolgy of the Cell, pp. 1340-1347, vol. 20, (Mar. 1, 2009).
Sanhai et al., "Seven challenges for nanomedicine", Nature Nanotechnology, pp. 242-244, vol. 3 (2008).
Sapp et al., "Multilayer three-dimensional filter paper constructs for the culture and analysis of aortic valvular interstitial cells", Acta Biomaterialia, pp. 199-206, vol. 13 (Feb. 2015).
Sarfraz et al., "Photo-thermal and cytotoxic properties of inkjet-printed copper sulfide films on biocompatible latex coated substrates", Applied Surface Science, pp. 1087-1095, vol. 435 (Mar. 2018).
Sarfraz et al., "Printed copper acetate based H2S sensor on paper substrate", Sensors and Actuators B: Chemical, pp. 868-873, vol. 173 (Oct. 2012).
Sarfraz et al., "Sub-ppm electrical detection of hydrogen sulfide gas at room temperature based on printed copper acetate-gold nanoparticle composite films", RSC Advances, pp. 13525-13529, vol. 5, Issue 18 (2015).
Sarge et al., "Activation of heat shock gene transcription by heat shock factor 1 involves oligomerization, acquisition of DNA-binding activity, and nuclear localization and can occur in the absence of stress", Molecular Cell Biology, pp. 1392-1407, vol. 13 (Mar. 1993).
Saris A, et al. "Distinct cellular immune profiles in the airways and blood of critically ill patients with COVID-19", Thorax, pp. 1010-1019, vol. 10 (Oct. 2021).
Sasaki et al., "Doxorubicin-induced Inhibition of Prolyl Hydroxylation during Collagen Biosynthesis in Human Skin Fibroblast Cultures Relevance to Impaired Wound Healing", Journal of Clinical Investigation pp. 1735-1741, vol. 80 (Dec. 1987).
Satriano et al., "Surface free energy and cell attachment onto ion-beam irradiated polymer surfaces", Nuclear Instruments and Methods in Physics Research Section B: Beam Interactions with Materials and Atoms, pp. 287-293, vol. 208 (Aug. 2003).
Savjani et al., "Drug solubility: importance and enhancement techniques", ISRN Pharmaceutics, Article 195727, in 10 pages vol. 2012 (2012).
Savolainen-Kopra et al., "Single treatment with ethanol hand rub is ineffective against human rhinovirus—hand washing with soap and

(56) References Cited

OTHER PUBLICATIONS water removes the virus efficiently", Journal of Medical Virology, pp. 534-547, vol. 84, Issue 3 (Mar. 2012).
Schindelin et al., "Fiji: an open-source platform for biological-image analysis", Nature Methods, pp. 671-675, vol. 9 (2012).
Schindelin et al., "The ImageJ ecosystem: An open platform for biomedical image analysis", Molecular Reproduction & Development, pp. 518-529, vol. 82, Issue 7-8 (Jul.-Aug. 2015).
Schneider et al., "NIH Image to ImageJ: 25 years of Image Analysis". Nature Methods, pp. 671-675, vol. 9 (Jul. 2012).
Schoenmaker et al., "mRNA-lipid nanoparticle COVID-19 vaccines: Structure and stability", International Journal of Pharmaceutics, pp. 120586, in 13 pages, vol. 601 (May 15, 2021).
Schuhmacher et al., "Changing R&D models in research-based pharmaceutical companies", Journal of Translational Medicine, 14:105 (2016).
Schulte et al., "Ethical and Scientific Issues of Nanotechnology in the Workplace", Environmental Health Perspectives, pp. 5-12, vol. 115, No. 1 ((Jan. 2007).
Scudellari, "The sprint to solve coronavirus protein structures—and disarm them with drugs", Nature, pp. 252-255, vol. 581 (2020).
Seigneuric et al., "From Nanotechnology to Nanomedicine: Applications to Cancer Research", Current Molecular Medicine, pp. 640-652, vol. 10 (2010).
Sekimukai et al., "Gold nanoparticle-adjuvantes S protein induces a strong antigen-specific IgG response against severe acute respiratory syndrome-related coronavirus infection, but fails to induce protective antibodies and limit eosinophilic infiltration in lungs", Microbiology and Immunology, pp. 33-51, vol. 64, No. 1 (Jan. 2020).
Seligmann et al., "Tubulin: an example of targeted chemotherapy", Future Medicinal Chemistry, pp. 339-352, vol. 5 (2013).
Semerdzhiev et al., "Interactions between SARS-CoV-2 N-Protein and α-Synuclein Accelerate Amyloid Formation", . ACS Chemical Neuroscience, pp. 143-150, vol. 13 (2022).
Shaffer, "15 drugs being tested to treat COVID-19 and how they would work", Nature Medicine, doi: 10.1038/d41591-020-00019-9.
Shajahan et al., "Deducing the N- and O-glycosylation profile of the spike protein of novel coronavirus SARS-CoV-2", Glycobiology, pp. 981-988, vol. 30, No. 12 (2020) Glycobiology, 2020, 1-20.
Shang et al., "Engineered nanoparticles interacting with cells: size matters", Journal of Nanobiotechnology, 12:5, in 11 pages (2014) doi: 10.1186/1477-3155-12-5.
Shang et al., "Structural basis of receptor recognition by SARS-CoV-2", Nature, pp. 221-224, vol. 581 (2020).
Shaw et al., "90—Vaccines", Clinical Immunology (Fourth Edition), 2013, pp. 1095-1121, ISBN 9780723436911.
Shaw, "Glucose metabolism and cancer", Current Opinion in Cell Biology, pp. 598-608, vol. 18, Issue 6 (Dec. 2006).
Shen et al., "Assessment of folate receptor-β expression in human neoplastic tissues" Oncotarget, pp. 14700-14709, vol. 6, No. 16, (Jun. 10, 2015) doi: 10.18632/oncotarget.3739.
Shinde et al., "Efficacy of NVX-CoV2373 Covid-19 Vaccine against the B.1.351 Variant", The New England Journal of Medicine, pp. 1899-1909, vol. 384(20) (May 20, 2021).
Shrader-Frechette, "Nanotoxicology and Ethical Conditions for Informed Consent", NanoEthics, pp. 47-56, vol. 1 (2007).
Shuchman, "Obtaining funding an age-old problem for young researchers with novel ideas", CMAJ, pp. E516-E517, vol. 190, Isue 16 (Apr. 23, 2018).
Sidney et al., "HLA class I supertypes: A revised and updated classification", BMC Immunology, pgs.in 15 pages, vol. 9:1 (2008).
Singanayagam et al., "ATACCC Study Investigators. Community transmission and viral load kinetics of the SARS-CoV-2 delta (B.1.617.2) variant in vaccinated and unvaccinated individuals in the UK: a prospective, longitudinal, cohort study", The Lancet Infectious Diseases, pp. 183-195, vol. 22, Issue 2 (Feb. 1, 2022).
Singh et al., "Jr Nanoparticle-based targeted drug delivery", Experimental and Molecular Pathology, pp. 215-223, vol. 86, Issue 3 (Jun. 2009).
Singhal, "A Review of Coronavirus Disease-2019 (COVID-19)", The Indian Journal of Pediatrics, pp. 281-286, vol. 87 (Apr. 2020).
Singhvi et al., "Polylactic acid: synthesis and biomedical applications", Journal of Applied Microbiology, pp. 1612-1626, vol. 127, Issue 6 (Dec. 2019).
Smith, et al., "Immunogenicity of a DNA vaccine candidate for COVID-19", Nature Communications, Article No. 2601, in 13 pages, vol. 11 92020).
Söderberg-Nauclér, "Does reactivation of cytomegalovirus contribute to severe COVID-19 disease?", Immunity & Ageing, in 7 pages, 18:12 (2021).
Sohail et al., "In silico T cell epitope identification for SARS-CoV-2: Progress and perspectives", pp. 29-47, vol. 171 (Apr. 2021).
Sohrabi et al., "World Health Organization declares Global Emergency: A review of the 2019 Novel Coronavirus (COVID-19)", International Journal of Surgery, pp. 71-76, vol. 76 (Apr. 2020).
Solon et al., "Fibroblast Adaptation and Stiffness Matching to Soft Elastic Substrates", Biophysical Journal, pp. 44353-44461, vol. 93 (Dec. 15, 2007).
Soltman et al., "Inkjet-Printed Line Morphologies and Temperature Control of the Coffee Ring Effect", Langmuir, pp. 2224-2231, vol. 24 (2008).
Song et al., "Formulation and evaluation of celastrol-loaded liposomes", Molecules, pp. 7880-7892, vol. 16 (2011).
Sönmez et al., "Determining Future Travel Behavior from Past Travel Experience and Perceptions of Risk and Safety", Journal of Travel Research, pp. 171-177, vol. 37 (1998).
Sonoke et al., "Galactose-Modified Cationic Liposomes as a Liver-Targeting Delivery System for Small Interfering RNA", Biological and Pharmaceutical Bulletin, pp. 1338-1342, vol. 34 (2011).
Souza et al., "A comparison of TEM and DLS methods to characterize size distribution of ceramic nanoparticles", Journal of Physics, in 5 pages, 012039, vol. 733 (2016).
Sportelli et al., "Can Nanotechnology and Materials Science Help the Fight against SARS-CoV-2?", Nanomaterials (Basel), 10(4):802. doi: 10.3390/nano10040802. PMID: 32326343; PMCID: PMC7221591. (Apr. 21, 2020).
Srinivasan et al., "Structural Genomics of SARS-COV-2 Indicates Evolutionary Conserved Functional Regions of Viral Proteins", Viruses, 360, vol. 12 (Mar. 25, 2020) doi: 10.3390/v12040360.
Sriraman et al., "Barriers to Drug Delivery in Solid Tumors", Tissue Barriers, 2:e29528, in 10 pages (2014) doi: 10.4161/tisb.29528.
Srivastava et al., "Critical Review on the Toxicity of Some Widely Used Engineered Nanoparticles", Industrial & Engineering Chemistry Research, pp. 6209-6233, vol. 54 (2015).
St. Dollente Mesias et al., "Effective ACE2 peptide—nanoparticle conjugation and its binding with the SARS-Cov-2 RBD quantified by dynamic light scattering", Chemical Communications, pp. 6979-6982, vol. 57 (2021).
Stanifer et al., "Critical Role of Type III Interferon in Controlling SARS-CoV-2 Infection in Human Intestinal Epithelial Cells", Cell Reports. 107863 in 15 pages, vol. 32, Issue 1 (Jul. 7, 2020).
Steichen et al., "A review of current nanoparticle and targeting moieties for the delivery of cancer therapeutics", European Journal of Pharmaceuticial Sciences: Official Journal of the European Federation for Pharmaceutical Sciences, pp. 416-427, vol. 48 (Feb. 14, 2013).
Stephan, "How Economics Shapes Science", Boston, MA: Harvard University Press, 2012a, doi: 10.1111/1475-4932.12480.
Stephan, "Research efficiency: Perverse incentives", Nature, pp. 29-31, vol. 484 (2012).
Struss et al., "Paper strip whole cell biosensors: a portable test for the semiquantitative detection of bacterial quorum signaling molecules", Analytical Chemistry, pp. 4457-4463, vol. 82 (Jun. 2010).
Su et al., "Developing pan-β-coronavirus vaccines against emerging SARS-CoV-2 variants of concern", Trends in Immunology, pp. 170-172, vol. 43, Issue 3 (Mar. 1, 2022).
Subbaraman, "How Do Vaccinated People Spread Delta? What The Science Says", Nature, pp. 327-328, vol. 596 (Aug. 19, 2021).
Sudhakar, "History of Cancer, Ancient and Modern Treatment Methods", Journal of Cancer Science and Therapy, pp. 1-4, vol. 1 (Dec. 1, 2009) doi: 10.4172/1948-5956.100000e2.

(56) References Cited

OTHER PUBLICATIONS

Sukumaran et al., "Canonical Transient Receptor Potential Channel 2 (TRPC2) as a Major Regulator of Calcium Homeostasis in Rat Thyroid FRTL-5 Cells: Importance of Protein Kinase C δ (PKCδ) and Stromal Interaction Molecule 2 (STIM2)", Journal of Biological Chemistry, pp. 44345-44360, vol. 287 (Dec. 28, 2012).
Suman et al., "Sustainability of Coronavirus on Different Surfaces", Journal of Clinical and Experimental Hepatology, pp. 386-390, vol. 10, Issue 4 (Jul. 1, 2020).
Sun et al., "A systematic analysis of FDA-approved anticancer drugs", BMC Systems Biology, vol. 11, Supplement 5, Article No. 87 (2017).
Sun et al., "Cationic nanoparticles directly bind angiotensin-converting enzyme 2 and induce acute lung injury in mice", Particle and Fibre Toxicology, vol. 12, Article No. 4 (2015).
Sun et al., "Recent Advance on Mesoporous Silica Nanoparticles-Based Controlled Release System: Intelligent Switches Open up New Horizon". Nanomaterials (Basel), pp. 2019-2053, vol. 5, No. 4 (2015).
Sun et al., "RIP-1/c-FLIPL Induce Hepatic Cancer Cell Apoptosis Through Regulating Tumor Necrosis Factor-Related Apoptosis-Inducing Ligand (TRAIL)", Medical Science Monitor, pp. 1190-1199, vol. 23 (2017).
Sun et al., "The efficacy of social distance and ventilation effectiveness in preventing COVID-19 transmission", Sustainable Cities and Society, pp. 1-10, vol. 62 (2020).
Sun, "Nanomaterial-Based Vaccine Adjuvants", Journal of Materials Chemistry B, pp. 5496-5509, vol. 4 (Sep. 7, 2016).
Sungnak et al., "SARS-CoV-2 entry factors are highly expressed in nasal epithelial cells together with innate immune genes", Nature Medicine, pp. 681-687, vol. 26 (2020).
Sweeney et al., "Peptide-Mediated Targeting Mesoporous Silica Nanoparticles: A Novel Tool for Fighting Bladder Cancer", Journal of Biomedical Nanotechnology, pp. 232-242, vol. 13, No. 2 (2017).
Szymanski et al., "Bacterial and Viral Infections", Essentials of Glycobiology [Internet], 3rd edition. Cold Spring Harbor (NY): Cold Spring Harbor Laboratory Press, Chapter 42 (2015).
Tada et al., "A soluble ACE2 microbody protein fused to a single immunoglobulin Fc domain is a potent inhibitor of SARS-CoV-2 infection in cell culture", bioRxiv, pp. 1-61 (2020).
Takahashi et al., "A low-cost paper-based synthethic biology platform for analysing gut microbiota and host biomarkers", Nature Communications, pp. 1-12, vol. 9, Article No. 3347 (2018).
Tamirat et al., "Deciphering the structural effects of activating EGFR somatic mutations with molecular dynamics simulation", Journal of Visualized Experiments, pp. 1-12 (2020).
Tan et al., "A COVID-19 vaccine candidate using SpyCatcher multimerization of the SARS-CoV-2 spike protein receptor-binding domain induces potent neutralising antibody responses", Nature Communications, pp. 1-16, vol. 12, Article No. 542 (2021).
Te Velthuis et al., "Zn(2+) Inhibits Coronavirus and Arterivirus RNA Polymerase Activity In Vitro and Zinc Ionophores Block the Replication of These Viruses in Cell Culture", PLOS Pathogens, pp. 1-10, vol. 6, No. 11 (2010).
Tena et al., "Deposition of inhaled particles in the lungs", Archivos de Bronconeumologia (English Edition), pp. 240-246, vol. 48, Issue 7 (Jul. 2012).
Thacker, "Covid-19: Researcher blows the whistle on data integrity issues in Pfizer's vaccine trial", BMJ, pp. 1-3, vol. 375, No. 2635 (2021).
Thakur et al., "Eps15 homology domain containing protein of Plasmodium falciparum (PfEHD) associates with endocytosis and vesicular trafficking towards neutral lipid storage site", Biochimica et Biophysica (BBA) Acta—Molecular Cell Research, pp. 2856-2869, vol. 1853, Issue 11, Part A (2015).
The Novel Coronavirus Pneumonia Emergency Response Epidemiology Team, "Vital Surveillances: The Epidemiological Characteristics of an Outbreak of 2019 Novel Coronavirus Diseases (COVID-19)—China, 2020", China CPC Weekly, pp. 113-122, vol. 2(8) (2020).
Thomas et al., "STAT1: a modulator of chemotherapy-induced apoptosis", Cancer Research, pp. 8357-8364, vol. 64, Issue 22 (2004).
Thorn et al., "Doxorubicin pathways: pharmacodynamics and adverse effects", Pharmacogenet Genomics, pp. 440-446, vol. 21, No. 7 (2011).
Tian et al., "Calibrated Intervention and Containment of the COVID-19 Pandemic", arXiv, pp. 1-54 (2020).
Tinari et al., "Covid-19: Whatever happened to the Novavax vaccine?", BMJ, Dec 8, vol. 375, No. 2965 (2021).
Tobjörk et al., "IR-sintering of ink-jet printed metal nanoparticles on paper", Thin Solid Films, pp. 2949-2955, vol. 520, Issue 7 (2012).
Tohme et al., "Surgery for Cancer: A Trigger for Metastases", Cancer Research, pp. 1548-1552, vol. 77, Issue 7 (2017).
Tojkander et al., "Actin stress fibers—assembly, dynamics and biological roles", Journal of Cell Science, pp. 1855-1864, vol. 125, Issue 8 (2012).
Tokiwa et al., "Biodegradability of plastics", International Journal of Molecular Sciences, pp. 3722-3742, vol. 10 (2009).
Tortorici et al., "Structural basis for human coronavirus attachment to sialic acid receptors", Nature Structural & Molecular Biology, pp. 481-489, vol. 26 (2019).
Towers et al., "Quantifying the relative effects of environmental and direct transmission of norovirus", Royal Society Open Science, pp. 1-13, vol. 5 (2018).
Trinchieri, "Interleukin-12 and the regulation of innate resistance and adaptive immunity", Nature Reviews, Immunology, pp. 133-146, vol. 3 (2003).
Trott et al., "Activation of heat shock and antioxidant responses by the natural product celastrol: transcriptional signatures of a thiol-targeted molecule", Molecular Biology of the Cell, pp. 1104-1112, vol. 19, No. 3 (2008).
Tsai et al., "Monoclonal Antibody-Functionalized Mesoporous Silica Nanoparticles (MSN) for Selective Targeting Breast Cancer Cells", Journal of Materials Chemistry, pp. 5737-5743, vol. 19 (2009).
Tsao et al., "HLA-A*0201 T-cell epitopes in severe acute respiratory syndrome (SARS) coronavirus nucleocapsid and spike proteins", Biochemical and Biophysical Research Communications, pp. 63-71, vol. 344, Issue 1 (2006).
Tuomisto et al., "An agent-based epidemic model REINA for COVID-19 to identify destructive policies", medRxiv, in 29 pages, doi: https://doi.org/10.1101/2020.04.09.20047498.
Umezawa et al., "Maternal inhalation of carbon black nanoparticles induces neurodevelopmental changes in mouse offspring", Particle and Fibre Toxicology, pp. 1-18, vol. 15, Article No. 36 (2018).
Underwood et al., "Challenges and approaches for particle size analysis on micrographs of nanoparticles loaded onto textile surfaces", NIST Special Publication 1200-22, pp. 1-17 (2017).
Upla et al., "Clustering induces a lateral redistribution of alpha 2 beta 1 integrin from membrane rafts to caveolae and subsequent protein kinase C-dependent internalization", Molecular Biology of the Cell, pp. 625-636, vol. 15, No. 2 (2004).
Urbano et al., "Apoptosis and the FLIP and NF-kappa B proteins as pharmacodynamic criteria for biosimilar TNF-alpha antagonists", Biologics: Targets and Therapy, pp. 211-220, vol. 8 (2014).
Urdaniz et al., "One-shot identification of SARS-CoV-2 S RBD escape mutants using yeast screening", Cell Rep, Aug. 31, 2021, 36(9):109627. doi: 10.1016/j.celrep.2021.109627. Epub Aug. 10, 2021. PMID: 34416153; PMCID: PMC8352667.
Vallet-Regí et al., "Mesoporous materials for drug delivery", Angewandte Chemie International Edition, pp. 7548-7558. Vol. 46, Issue 40 (2007).
Vallet-Regí et al., "Mesoporous Silica Nanoparticles for Drug Delivery: Current Insights", Molecules, pp. 1-19, vol. 23, Issue 1 (2017).
Van Dorp et al., "Emergence of genomic diversity and recurrent mutations in SARS-CoV-2", Infection, Genetics and Evolution, pp. 1-9, vol. 83 (2020).
Van Grinsven et al., "Fast Convolutional Neural Network Training Using Selective Data Sampling: Application to Hemorrhage Detection in Color Fundus Images", IEEE Transactions on Medical Imaging, pp. 1273-1284, vol. 35, Issue 5 (2016).

(56) References Cited

OTHER PUBLICATIONS

Van Oss, "Use of the combined Lifshitz-van der Waals and Lewis acid-base approaches in determining the apolar and polar contributions to surface and interfacial tensions and free energies", Journal of Adhesion Science and Technology, pp. 669-677, vol. 16, Issue 66 (2002).

Van Rooyen et al., "Comparison of T-cell immune responses to SARS-CoV-2 spike (S) and nucleocapsid (N) protein using an in-house flow-cytometric assay in laboratory employees with and without previously confirmed COVID-19 in South Africa: nationwide cross-sectional study", Journal of Clinical Pathology, pp. 1-7 (2022).

Varki et al., "Essentials of Glycobiology [Internet], 4th edition", Cold Spring Harbor (NY): Cold Spring Harbor Laboratory Press, Chapter 42 (2022).

Varkouhi et al., "Endosomal Escape Pathways for Delivery of Biologicals", Journal of Controlled Release, pp. 220-228, vol. 151, Issue 3 (2011).

Venditto et al., "Cancer nanomedicines: so many papers and so few drugs!", Advanced Drug Delivery Reviews, pp. 80-88, vol. 65, Issue 1 (2013).

Venkatakrishnan et al., "Benchmarking evolutionary tinkering underlying human-viral molecular mimicry shows multiple host pulmonary-arterial peptides mimicked by SARS-CoV-2", Cell Death Discovery, pp. 1-14, vol. 6, Article No. 96 (2020).

Verdoni et al., "An outbreak of severe Kawasaki-like disease at the Italian epicentre of the SARS-CoV-2 epidemic: An observational cohort study", The Lancet, pp. 1771-1778, vol. 395, Issue 10239 (2020).

Verma et al., "Effect of Surface Properties on Nanoparticle-Cell Interactions", Small, pp. 12-21, vol. 6, Issue 1 (2010).

Verma et al., "Interactions of Peptide Coated Gold Nanoparticles with Spike Protein of the SARS-CoV-2: A Basis for Design of a Simple and Rapid Detection Tool", ChemRxiv, pp. 1-18 (2020).

Vihervaara et al., "Transcriptional response to stress in the dynamic chromatin environment of cycling and mitotic cells", Proceedings of the National Academy of Sciences of the USA, pp. E3388-E3397, vol. 110, No. 36 (2013).

Villacé-Molinero et al., "Understanding the new post-COVID-19 risk scenario: Outlooks and challenges for a new era of tourism", Tourism Management, pp. 1-11, vol. 86 (2021).

Vita et al., "The Immune Epitope Database (IEDB): 2018 update", Nucleic Acids Research, pp. D339-D343, vol. 47, Issue D1 (2019).

Vitte et al., "Is there a predictable relationship between surface physical-chemical properties and cell behaviour at the interface?", European Cells and Materials, pp. 52-63, vol. 7 (2004).

Vivero-Escoto et al., "Mesoporous silica nanoparticles for intracellular controlled drug delivery", Small, pp. 1952-1967, vol. 6, Issue 18 (2010).

Von Haartman et al., "On the intracellular release mechanism of hydrophobic cargo and its relation to the biodegradation behavior of mesoporous silica nanocarriers", European Journal of Pharmaceutical Sciences, pp. 17-27, vol. 95 (2016).

Voss et al., "Prevalent, protective, and convergent IgG recognition of SARS-CoV-2 non-RBD spike epitopes", Science, pp. 1108-1112, vol. 372, No. 6546 (2021).

Vuorinen et al., "Modelling aerosol transport and virus exposure with numerical simulations in relation to SARS-CoV-2 transmission by inhalation indoors", Safety Science, pp. 1-23, vol. 130 (2020).

Wagner et al., The emerging nanomedicine landscape, Nature Biotechnology, pp. 1211-1217, vol. 24 (2006).

Walls et al., "Elicitation of potent neutralizing antibody responses by designed protein nanoparticle vaccines for SARS-CoV-2", Cell, pp. 1367-1382, vol. 183, Issue 5 (2020).

Wan et al., "On the Controllable Soft-Templating Approach to Mesoporous Silicates", Chemical Reviews, pp. 2821-2860, vol. 107, No. 7 (2007).

Wan et al., "Receptor Recognition by the Novel Coronavirus from Wuhan: an Analysis Based on Decade-Long Structural Studies of SARS Coronavirus", Journal of Virology, pp. 1-9, vol. 94, No. 7 (2020).

Wang et al., "Manufacturing Techniques and Surface Engineering of Polymer Based nanoparticles for Targeted Drug Delivery to Cancer", Nanomaterials, pp. 1-18, vol. 6, No. 2 ((Feb. 2016).

Wang et al., "A human monoclonal antibody blocking SARS-CoV-2 infection", Nature Communications, pp. 1-6, vol. 11, Article No. 2251 (2020).

Wang et al., "ACE2 can act as the secondary receptor in the FcγR-dependent ADE of SARS-CoV-2 infection", iScience, pp. 1-20, vol. 25, Issue 1 (2022).

Wang et al., "Akt-mediated eminent expression of c-FLIP and Mcl-1 confers acquired resistance to TRAIL-induced cytotoxicity to lung cancer cells", Molecular Cancer Therapeutics, pp. 1156-1163, vol. 7, No. 5 (2008).

Wang et al., "Cetuximab-Modified Mesoporous Silica Nano-Medicine Specifically Targets EGFR-Mutant Lung Cancer and Overcomes Drug Resistance", Scientific Reports, pp. 1-10, vol. 6, Article No. 25468 (2016).

Wang et al., "Dalbavancin binds ACE2 to block its interaction with SARS-CoV-2 spike protein and is effective in inhibiting SARS-CoV-2 infection in animal models", Cell Research, pp. 17-24, vol. 31 (2020).

Wang et al., "Diverse functional autoantibodies in patients with COVID-19", Nature, pp. 283-288, vol. 595 (2021).

Wang et al., "Functional differences among the spike glycoproteins of multiple emerging severe acute respiratory syndrome coronavirus 2 variants of concern", iScience, pp. 1-22, vol. 24, No. 11 (2021).

Wang et al., "Microfabricated electrochemical cell-based biosensors for analysis of living cells in vitro", Biosensors, pp. 127-170, vol. 2 (2012).

Wang et al., "Multi-organ distant metastases confer worse disease-specific survival in differentiated thyroid cancer", Thyroid, pp. 1594-1599, vol. 24, No. 11 (2014).

Wang et al., "Thiol adsorption on and reduction of copper oxide particles and surfaces", Langmuir, pp. 3848-3857, vol. 32 (2016).

Wang, "Ordered Mesoporous Materials for Drug Delivery", Microporous and Mesoporous Materials, pp. 1-9, vol. 117, Issues 1-2 (2009).

Watanabe et al., "Site-specific analysis of the SARS-CoV-2 glycan shield", bioRxiv, pp. 1-20 (2020).

Watkins, "Preventing a covid-19 pandemic", BMJ, pp. 1-2 (2020).

Weber et al., "Expression of functional folate receptors by human parathyroid cells", Surgery, pp. 1385-1393, vol. 154, Issue 6 (2013).

Wei et al., "HDL-scavenger receptor B type 1 facilitates SARS-CoV-2 entry", Nature Metabolism, pp. 1391-1400, vol. 2 (2020).

Weibel et al., "Mechanism of Zn Particle Oxidation by H2O and CO2 in the Presence of ZnO", Chemistry of Materials, pp. 6486-6495, vol. 26 (2014).

Weiskopf et al., "Phenotype of SARS-CoV-2-specific T-cells in COVID-19 patients with acute respiratory distress syndrome", medRxiv, pp. 1-29 (2020).

Weiss et al., "Toward Nanotechnology-Enabled Approaches against the COVID-19 Pandemic", ACS Nano, pp. 6383-6406, vol. 14 (2020).

Westerheide et al., "Celastrols as Inducers of the Heat Chock Response and Cytoprotection", Journal of Biological Chemistry, vol. 279, No. 53, pp. 56053-56060 (2004).

Westerheide et al., "Stress-inducible regulation of heat shock factor 1 by the deacetylase SIRT1", Science, pp. 1063-1066, vol. 323, Issue 5917 (2009).

Whisenant et al., "Blocking Coronavirus 19 Infection via the SARS-CoV-2 Spike Protein: Initial Steps", ACS Medicinal Chemistry Letters, pp. 1076-1078, vol. 11 (2020).

Whitehouse, "Handbook of Surface and Nanometrology (second edition)", CRC Press, Coventry, UK (2011).

Wicki et al., "Nanomedicine in cancer therapy: challenges, opportunities, and clinical applications", Journal of Controlled Release, pp. 138-157, vol. 200 (2015).

Wilbrandt, "The significance of the structure of a membrane for its selective permeability", Journal of General Physiology, pp. 933-965, vol. 18, No. 6 (1935).

(56) References Cited

OTHER PUBLICATIONS

Williams, "The Williams Dictionary of Biomaterials" (1999).
Willyard, "Coronavirus Blood-Clot Mystery Intensifies", Nature, p. 250, vol. 581 (May 21, 2020).
Wong et al., "Mechanisms and implications of dual-acting methotrexate in folate-targeted nanotherapeutic delivery", International Journal of Molecular Sciences, pp. 1772-1790, vol. 16 (2015).
Wu et al., "A new coronavirus associated with human respiratory disease in China", Nature, pp. 265-269, vol. 579 (2020).
Wu et al., "Effect of surface roughness on the initial response of MC3T3-E1 cells cultured on polished titanium alloy", Bio-medical Materials and Engineering, pp. 155-164, vol. 26 (2015).
Wu et al., "Paper as a scaffold for cell cultures: Teaching an old material new tricks", MRS Communications, pp. 1-14, vol. 8, No. 1 (2018).
Wut et al., "Crisis management research (1985-2020) in the hospitality and tourism industry: A review and research agenda", Tourism Management, p. 104307, vol. 85 (2021).
Xiao et al., "A dual-responsive mesoporous silica nanoparticle for tumor-triggered targeting drug delivery", Small, pp. 591-598, vol. 10, Issue 3 (2014).
Xiao, "CuS nanoparticles: clinically favorable materials for photothermal applications?", Nanomedicine, pp. 373-375, vol. 9, No. 3 (2014).
Xie et al., "Copper sulfide nanocrystals with tunable composition by reduction of covellite nanocrystals with CU+ ions", Journal of the American Chemical Society, pp. 17630-17637, vol. 135 (2013).
Xie et al., "Nanoparticle-based theranostic agents", Advanced Drug Delivery Review, pp. 1064-1079, vol. 62, No. 11 (2010).
Xie et al., "Nanoscale transformations in covellite (CuS) nanocrystals in the presence of divalent metal cations in a mild reducing environment", Chemistry of Materials, pp. 7531-7537, vol. 27 (2015).
Xie, "A novel Monte Carlo simulation procedure for modelling COVID-19 spread over time", Scientific Reports, pp. 1-9, vol. 10, Article 13120 (2020).
Xu et al., "Transmission routes of Covid-19 virus in the Diamond Princess Cruise ship", medRxiv 2020.04.09,.20059113; doi: https://doi.org/10.1101/2020.04.09.20059113.
Xu et al., "Fabrication of nanoperforated ultrathin TiO2 films by inkjet printing", Journal Materials Research, pp. 2151-2160, vol. 30, No. 14 (2015).
Xu et al., "Nanobodies from camelid mice and llamas neutralize SARS-CoV-2 variants", Nature, pp. 278-282, vol. 595 (2021).
Xu et al., "The ACE2/Angiotensin-(1-7)/Mas Receptor Axis: Pleiotropic Roles in Cancer", Frontiers in Physiology, pp. 1-8, vol. 8, Article 276 (2017).
Xu, et al., "Lessons and suggestions to travelers and cruise ships in the fight against COVID-19", QJM: An International Journal of Medicine, pp. 153-154, vol. 114, Issue 2 (2020).
Yamagishi et al., "Descriptive study of COVID-19 outbreak among passengers and crew on Diamond Princess cruise ship, Yokohama Port, Japan, Jan. 20 to Feb. 9, 2020", Euro Surveillance, pp. 1-8, vol. 25, No. 23 (2020).
Yamahata et al., "Preparation for Quarantine on the Cruise Ship Diamond Princess in Japan due to COVID-19", JMIR Public Health and Surveillance, e18821, in 8 pages, vol. 6, No. 2 (2020).
Yamashiro et al., A case of water intoxication with prolonged hyponatremia caused by excessive water drinking and secondary SIADH:, Case Reports in Nephrology and Urology, pp. 147-152, vol. 3, No. 2 (2013).
Yan et al., "Targeted cancer therapies", Chinese Journal of Cancer, pp. 1-4, vol. 30, No. 1 (2011).
Yang et al., "Cationic nanoparticles directly bind angiotensin-converting enzyme 2 and induce acute lung injury in mice", Particle and Fibre Toxicology, Biomed central, London, p. 4, vol. 12, No. 1 (Mar. 7, 2015).
Yang et al., "Angiotensin II Receptor Blockers and Angiotensin-Converting Enzyme Inhibitors Usage is Associated with Improved Inflammatory Status and Clinical Outcomes in COVID-19 Patients With Hypertension", medRxiv, (2020).
Yang et al., "Angiotensin-converting enzyme 2 (ACE2) mediates influenza H7N9 virus-induced acute lung injury", Scientific Reports, p. 1, vol. 4 (2014).
Yang et al., "Molecular interaction and inhibition of SARS-CoV-2 binding to the ACE2 receptor", Nature Communications, pp. 1-10 (2020).
Yang et al., "Non-invasive administration of AAV to target lung parenchymal cells and develop SARS-CoV-2-susceptible mice", Molecular Therapy, pp. 1994-2004, vol. 30, Issue 5 (2022).
Yang et al., "Structural basis for clonal diversity of the human T-cell response to a dominant influenza virus epitope", Journal of Biological Chemistry, pp. 18618-18627, vol. 292, Issue 45 (2017).
Yao et al., "Human H-ferritin presenting RBM of spike glycoprotein as potential vaccine of SARS-CoV-2", bioRxiv, 05.25 15618; doi: https://doi.org/10.1101/2020.05.25.115618 (2020).
Yeh et al., "Requirement for Casper (c-FLIP) in regulation of death receptor-induced apoptosis and embryonic development", Immunity, pp. 633-642, vol. 12, Issue 6 (2000).
Ylösmäki et al., "Novel personalized cancer vaccine platform based on Bacillus Calmette-Guèrin", Journal for Immunotherapy of Cancer, e002707, pp. 1-13, vol. 9, No. 7 (2021).
Yogev et al., "Genome wide screen of RNAi molecules against SARS-CoV-2 creates a broadly potent prophylaxis", bioRxiv. 488010; doi: https://doi.org/10.1101/2022.04.12.488010 (Posted Apr. 12, 2022).
Yu et al., "Design of Nanoparticle-Based Carriers for Targeted Drug Delivery", Journal of Nanomaterials, pp. 1-15, vol. 2016 (2016).
Yu et al., "Inhaled budesonide for COVID-19 in people at high risk of complications in the community in the UK (Principle): a randomised, controlled, open-label, adaptive platform trial", The Lancet, pp. 843-855, vol. 398, Issue 10303 (2021).
Yu et al., "Inkjet printed surface enhanced Raman spectroscopy array on cellulose paper" Analytical Chemistry, pp. 9626-9630, vol. 82, No. 23 (2010).
Yu, et al., "Auger parameters for sulfur-containing compounds using a mixed aluminum-silver excitation source", Journal of Electron Spectroscopy Related Phenomena, pp. 159-166, vol. 50, Issue 2 (1990).
Yuan et al., "Antitumor activity of tripterine via cell-penetrating peptide-coated nanostructured lipid carriers in a prostate cancer model", International Journal of Nanomedicine, pp. 4339-4350, vol. 8, Issue 1 (2013).
Yuan et al., "Mechanistic study of the covalent loading of paclitaxel via disulfide linkers for controlled drug release", Langmuir, pp. 734-743, vol. 29, No. 2 (2013).
Yue et al., "Surface Charge Affects Cellular Uptake and Intracellular Trafficking of Chitosan-Based Nanoparticles", Biomacromolecules, pp. 2440-2446, vol. 12, No. 7 (2011).
Zeisser-Labouèbe et al., "Screening of nanoparticulate delivery systems for the photodetection of cancer in a simple and cost-effective model", Nanomedicine (Lond), pp. 135-143, vol. 4, No. 2 (2009).
Zeng et al., "Hypertension in patients hospitalized with COVID-19 in Wuhan, China: A single-center retrospective observational study", medRxiv, pp. 1-31 (2020).
Zenker et al., "The coronavirus pandemic—A critical discussion of a tourism research agenda", Tourism Management, p. 104164, vol. 81 (2020).
Zhang et al., "Inhibition of Pathogen Adhesion by Bacterial Outer Membrane-Coated Nanoparticles", Angewandte Chenie International Edition, pp. 11404-11408, vol. 58, Issue 33 (Aug. 12, 2019).
Zhang et al., "A platform incorporating trimeric antigens into self-assembling nanoparticles reveals sars-cov-2-spike nanoparticles to elicit substantially higher neutralizing responses than spike alone", Scientific Reports, vol. 10, Article No. 18149 (2020).
Zhang et al., "Altered energy metabolism in cancer: a unique opportunity for therapeutic intervention", Cancer Biology & Therapy, pp. 81-89, vol. 14, No. 2 (2013).
Zhang et al., "Association of Inpatient Use of Angiotensin Converting Enzyme Inhibitors and Angiotensin II Receptor Blockers with Mortality Among Patients With Hypertension Hospitalized With COVID-19", Circulation Research, pp. 1671-1681, vol. 126, No. 12 (2020).

(56) References Cited

OTHER PUBLICATIONS

Zhang et al., "Enhanced radiation sensitivity in prostate cancer by gold-nanoparticles", Clinical and Investigative Medicine, pp. E160-E167 (2008).
Zhang et al., "Enhancement of oral bioavailability of tripterine through lipid nanospheres: preparation, characterization, and absorption evaluation", Journal of Pharmaceutical Sciences, pp. 1711-1719, vol. 103, Issue 6 (2014).
Zhang et al., "Inhalable nanocatchers for SARS-CoV-2 inhibition", Proceedings of the National Academy of Sciences of the United States of America, pp. 1-9, vol. 118, No. 29 (2021).
Zhang et al., "Nanoparticles That Reshape the Tumor Milieu Create a Therapeutic Window for Effective T-cell Therapy in Solid Malignancies", Cancer Research, pp. 3718-3730, vol. 78, Issue 13 (2018).
Zhang et al., "Self-assembly in the ferritin nano-cage protein superfamily", International Journal of Molecular Sciences, pp. 5406-5421, vol. 12, No. 8 (2011).
Zhang et al., "Site-specific N-glycosylation Characterization of Recombinant SARS-CoV-2 Spike Proteins", bioRxiv, pp. 1-37 (2020).
Zhang et al., "Zeta potential: a surface electrical characteristic to probe the interaction of nanoparticles with normal and cancer human breast epithelial cells", Biomedical Microdevices, pp. 321-328, vol. 10 (2008).
Zhao et al., "Microwave-induced polyol-process synthesis of copper and copper oxide nanocrystals with controllable morphology", European Journal of Inorganic Chemistry, pp. 4072-4080, No. 20 (2004).
Zhao et al., "Systematically benchmarking peptide-MHC binding predictors: From synthetic to naturally processed epitopes", PLoS Computational Biology, pp. 1-28, vol. 14 (2018).
Zheng et al., "Novel antibody epitopes dominate the antigenicity of spike glycoprotein in SARS-CoV-2 compared to SARS-CoV", Cellular & Molecular Immunology, pp. 536-538, vol. 17, No. 5 (2020).
Zhou et al., "A chelator-free multifunctional [64Cu]CuS nanoparticles platform for simultaneous micto-PET/CT imaging and photothermal ablation therapy", Journal of American Chemical Society, pp. 15351-15358, vol. 132, No. 43 (2010).
Zhou et al., "A pneumonia outbreak associated with a new coronavirus of probable bat origin", Nature, pp. 270-273, vol. 579 (2020).
Zhou et al., "Effects of human mobility restrictions on the spread of COVID-19 in Shenzhen, China: a modelling study using mobile phone data", The Lancet Digit Health, pp. e417-e424, vol. 2, No. 8 (2020).
Zhou et al., "Interferon-α2b Treatment for COVID-19", Frontiers in Immunology, pp. 1-6, vol. 11, No. 1061 (2020).
Zhou et al., "Mesoporous silica nanoparticles for drug and gene delivery", Acta Pharmaceutica Sinica B, pp. 165-177, vol. 8, No. 2 (2018).
Zhu et al., "Acute toxicities of six manufactured nanomaterial suspensions to Daphnia magna", Journal of Nanoparticle Research, pp. 67-75, vol. 11, No. 1 (2009).
Zhu et al., "Trophic transfer of TiO2 nanoparticles from Daphnia to zebrafish in a simplified freshwater food chain" Chemosphere, pp. 928-933, vol. 79, Issue 9 (2010).
Zhuk et al., "Advances in the Chemistry of Polyethyleneimine (Polyaziridine)", Russian Chemical Review, pp. 515-527, vol. 34, No. 7 (1965).
Zijlstra et al., "A quantitative analysis of rate-limiting steps in the metastatic cascade using human-specific real-time polymerase chain reaction", Cancer Research, pp. 7083-7092, vol. 62 (2002).
Zipeto et al., "HLA-C and HIV-1: Friends or foes?" Retrovirology, pp. 1-9, vol. 9, Issue 39 (2012).
Zou et al., "Tapping the Chinese market: An examination of Chinese tourists' images and constraints towards cruising", Tourism Review international, pp. 347-364, vol. 21, Issue 4 (2017).
Zuber et al., "COVID 19: challenges for virologists in the food industry", Microbial Biotechnology, pp. 1689-1701, vol. 13, Issue 6 (2020).
Zwicke et al., "Utilizing the folate receptor for active targeting of cancer nanotherapeutics." Nano Reviews, pp. 1-12, vol. 3, Issue 1 (2012).
Li et al., "Effects of Surface Roughness of Hydroxyapatite on Cell Attachment and Proliferation", Biotechnology & Biomaterials, pp. 2-6, vol. 2, Issue 6 (2012).
Monsigny et al., "Colorimetric Determination of Neutral Sugars by a Resorcinol Sulfuric Acid Micromethod", Analytical Biochemistry, pp. 525-530, vol. 175 (1988).
U.S. Appl. No. 17/735,010, filed May 2, 2022, Methods for Lowering the Infection Rate of Viruses.
U.S. Appl. No. 17/735,019, filed May 2, 2022, Particles for Stimulating an Immune Response Against Viral Infections.
Rabi et al., "Title", Pathogens, Mar. 20, 2020 vol. 9 p. 231.
Chen et al., "Crystal Structure of the Receptor-Binding Domain from Newly Emerged Middle East Respiratory Syndrome Coronavirus", Journal of Virology, pp. 10777-10783, vol. 87, No. 19, (Oct. 2013).
Ma et al., "Intranasal vaccination with recombinant receptor-binding domain of MERS-CoV spike protein induces much stronger local mucosal immune responses than subcutaneous immunization: Implication for designing novel mucosal MERS vaccines", Vaccine, pp. 2100-2108, vol. 32 (2014).

Immobilizing the Infectious Agent

SARS-CoV-2

Synthetic Nanoparticle

FIG. 3

Immobilizing the Infectious Agent by Blocking Circulating Co-receptors

SARS-CoV-2

SR-B1 Cholesterol

HDL

Synthetic Nanoparticle

SEQUENCE LISTING

<160> NUMBER OF SEQ ID NOS: 7

<210> SEQ ID NO 1
<211> LENGTH: 6
<212> TYPE: PRT
<213> ORGANISM: SARS-CoV-2

<400> SEQUENCE: 1

Tyr Lys Tyr Arg Tyr Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Potential alternative synthetic hexapeptide
      variant

<400> SEQUENCE: 2

Tyr Lys Tyr Asn Tyr Ile
1               5

<210> SEQ ID NO 3
<211> LENGTH: 6
<212> TYPE: PRT
<213> ORGANISM: Artificial Sequence
<220> FEATURE:
<223> OTHER INFORMATION: Potential alternative synthetic hexapeptide
      variant

<400> SEQUENCE: 3

Tyr Lys Tyr Asn Tyr Leu
1               5

<210> SEQ ID NO 4
<211> LENGTH: 28
<212> TYPE: PRT
<213> ORGANISM: SARS-CoV-2

<400> SEQUENCE: 4

Lys Lys Lys Lys Val Cys Glu Phe Gln Phe Cys Asn Asp Pro Phe Leu
1               5                   10                  15

Gly Val Tyr Tyr His Lys Asn Asn Lys Lys Lys Lys
            20                  25

<210> SEQ ID NO 5
<211> LENGTH: 223
<212> TYPE: PRT
<213> ORGANISM: SARS-CoV-2

<400> SEQUENCE: 5

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln

```
                      85                  90                  95
Thr Gly Lys Ile Ala Asp Tyr Asn Tyr Lys Leu Pro Asp Asp Phe Thr
            100                 105                 110
Gly Cys Val Ile Ala Trp Asn Ser Asn Leu Asp Ser Lys Val Gly
            115                 120                 125
Gly Asn Tyr Asn Tyr Leu Tyr Arg Leu Phe Arg Lys Ser Asn Leu Lys
            130                 135                 140
Pro Phe Glu Arg Asp Ile Ser Thr Glu Ile Tyr Gln Ala Gly Ser Thr
145                 150                 155                 160
Pro Cys Asn Gly Val Glu Gly Phe Asn Cys Tyr Phe Pro Leu Gln Ser
            165                 170                 175
Tyr Gly Phe Gln Pro Thr Asn Gly Val Gly Tyr Gln Pro Tyr Arg Val
            180                 185                 190
Val Val Leu Ser Phe Glu Leu Leu His Ala Pro Ala Thr Val Cys Gly
            195                 200                 205
Pro Lys Lys Ser Thr Asn Leu Val Lys Asn Lys Cys Val Asn Phe
            210                 215                 220
```

<210> SEQ ID NO 6
<211> LENGTH: 1273
<212> TYPE: PRT
<213> ORGANISM: SARS-CoV-2

<400> SEQUENCE: 6

```
Met Phe Val Phe Leu Val Leu Leu Pro Leu Val Ser Ser Gln Cys Val
1               5                  10                  15
Asn Leu Thr Thr Arg Thr Gln Leu Pro Pro Ala Tyr Thr Asn Ser Phe
            20                  25                  30
Thr Arg Gly Val Tyr Tyr Pro Asp Lys Val Phe Arg Ser Ser Val Leu
            35                  40                  45
His Ser Thr Gln Asp Leu Phe Leu Pro Phe Phe Ser Asn Val Thr Trp
            50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
            85                  90                  95
Lys Ser Asn Ile Ile Arg Gly Trp Ile Phe Gly Thr Thr Leu Asp Ser
            100                 105                 110
Lys Thr Gln Ser Leu Leu Ile Val Asn Asn Ala Thr Asn Val Val Ile
            115                 120                 125
Lys Val Cys Glu Phe Gln Phe Cys Asn Asp Pro Phe Leu Gly Val Tyr
            130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
            165                 170                 175
Met Asp Leu Glu Gly Lys Gln Gly Asn Phe Lys Asn Leu Arg Glu Phe
            180                 185                 190
Val Phe Lys Asn Ile Asp Gly Tyr Phe Lys Ile Tyr Ser Lys His Thr
            195                 200                 205
Pro Ile Asn Leu Val Arg Asp Leu Pro Gln Gly Phe Ser Ala Leu Glu
            210                 215                 220
Pro Leu Val Asp Leu Pro Ile Gly Ile Asn Ile Thr Arg Phe Gln Thr
225                 230                 235                 240
```

```
Leu Leu Ala Leu His Arg Ser Tyr Leu Thr Pro Gly Asp Ser Ser
            245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

```
                660                 665                 670
Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                1000                1005

Thr Gln Gln Leu Ile Arg Ala Ala Glu Ile Arg Ala Ser Ala Asn
            1010                1015                1020

Leu Ala Ala Thr Lys Met Ser Glu Cys Val Leu Gly Gln Ser Lys
            1025                1030                1035

Arg Val Asp Phe Cys Gly Lys Gly Tyr His Leu Met Ser Phe Pro
            1040                1045                1050

Gln Ser Ala Pro His Gly Val Val Phe Leu His Val Thr Tyr Val
            1055                1060                1065

Pro Ala Gln Glu Lys Asn Phe Thr Thr Ala Pro Ala Ile Cys His
            1070                1075                1080
```

-continued

```
Asp Gly Lys Ala His Phe Pro Arg Glu Gly Val Phe Val Ser Asn
1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270
```

<210> SEQ ID NO 7
<211> LENGTH: 272
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(49)
<223> OTHER INFORMATION: Different Expression Cassette - Signal
      Sequence - Tag - Spacer; X is any amino acid

<400> SEQUENCE: 7

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Arg Val Gln Pro Thr Glu Ser Ile Val Arg Phe Pro Asn Ile Thr
50                  55                  60

Asn Leu Cys Pro Phe Gly Glu Val Phe Asn Ala Thr Arg Phe Ala Ser
65                  70                  75                  80

Val Tyr Ala Trp Asn Arg Lys Arg Ile Ser Asn Cys Val Ala Asp Tyr
                85                  90                  95

Ser Val Leu Tyr Asn Ser Ala Ser Phe Ser Thr Phe Lys Cys Tyr Gly
            100                 105                 110

Val Ser Pro Thr Lys Leu Asn Asp Leu Cys Phe Thr Asn Val Tyr Ala
        115                 120                 125
```

```
Asp Ser Phe Val Ile Arg Gly Asp Glu Val Arg Gln Ile Ala Pro Gly
    130                 135                 140

Gln Thr Gly Lys Ile Ala Asp Tyr Asn Tyr Lys Leu Pro Asp Asp Phe
145                 150                 155                 160

Thr Gly Cys Val Ile Ala Trp Asn Ser Asn Asn Leu Asp Ser Lys Val
                165                 170                 175

Gly Gly Asn Tyr Asn Tyr Leu Tyr Arg Leu Phe Arg Lys Ser Asn Leu
                180                 185                 190

Lys Pro Phe Glu Arg Asp Ile Ser Thr Glu Ile Tyr Gln Ala Gly Ser
        195                 200                 205

Thr Pro Cys Asn Gly Val Glu Gly Phe Asn Cys Tyr Phe Pro Leu Gln
    210                 215                 220

Ser Tyr Gly Phe Gln Pro Thr Asn Gly Val Gly Tyr Gln Pro Tyr Arg
225                 230                 235                 240

Val Val Val Leu Ser Phe Glu Leu Leu His Ala Pro Ala Thr Val Cys
                245                 250                 255

Gly Pro Lys Lys Ser Thr Asn Leu Val Lys Asn Lys Cys Val Asn Phe
            260                 265                 270
```

VIRUS-LIKE PARTICLES FOR PREVENTING THE SPREADING AND LOWERING THE INFECTION RATE OF VIRUSES

CROSS-REFERENCE TO RELATED APPLICATIONS

This application is a continuation-in-part (CIP) of PCT Application PCT/FI2021/050259, filed Apr. 9, 2021 and published on Oct. 14, 2021 as PCT Publ. WO 2021/205077, which claims priority to Finnish Application Nos. 20205382, filed Apr. 9, 2020 and 20215182, filed Feb. 19, 2021. The contents of each of the aforementioned applications are incorporated by reference herein in their entireties and made part of the present application.

INCORPORATION BY REFERENCE OF MATERIAL IN ASCII TEXT FILE

This application incorporates by reference the Sequence Listing contained in the following ASCII text file being submitted concurrently herewith: File name: FICU.002P1_ST25.txt; created on May 19, 2022 and is 16,778 bytes in size.

BACKGROUND

Field

The present application pertains to the field of pharmaceutical products, biologics, medical devices, over-the-counter drugs and consumer products preventing or reducing the spread of pathogens, such as, for example, coronaviruses (e.g., the Severe Acute Respiratory Syndrome Coronavirus 2 (SARS-CoV-2)), influenzas and viruses causing respiratory infection, diarrhea, common cold, cytokine storm, general discomfort and/or death, bacteria, other pathogens and the like. More specifically, the present application relates to nano- and/or micromaterials-based carriers, such as mimetic nano- and/or micromaterials-based carriers, synthesized to minimize the spread of pathogens and infectious agents (e.g., viruses (e.g., influenzas, rhinoviruses, noroviruses, respiratory syncytial virus (RSV), SARS-CoV-2, future strains and/or types of coronaviruses derived thereof, etc.), bacteria, parasites, antigens, prions, mold, fungi, toxins, poisons, and allergens.

The present application also relates to combinatory tailored treatments of an active pharmaceutical ingredient ("API") loaded inside a carrier system capable of delivering the drug specifically to target cells and/or tissues. More specifically this application pertains to the fabrication and use of man-made materials in the nano- and/or microscale that would, at least partially, saturate and bind to receptors, proteins and/or macromolecules at the cellular level in order to prevent and/or minimize (or reduce the likelihood of) pathogen binding, in particular, for example, novel coronaviruses binding and entry to the host target cells and/or tissues by competitive inhibition.

The present application further relates to a medical device or delivery device capable of releasing (e.g., on-demand, specific amounts of) the synthesized carrier system to targeted tissue or tissues susceptible to for example coronaviruses. In some embodiments, for example, such a device includes an inhalation device, e.g., meter dose, dry inhaler, nebulization, ultrasonication, nose or mouth drops, or a nasal spray for the respiratory tract. In some arrangements, the device includes tailored orally ingestible tablets or solutions for the gastrointestinal tract, a topically administrable cream or ointment intended to be applied to a subject's skin and/or an injectable substance intended to be applied subcutaneously, intravenously, intraperitoneally or otherwise injected and/or administered using, at least in part, for example, high pressure or laser.

Further, the present application relates to synthesized materials that have the capacity and ability of binding and encapsulating pathogens or pathogens co-receptors and natural occurring carriers for, at least partially, immobilizing and neutralizing the infectious agent for disrupting the infectious agent. Therefore, according to some embodiments, the carrier system described herein is configured to reduce the likelihood of infection of host cells by (1) blocking receptors and/or other binding sites/features of host cells to which viruses and/or other pathogens may bind (e.g., for entry into host cells), (2) delivering immune stimulating properties to target cell populations, and/or (3) immobilizing viruses and/or other pathogens by attracting virus and/or other pathogens (e.g., so such viruses and/or other pathogens are unable to bind to host cells).

Background

Different pathogens (e.g., viruses, bacterium, parasites, etc.) prefer environments typical of their specific niche inside the host tissues. For example, *Escherichia. coli* prefers to colonize the intestine, whereas tuberculosis residues in the lungs of its host [1]. Malaria-bearing mosquitos may infect their human host by biting allowing parasites to enter the blood stream and travel to the liver of the subject for maturation [2]. For the pathogens to colonize and replicate at their specific environments and tissues, they need to infect and/or inoculate their host [1-4]. At the cellular level, this mechanism of entry starts by the pathogen binding or getting in proximity of the host cell where specific receptors, macromolecules and/or proteins protruding at the cell membrane facilitates the endocytosis of the infectious agent. If the specific route of entry is known, such knowledge can be used for creating a man-made object that can allosterically hinder the specific pathogens entry by competitive inhibition [5]. For example, by creating a carrier (e.g., nanoparticle), such as a mimetic nanoparticle, of similar size, surface chemistry and charge as the pathogen of interest, it is possible to saturate and block the specific receptors at the host cells hindering the pathogens entry. Another possibility includes synthetizing man-made materials (e.g., carriers) that would efficiently bind to the pathogen of interest encapsulating and immobilizing the infectious agent, thereby minimizing the possible entry to the host. Another possibility includes synthetizing man-made materials (e.g., carriers) that would efficiently bind to the pathogen, such as the novel coronavirus and/or co-receptor of interest, thereby immobilizing the infectious agent and reducing the likelihood (e.g., minimizing) the possible spread of the disease further inside the body and/or reducing the likelihood (e.g., preventing) entry to the host.

Viruses use components derived from their host for cell entry. For example, the SARS-CoV-2 virus that causes a respiratory infection called COVID-19 is decorated by glycoprotein spikes at the surface of the viral particle. These glycoproteins have high affinity for the human angiotensin converting enzyme 2 (ACE-2) allowing for specific internalization of the virus in the epithelial cells of the respiratory tract, possible intestinal tract and/or another tract or system of a subject where there is high expression of its target receptor [3,4]. Thus, potentially allowing for tailored molecules to be used for intervention of the SARS-CoV-2 virus enter to its human host. In bacterium it has been shown that surface topography together with surface charge greatly influences adhesion that modulates bacterial growth [6]. Using nanostructured surfaces, it could be possible to control bacterial adhesion and growth that could be used in medical applications for preventing infections. *Plasmodium falciparum*, which is the human Malaria parasites, uses dynamin like Eps15 homology domain-containing proteins for hijacking the endocytosis pathways important for infecting more erythrocytes in its host [2].

For example, the novel coronavirus SARS-CoV-2, that causes a respiratory infection called Coronavirus Disease 2019 (COVID-19), are decorated by glycoprotein spikes at the surface of the viral particle having high affinity for specific receptor(s). SARS-CoV-2, SARS-CoV and MERS-CoV belong to the betacoronavirus genus having a genome size of approximate 30 kilobases encoding both structural and non-structural proteins. To the structural proteins include the envelope (E) protein, spike (S) glycoprotein, the nucleocapsid (N) protein and the membrane (M) protein, whereas to the non-structural proteins belong, for example, the RNA-dependent RNA polymerase. The spike (S) glycoproteins decorated on coronaviruses consist of a homotrimeric transmembrane protein, each 180 kDa monomer comprising two functional subunits S1 and S2, whereas the S1 unit consists of two domains: N-terminal domain (NTD) and C-terminal domain (CTD). Depending on the coronavirus type, either the NTD or CTD of S1 is used as the receptor binding domain (RBD) capable of binding to specific receptors at the host cell surface. Each of SARS-CoV-2 and SARS-CoV utilizes the CTD as its RBD for the human angiotensin converting enzyme 2 (ACE2) allowing for specific internalization of the virus in the epithelial cells of the respiratory tract and possible intestine where there is high expression of its target receptor [3,4,6]. However, due to the novel amino acid sequence and structure of SARS-CoV-2, the affinity for the ACE2 receptor is significantly higher compared to SARS-CoV [6,7]. In both of the aforementioned coronaviruses, the RBD forms a concave surface that contains a ridge loop that has the ability to bind to the receptor binding motif, which is the outer surface of the human ACE2 receptor at its N-terminal helix. In SARS-CoV, this loop contains a three-residue motif proline-proline-alanine, and these prolines repeats makes the ridge loop to make a sharp and short turn. SARS-CoV-2 has a four-residue motif of glycine-valine/glutamine-glutamate/threonine-glycine that give rise to two bulkier residues and two flexible glycine residues that creates a different and compact conformation, allowing the viral loop to be closer to the ACE2 receptors N-terminal helix forming additional hydrogen bonds between the loop and the human receptor resulting in a stronger binding [6]. The S2 subunit from the S protein is necessary for viral fusion with the host cellular membrane mediated by proteolytic cleavage by the human transmembrane serine protease 2 (TMPRSS2), leading to the internalization of SARS-CoV-2, enabling viral replication inside its host cell [7]. The inhibitory effect of RBD spike fragment hexapeptide 438YKYRYL443 (SEQ ID No: 1) of the SARS-CoV-2 has been estimated to have the highest affinity for ACE2 when compared to another known coronavirus derived hexapeptides. The specific hexapeptide YKYRYL (SEQ ID No: 1) carries the dominant binding amino acid sequence that binds to ACE2 with a high affinity of KD=46 μM. However, the simulation gives rise to potential alternative synthetic hexapeptide variants YKYNYI (SEQ ID No: 2) and YKYNYL (SEQ ID No: 3) with even stronger binding affinity towards the ACE2 receptor which is highly conserved among different mammalian organisms allowing transmission from animals to humans and vice versa [8]. There are variations among human populations and the animal kingdom regarding the ACE2 receptor in terms of expression levels and polymorphisms that could influence the susceptibility of SARS-CoV-2 and outcome of COVID-19 disease [6-10]. Thus, potentially allowing for tailored molecules to be used for intervention of the SARS-CoV-2 virus enter to its human and animal hosts.

In the context of this specification, both ACE2 and ACE-2 may be understood as referring to human angiotensin converting enzyme 2.

Influenza, rhinoviruses, coronaviruses, respiratory syncytial virus (RSV) and noroviruses are non-limiting examples of viruses causing respiratory infection, diarrhea, common cold, cytokine storm, general discomfort, death and/or other symptoms or ailments. For example, influenza virus is a negative-sense, single-stranded RNA that causes a respiratory infection commonly called the "flu" which affects millions of individuals annually and causes thousands of deaths and millions of hospitalizations. The flu viral envelope is decorated with the fusion protein hemagglutinin (HA) that binds to the host sialic acid receptors and neuraminidase (NA), an enzyme located at the viral surface that cleaves the glycosidic bonds of the monosaccharide sialic acid, aiding in penetrating the host mucus and enabling the escape of newly formed viral particles. The size of influenza virus particles is around 80-120 nm, which is quite close to the size of coronaviruses. However, influenzas differ by having two main proteins on the surface, i.e., HA and NA, whereas coronaviruses only have the spike proteins protruding on the surface. To further complicate matters, there are currently 17 different HA proteins and 10 different NA proteins that have been characterized. It is these different combinations of proteins that give influenzas their subtype names. For example, the sequence homology of the HA2 subunit compared to the other HA subtypes is around 51-80%, whereas the HA1 subunit has an 34% to 59% sequence homology, rendering different genetic and protein varieties between the influenza subtypes. Combining the genetic variation with the potential protein combination of these viruses contributes to the immune evasive properties of influenzas, rendering efficacious vaccination development to a difficult task. This limited protection against influenzas, induced by vaccination, is listed by the Center for Disease Control (CDC) as follows, "flu vaccination reduces the risk of flu illness by between 40% and 60% among the overall population." Therefore, there exists a significant need for developing anti-viral compounds and broad immune stimulating influenza vaccines in order to mitigate the spreading of the flu.

Rhinoviruses is one category of other major causative agents for the common cold, and there is currently no efficient vaccination against these types of viruses. Human Rhinoviruses (HRV) belong to the picornavirus family and are positive-sense, single-stranded ribonucleic acid (RNA) viruses that have an icosahedral symmetry with a particle size of around 30 nm. The viral capsid is composed of four main proteins: VP1, VP2, VP3, and VP4, whereas the VP4 protein is located inside of the virus anchoring the genetic information to the capsid structure. There are over 150 different serotypes of HRVs with the two most common types being HRV-A and HRV-B that uses the intercellular adhesion molecule-1 (ICAM-1) as the cell receptor for entering the host. However, some of the HRV serotypes use heparin sulfate proteoglycan as an additional receptor, and there are around 10 serotypes that use low-density lipoprotein as the cell receptor. Additionally, a new serotype of HRVs that arose in 2002 was given the name HRV-C, having a route of cell entry still remains elusive rendering rhinoviruses to a difficult task to mitigate.

Respiratory syncytial virus (RSV) belongs to the family of paramyxoviridae viruses and are negative-sense, single-stranded RNA viruses that usually cause a mild cold in most healthy humans. However, for infants, the elderly and/or other humans that are immunocompromised or otherwise susceptible to disease, the RSV can cause a more serious disease such as bronchiolitis and pneumonia, oftentimes leading to hospitalization. The RSVs have an average size of around 200 nm and contain three membrane proteins: 1) the host receptor attachment protruding glycoprotein (G), 2) the fusion protein (F), and 3) a short hydrophobic (SH) protein that forms a ion channel. RSVs can be further divided into two groups, A and B, depending on the reaction with monoclonal antibodies directed against the F and G proteins. The A group is the most prevalent circulating virus, and the largest genetic divergence is associated with the gene encoding for the G protein, rendering this protein to the most variable protein of the virus. This diverse variation of proteins explains, at least partially, why no effective vaccination against RSV currently exists on the market. Noroviruses (NoV) belong to the family Caliciviridae, which are genetically a diverse group of single-stranded positive-sense RNA that are non-enveloped viruses that cause an infection commonly called gastroenteritis or "stomach flu," giving sudden onset of vomiting, diarrhea and other symptoms, which are often relatively severe. The most common symptoms for norovirus include nausea, vomiting, stomach pain or cramps, diarrhea, fever and/or muscle pain, with early symptoms usually beginning about 12 to 48 hours after exposure to the virus. Such symptoms can last up to several days. Infected individuals may continue to shed noroviruses in their feces for several weeks after recovery, thereby transmitting the disease without knowing to other individuals. The norovirus consists of an ~7.7-kb RNA genome with three open reading frames (ORFs), where ORF1 encodes a polyprotein precursor which is processed into several non-structural proteins, and where the two other ORFs encode the major (VP1) and minor (VP2) capsid proteins. The viral particles are around 27-30 nm in diameter having an icosahedral symmetry where the viral capsid is built of 90 dimers consisting of VP1, each protein having a shell (S) domain and a protruding (P) domain connected by a flexible linker. The S domain is responsible for the assembly of the virus capsid shell encapsulating the viral genome and is highly conserved domain of the VP1 protein. The P domain, on the other hand, is more variable and includes a P1 and a P2 subdomain. The P1 subdomain binds the S domain with the P2 domain, and the P2 subdomain contains the host receptor binding site which is also a target for neutralizing antibodies. The norovirus enters its host by binding to cell-associated glycans located on the cell membranes, including sialic acid and histo-blood group antigens. Then soluble cofactors facilitate viral binding to its host receptor. For murine norovirus (MNoVv), the receptor is a CD300lf an immunoglobulin (Ig) domain-containing membrane protein, whereas for the feline calicivirus (FCV), the receptor is a feline junctional adhesion molecule A (fJAM-A). However, the receptor for the human norovirus (HNoV) remains elusive. Taking together the highly variable P2 domain in combination of the VP1 protein's ability to inhibit cytokine induction and VP2 protein's capability of regulating antigen presentation and the complex transmission routes makes noroviruses challenging pathogens to combat.

Although vaccines can be effective in protecting against infectious agents, often take significant time and resources to develop. For example, effective vaccines that can safely be administered to patients require many clinical tests that need to be performed before approval. Secondly, vaccinations only work if the correct antigens for the specific pathogen are being administered with sufficient immunological reaction, creating an immunity for the specific disease [11]. For example, seasonal influenza strains normally vary from one year to the next, and the vaccines usually contain only a few epitopes of different influenza strains, thereby rendering the creation of some vaccinations to an educated guess work.

Anti-viral medicine can also be effective against viral infections if treated correctly. However, these medications often interrupt viral DNA or RNA replication machinery, and thus, it is not always plausible to use such medicines as a proactive drug. Unfortunately, these compounds can be harmful for the patient if used under prolonged periods [12]. Antibiotics are effective against the spread of bacteria by disrupting their cell division and/or the synthesis of the proteoglycan-based cell wall [1]. Formulating the most efficient antibiotic depends on if the target bacterium is gram positive (having a cell wall) or gram negative (lacking a cell wall). Recently, there have been numerous cases were multi-resistant bacteria have emerged that are not responding to traditional antibiotics. In these cases, broad spectrum antibiotics have been used to combat infection. However, such strong cocktails of antibiotics can take their toll on the patient and potentially can give rise to more antibiotic resistance bacteria [1]. Therefore, there is an unmet need of developing medications, such as over-the-counter (OTC) drugs and consumer products, that can be used for preventing or reducing the likelihood of the spread of pathogens, including mutating novel coronaviruses, using proactive purposes and having minimal or minor side effects. Also, the use of tailored medicine using carriers (e.g., nanomaterials) loaded with an active pharmaceutical ingredient (API) for both inhibiting the endocytosis of the target pathogen, in particular viruses, as well as stopping the replication of already infected cells and/or tissues.

Protein and proteasome inhibitors show great potential as these compounds can specificity bind and allosterically hinder the enzymatic reaction by binding to the active site blocking the target molecules interaction with the enzyme [13]. However, one of the major drawbacks of proteasome inhibitors is their instability and possible low solubility. Further, due to their high specificity, such molecules often only shows efficacy to only a few or one specific enzyme per drug molecule.

Monoclonal antibodies have been used in since 1986. The first such drug approved by the FDA was Orthoclone OKT3, which is used for reducing kidney rejection after transplantation. Monoclonal antibodies that are used in cancer therapeutics include trastuzumab (Herceptin), which is a drug that binds to the human epidermal growth factor receptor 2 (HER2) slowing down the growth of malignant HER2 positive breast cancer cells [14]. The major limitation of antibody-based therapeutics is that these proteins are foreign. For example, such therapeutics are produced in mice or other animals so when they are introduced to patients, they can invoke an immunologic reaction, potentially giving adverse reaction of the treatment.

Nanomedicine shows great potential in the field of targeted drug delivery, where nanotechnology and medicine are combined for the development of personalized diagnostics, as well as the treatment and prevention of different diseases. In some arrangements, nanomaterials or other carriers include man-made and/or naturally occurring objects with dimensions between 0.2 nm to 100 nm. The physical properties of such materials can be drastically different compared to their bulk counterpart. For example, nanomaterials can be more reactive on both biological and chemical substances due to higher surface area to volume ratio. Functionalized nanoparticles have shown to be able to target specific cell types opening the possibility of targeted drug delivery lowering the off-target effects [15]. Combing these different fields, it would be possible to develop a carrier (e.g., a synthetic particle or object) that mimics the pathogen or pathogens of interest (e.g., viruses, bacteria, other pathogens, etc.) in order to hinder the spread of the disease by competitive inhibition. Further, such carriers can be used to advantageously deliver the appropriate API, drug, molecule and/or other substance or material to the target tissues with increased efficacy and minimal or reduced side effects.

SUMMARY

According to some embodiments, a carrier for reducing a likelihood of a pathogen binding to cell structures of a host comprises a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen from binding to said target areas as a result of competitive inhibition, and wherein the surface features at least partially physically mimic naturally-occurring protrusions of the pathogen, and wherein the surface features are configured to comprise immune stimulating properties. The carrier further comprises a plurality of binding sites along the exterior surface, wherein the binding sites are configured to attract at least one portion of the pathogen, wherein the binding sites are configured to at least partially mimic binding sites of the cell structures of the host, wherein the binding sites are recognizable by the pathogen and are able to be bound by the pathogen, thereby at least partially immobilizing the pathogen and reducing the likelihood of the pathogen binding to target areas of cell structures of the host, and wherein a size of the carrier is in the nanometer to micrometer range (e.g., in the nanometer or micrometer range).

According to some embodiments, the pathogen comprises a virus. In some embodiments, the virus includes one or more of the following: a coronavirus, SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the naturally-occurring protrusions of the pathogen comprise proteins at the surface of the viral exterior.

According to some embodiments, the carrier is sized, shaped or otherwise configured to reach targeted portions of the host that are susceptible to infection by the pathogen. In some embodiments, the targeted portions of the host that are susceptible to infection by the pathogen comprise the lungs or other area of the host's upper or lower respiratory tract.

In some embodiments, the carrier is configured to be delivered via the respiratory tract of the host to the targeted portions of the host that are susceptible to infection by the pathogen.

According to some embodiments, the carrier comprises at least one coating that improves a binding affinity of the carrier to the pathogen relative to a binding affinity of the cell structures of the host to the pathogen.

According to some embodiments, the carrier further comprises at least one component positioned at least partially on and/or within carrier. In some embodiments, the at least one component comprises a pharmaceutical agent (e.g., API). In some embodiments, the pharmaceutical agent comprises at least one of an anti-viral compound, a nucleic acid and an RNA or DNA sequence According to some embodiments, a carrier for reducing a likelihood of a pathogen binding to cell structures of a host comprises a core, surface features extending from an exterior surface of the core, wherein the surface features are configured to bind to target areas of cell structures of the host to at least partially block the pathogen from binding to said target areas as a result of competitive inhibition, and wherein the surface features comprise immune stimulating properties. The carrier further comprises a plurality of binding sites along the exterior surface, wherein the binding sites are configured to attract at least one portion of the pathogen, wherein the binding sites are configured to at least partially mimic binding sites of the host, and wherein the binding sites are recognizable by the pathogen and are able to be bound by the pathogen, thereby at least partially immobilizing the pathogen and reducing the likelihood of the pathogen binding to target areas of cell structures of the host.

According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the carrier is sized, shaped and otherwise configured to reach targeted portions of the host that are susceptible to infection by the pathogen, the targeted portions of the host that are susceptible to infection by the pathogen comprise the lungs or other area of the host's respiratory tract.

According to some embodiments, the carrier is configured to be delivered via a respiratory tract of the host to the targeted portions of the host that are susceptible to infection by the pathogen.

According to some embodiments, the carrier further comprises at least one component positioned at least partially on and/or within carrier (e.g., an anti-viral compound, a nucleic acid, an RNA or DNA sequence and another pharmaceutical agent, etc.).

According to some embodiments, a carrier for reducing a likelihood of a pathogen binding to cell structures of a host comprises a core, surface features extending from an exterior surface of the core, wherein the surface features are configured to bind to target areas of cell structures of the host to at least partially block the pathogen from binding to said target areas as a result of competitive inhibition, and a plurality of binding sites along the exterior surface, wherein the binding sites are configured to attract at least one portion of the pathogen, wherein the binding sites are recognizable by the pathogen and are able to be bound by the pathogen, thereby at least partially immobilizing the pathogen and reducing the likelihood of the pathogen binding to target areas of cell structures of the host. According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus. According to some embodiments, the pathogen comprises a bacterium, a parasite, an antigen, a prion, a mold, a fungus or an allergen. According to some embodiments, the carrier is sized, shaped and otherwise configured to reach targeted portions of the host that are susceptible to infection by the pathogen, the targeted portions of the host that are susceptible to infection by the pathogen comprise the lungs or other area of the host's respiratory tract. According to some embodiments, the carrier is configured to be delivered via a respiratory tract of the host to the targeted portions of the host that are susceptible to infection by the pathogen. According to some embodiments, the carrier further comprises at least one component positioned at least partially on and/or within carrier (e.g., an anti-viral compound, a nucleic acid, an RNA or DNA sequence and another pharmaceutical agent, etc.).

According to some embodiments, a method of reducing a spread of pathogens within a host comprises at least partially blocking pathogens from binding to said target areas as a result of competitive inhibition by delivering a carrier to the host, wherein the carrier comprises a core, surface features extending from an exterior surface of the core, and a plurality of binding sites along the exterior surface, and at least partially immobilizing pathogens and reducing the likelihood of pathogens binding to target areas of cell structures of the host by binding the carrier to at least one of the pathogens, wherein the surface features are configured to bind to target areas of cell structures of the host, wherein the surface features at least partially physically mimic naturally-occurring protrusions of the pathogen, wherein the surface features are configured to comprise immune stimulating properties, wherein the binding sites are configured to attract at least one portion of the pathogen, wherein the binding sites are configured to at least partially mimic binding sites of the cell structures of the host, and wherein, and wherein the binding sites are recognizable by the pathogen and are able to be bound by the pathogen.

According to some embodiments, the pathogen comprises a virus. In some embodiments, the virus includes one or more of the following: a coronavirus, a SARS-CoV-2 virus, an influenza virus, a rhinovirus, a norovirus, a respiratory syncytial virus (RSV), another virus that impacts the respiratory system and any other type of virus.

According to some embodiments, the pathogen comprises a bacterium, a parasite, an antigen, a prion, a mold, a fungus or an allergen.

According to some embodiments, the carrier is sized, shaped and otherwise configured to reach targeted portions of the host that are susceptible to infection by the pathogen, the targeted portions of the host that are susceptible to infection by the pathogen comprise the lungs or other area of the host's respiratory tract.

According to some embodiments, the carrier is configured to be delivered via a respiratory tract of the host to the targeted portions of the host that are susceptible to infection by the pathogen.

According to some embodiments, the carrier further comprises at least one component positioned at least partially on and/or within carrier (e.g., an anti-viral compound, a nucleic acid, an RNA or DNA sequence and another pharmaceutical agent, etc.).

According to some embodiments, a carrier for reducing a likelihood of a pathogen binding to cell structures of a host, the carrier comprising a core having an exterior surface, a plurality of surface features extending from the exterior surface of the core, wherein the surface features are configured to bind to target areas of cell structures of the host, wherein binding of the carrier to at least one of the target areas of cell structures of the host is configured to at least partially block the pathogen from binding to said target areas as a result of competitive inhibition, wherein the surface features are configured to at least partially physically mimic naturally-occurring protrusions of the pathogen, and wherein the surface features are configured to comprise immune stimulating properties, and a plurality of binding sites along the exterior surface, wherein the binding sites are configured to attract at least one portion of the pathogen, wherein the binding sites are configured to at least partially mimic binding sites of the cell structures of the host, wherein the binding sites are recognizable by the pathogen and are able to be bound by the pathogen, thereby at least partially immobilizing the pathogen and reducing the likelihood of the pathogen binding to target areas of cell structures of the host, and wherein a maximum cross-sectional dimension of the carrier in at least one dimension is in the nanometer to micrometer range (e.g., in the nanometer or micrometer range).

It is an aim of the present application to control and hinder (e.g., slow or prevent) the spread of pathogens and other infectious agents, e.g., viruses, bacteria, parasites, antigens, proteins, prions, toxins, allergens, other substances that are foreign and/or potentially harmful and the like. Specifically, the application provides ways of targeting viruses, such as, for example, influenzas, rhinoviruses, noroviruses, respiratory syncytial virus (RSV), coronaviruses (e.g., SARS-CoV-2, future mutated strains derived from a coronavirus, etc.) and the like, that could otherwise give rise to disease, infections or allergic reactions in the host.

It is an aim of the inventions disclosed herein to decrease the risk of infection (or at least decrease the spread of infection if a host has been infected) by a pathogen or pathogens. As such, various embodiments disclosed herein can be helpful combatting infection and any resulting symptoms and other consequences (e.g., respiratory infection, diarrhea, common cold, cytokine storm, other inflammatory reactions, general discomfort, intubation, other symptoms, death, etc.). Accordingly, various embodiments disclosed herein are configured to, at least partially, resist and otherwise combat the effects of contracting the COVID-19 disease caused by SARS-CoV-2 (e.g., via entry of the virus into a host for a temporary or prolonged duration), to give a targeted treatment for the specific disease caused by the infectious agent, to provide one or more additional benefits or advantages, etc.

Further, it is an aim of the inventions disclosed in the present application to provide a method for preventing the spreading and/or for lowering the infection rate of pathogens, such as SARS-CoV-2, influenzas, rhinoviruses, noroviruses, respiratory syncytial viruses (RSVs) and/or the like, by, at least in part, competitive inhibition using synthesized carriers (e.g., nanomaterials, particles, objects, etc.).

Thus, in one aspect, the inventions disclosed herein include carriers (e.g., synthesized nano- or micro sized materials) that mimic, at least partially, the pathogen or pathogens of interest, such as coronaviruses (e.g., SARS- CoV-2), influenzas, rhinoviruses noroviruses, respiratory syncytial viruses (RSVs) and other viruses (e.g., viruses capable of causing respiratory infection) using surface functionalization to hinder or otherwise lower the likelihood of the infectious agent entering the host. In some embodiments, carriers can be used to target pathogens other than viruses, including without limitation, bacteria, parasites, antigens, prions, mold, fungi, toxins, poisons, and allergens. In some embodiments, this is accomplished, at least in part, by competitive inhibition (e.g., at the cellular level).

It is another aim of the inventions disclosed in the present application to create a carrier (e.g., man-made particle, object, material, etc.) that efficiently binds to the pathogen(s) of interest (e.g., coronavirus) and/or circulating co-receptors (e.g., high-density lipoprotein (HDL) receptor in the blood and other secondary receptors such as the FcγR that affects SARS-CoV-2 infection dynamics by antibody-mediated enhancement (ADE)). Thus, in some embodiments, the carrier at least partially encapsulates and/or immobilizes the pathogen or other infectious agent and at least partly hinders the receptor mediated viral entry. In some embodiments, the carrier is configured to at least partially inhibit the infectious agent's reproduction capabilities, thereby reducing the spread of said host organism. In some embodiments, the carrier makes it easier for the host body to identify, engulf and/or filter the macromolecule holding the pathogen, resulting in elimination or neutralization of the infectious agent.

A synthetic carrier can be used to at least partially prevent or reduce infection of a host by one or more pathogens, such as, for example, influenzas, rhinoviruses, noroviruses, respiratory syncytial viruses (RSVs), corona viruses (e.g., SARS-CoV-2), other viruses or pathogens. In some embodiments, the carrier is configured to bind to target areas of cell surfaces of a host. For example, the carrier can bind to ACE2 receptors, TMPRSS2 receptors, sialic acid, histo-blood group antigens, ICAM-1, IGF1R receptors, intracellular or extracellular receptors, other receptors, or combination of receptors and/or any other portion of the cell structures of the host that may be susceptible to the pathogen. According to some embodiments, a carrier is formed by biocompatible particles having a maximum size in at least one dimension in the nanometer or micrometer range (e.g., a core of the carrier includes a maximum size in at least one dimension in the nanometer or micrometer range). Further, a functionalized surface can be formed on or along a core of the carrier that is capable of binding to said target areas of the cell surfaces of the host to at least temporarily and/or at least partially block the target areas, thereby, at least partially, preventing or minimizing pathogen binding and internalization. Accordingly, the risk of the host being infected or contracting a disease caused by said pathogen, such as a virus, can be beneficially reduced.

In an aspect, the present application provides for loading of synthetic particles (e.g., carriers) with API or molecules, such as for example and without limitation, Celastrol, anti-viral drugs, Zinc and/or immune stimulating molecules such as, for example, Interferon-Gamma modulators alternatively administering RNA vectors encoding Interferon-Gamma producing said protein in the host, anti-viral compounds that prevent the spread of (and/or hinder the replication of) the targeted pathogen or pathogens (e.g., coronavirus, influenzas, rhinovirus, noroviruses, respiratory syncytial virus, etc.) inside the host body and/or the like.

It is another aim of the inventions disclosed in the present application to provide a medical device capable of delivering the synthetized carrier, particle, object or other material (e.g., on-demand by the patient or other user). For example, in some embodiments, such a medical device comprises an inhalation device, an aerosol, a spray, eye or oral drops, an intravenous injection, a tablet, a topically applicable cream, an ointment or other material.

It is another aim of the inventions disclosed in the present application to provide a medical countermeasure similar to that of chelating agents used in toxifications of metal complexes (e.g., arsenic poisoning, snake venoms, mold toxins, etc.) [16]. In some embodiments, the present inventions provide a functionalized nanomaterial or carrier, which, in some configurations, is effectively an antidote capable of binding toxic components of a specific virus to larger entities that can be metabolized, degraded or secreted from the body and/or capable of binding to viral co-receptors inside the host to minimize or otherwise reduce potential spreading inside the organism [15]. The antidote (e.g., nanomaterial or other carrier) can be inhaled, orally ingested or administered through intravenous injection and/or any other delivery method or technology (e.g., inhalation, ingestion, topical application, etc.), as desired or required.

It is another aim of the inventions in the present application to provide a medical countermeasure similar to that of chelating agents used in toxifications of metal complexes (e.g., arsenic poisoning, snake venoms, mold toxins and the like). In some embodiments, the present inventions provide a carrier (e.g., a functionalized nanomaterial) that acts as an antidote, and is advantageously capable of binding toxic metal complexes, toxins, poisons and/or the like to larger entities that can be metabolized, degraded and/or secreted/otherwise removed from the body [15]. The antidote (e.g., carrier or nanomaterial) could be inhaled, orally ingested, administered to the host using intravenous injection and/or any other delivery method or technology.

In some embodiments, a carrier (e.g., a functionalized nanoparticle) is loaded, coated and/or decorated with an API and/or RNA/DNA and/or other molecules or materials capable of binding to cell structures of the host (e.g., receptors of the host's cell structures) and delivering its cargo or contents to targeted cell population. Beneficially, this can at least partially block or otherwise limit entry of a specific pathogen, such as, for example, influenzas, rhinoviruses, noroviruses, respiratory syncytial viruses, coronaviruses and other viruses causing infection (e.g., in the respiratory tract or other anatomical location). Further the use of such carriers can advantageously provide the capability of releasing certain materials (e.g., APIs, therapeutics, other molecules, etc.) to the host thereby minimizing or at least reducing the spread of the infectious agent.

According to some embodiments, the present application discloses a carrier (e.g., a polymeric or protein/peptide functionalized nano and/or micro particle) that is loaded with one or more anti-viral molecules capable of binding to one or more receptors and/or other portions of a host cell structure (e.g., ACE2 and/or TMPRSS2 receptors, sialic acid, histo-blood group antigens, ICAM-1, IGF1R receptors, other receptors in humans that at least partially hinder (e.g., allosterically hinder) the targeted virus or other pathogen (e.g., influenza, rhinovirus, norovirus, respiratory syncytial virus, SARS-CoV-2 or another corona virus) from binding to its target receptor). As a result, the risk of infecting the host can be reduced, e.g., for a limited or prolonged duration.

Certain advantages are obtainable as a result of the present inventions, as carriers (e.g., nanoparticles, other particles or objects, etc.) can be synthetized using different materials and/or functionalized (or otherwise configured) with virtually endless combinations of features and/or functionality. In some embodiments, the carriers include mesoporous silica nanoparticles (MSNs) or other inorganic silica-based materials which have shown great potential for targeted drug delivery. For example, MSNs can have tunable ordered repetitive mesostructures of pores that can be loaded with different drugs and/or other components or materials. In some arrangements, such carriers or particles can be synthesized in various sizes, shapes and/or other configurations, as desired or required for its particular purpose or application. Furthermore, inorganic silica materials, such as MSNs, are safe, biocompatible, stable, customizable and versatile. For instance, inorganic silica materials have been given a Generally Recognized As Safe (GRAS) designation by the FDA as silica degrades in aqueous solution to silicic acid and gets excreted or otherwise removed (e.g., via the urine), and is, therefore, considered biocompatible [15]. In some embodiments, since MSNs and other inorganic silica-based materials have been proved to be a versatile delivery vehicle with beneficial features and properties (e.g., improved stability, large surface area, tunable pore sizes and volumes, capable easy encapsulation of drugs, proteins, biogenic molecules, etc.), they are well suited to be used in carriers.

In some embodiments, the carriers comprise lipid-based micelles (e.g., forming the cores of the carriers). Such carriers can be provided by synthetizing, for example, cholesterol based lipid particles decorated with SARS-CoV-2 spike protein fragments that bind both to ACE2 and TMPRSS2 as well as to cholesterol and its high-density lipoprotein (HDL) scavenger receptor B type 1 (SR-B1) and/or FcγR receptor. These co-receptors can facilitate ACE2-dependent entry of the carrier (e.g., the envisioned nanoparticle) loaded with one or more selected APIs for combating a targeted disease (e.g., COVID-19 disease). In some embodiments, advantageously, by creating a carrier (e.g., a nanoparticle and/or microparticle) that competes with the spike protein-HDL interaction, the ability of SARS-CoV-2 for ACE2-mediated internalization is lowered and viral entry to host cells is blocked and replication hindered.

In some embodiments, the carriers comprise solid lipid particles synthetized by microfluidics and/or protein-based particles such as ferritin-based particles that self-assembly decorated or conjugated with viral mimicking protrusion capable of both binding to the target receptor and stimulating the host immune system against the said virus.

In some embodiments, carriers comprise quantum nanoparticles (e.g., as a core). Such quantum particles or carriers once decorated or otherwise provided with the desired surface features (e.g., SARS-CoV-2 or other viral spike protein receptor binding domain (RBD)) can be capable of binding to ACE2 receptors, other receptors and/or other binding sites of the host cell structure. Accordingly, such carriers can be internalized (e.g., by ACE2-GFP HEK293T cells after a certain time period, for example, approximately 3 hours), thereby validating that it is possible to produce man-made virus-like particles that efficiently bind and are internalized by target cells. Furthermore, protein-lipid entities, such as Dalbavancin, an antibiotic, can bind to the ACE2 receptor (or another receptor or binding site) to prevent or reduce the likelihood that the targeted pathogen (e.g., SARS-CoV-2) is able to enter its host via intervening viral-receptor interactions.

In some arrangements, carriers (e.g., nano-sized and/or micro-sized materials) are synthesized that mimic (e.g., accurately, approximately) the targeted pathogen by using, for example, the known size, morphology, surface properties and/or other properties of the infectious agent. Thus, a man-made carrier (e.g., particle, object) can be produced that at least partially hinders or otherwise mitigates the spread of the disease caused by the target infectious agent (e.g., virus, bacterium, other pathogen) by competitive inhibition. In some embodiments, such man-made carriers (e.g., particles, materials, etc.) are configured to (i) bind to receptors or other binding sites of host cell structures, thereby blocking the attachment of pathogens to such receptors or binding sites and preventing (or lowering the likelihood of) the infectious agent from entry into the cell structure and/or (ii) bind to the infectious agent itself thus immobilizing the threat caused by the infection agent. Accordingly, the carrier embodiments disclosed herein and equivalents thereof provide two possible approaches to reducing infection of a host's cells, and as such, have immense potential in different applications in medicine, drug development, medical devices, consumer, sanitation products and/or the like.

According to some embodiments, it is possible to synthetize nano-sized and/or micro-sized materials (e.g., carriers, particles, objects) that mimic, at least partially, targeted viruses or other pathogens (e.g., SARS-CoV-2 virus, the spread of which resulted in a global epidemic starting in 2020, pandemic strain/type of the influenzas, rhinoviruses, noroviruses, respiratory syncytial viruses, coronaviruses (including mutated forms thereof) derived from SARS-CoV-2, other viruses, other pathogens, etc.) by using the known size, morphology, surface properties and/or other characteristics or properties of the targeted virus or other pathogen. Thus, carriers (e.g., man-made particles or objects) can beneficially hinder or at least slow the spread of the disease by competitive inhibition.

In some embodiments, such carriers (e.g., man-made materials) are designed and otherwise configured to bind to surface receptors, co-receptors and/or other binding sites of a host cell structure, and thereby blocking, at least partially, the entry of the virus or other pathogen. In some arrangements, in addition to binding to host cell structures (and thus at least partially blocking or preventing the attachment of a pathogen to said host cell structures) and/or immobilizing the pathogen by binding to the pathogen itself, carriers are configured to simultaneously administer or otherwise deliver APIs and/or other materials. Such APIs and/or other materials delivered to target cells and tissues can be configured to create an environment that is hostile to viral replication and that provides a synergistic approach to the host. Such carriers and the associated methods of treatment can have immense potential in different applications in medicine, drug development, medical devices, consumer products and the like. In some embodiments, for instance, adding Zinc ions, Celastrol Cannabinols, anti-viral molecules, other APIs and/or other substances or materials to the nanoparticle or other carrier, it would be possible to create an environment for at least partially arresting the viral replication cycle inside host cells (e.g., cells that are expressing ACE2 receptors or other targeted receptors on their cell surface).

In some embodiments, a carrier (e.g., a synthetic nanoparticle and/or microparticle) can be used to reduce the spread of influenzas, rhinoviruses, noroviruses, respiratory syncytial viruses (RSVs), coronaviruses (e.g., SARS-CoV-2, other derived coronaviruses), other viruses that cause symptoms such as respiratory infection, diarrhea, common cold, cytokine storm, general discomfort, serious illness, death and/or any other viruses or other pathogens. To that end, in some embodiments, the synthetic particles or other carriers can be manufactured to match, imitate, emulate or substantially match, imitate or emulate one or more characteristics or other properties of one or more targeted pathogens (such as, for example, influenzas, rhinoviruses, noroviruses, respiratory syncytial viruses (RSVs), coronaviruses (e.g., SARS-CoV-2 virus) and/or any other viruses or other pathogens). More specifically, according to some arrangements, the particle or carrier is preferably fabricated to a size of around 10 to 200 nm, for example 50 to 150 nm (such as around 100 to 120 nm), 10 to 200 nm, 10 to 100 nm, 100 to 200 nm, 50 to 200 nm, 10 to 150 nm, values between the foregoing values and ranges).

Further, in some embodiments, the carriers can be coated with similar amino acids and peptides as the targeted virus and/or other pathogen. For example, in some embodiments, the carrier can contain glycoprotein spike proteins, other protrusions, similar molecules and/or other surface features. In some embodiments, such features of the carrier can be configured to mimic or substantially mimic certain surface features of the viral envelope. More specifically, in some embodiments, the particle is preferably fabricated to a size of around 100-120 nm and coated with similar amino acids and peptides as the virus contains, for example, glycoprotein spikes, protrusions and/or other features at the viral surface or similar molecules that mimic the surface of the viral envelope. In some embodiments, the carrier (e.g., particle or object) is fabricated to a size of around 100 nm (e.g., 80 to 120 nm, 90 to 110 nm, 100 nm, values between the foregoing, etc.) and is coated with similar amino acids and peptides as the targeted virus or other pathogen (e.g., glycoprotein spikes and/or protrusions at the viral surface or similar molecules that mimic the surface of the viral envelope). In more specific embodiments, the carrier (e.g., object or particle) is fabricated to a size of around 0.2 to 100 nm and coated with similar amino acids and peptides as the virus contains e.g. protrusions at the viral surface.

Next, certain embodiments will be described in more detail.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIG. 3 is a schematic depiction of immobilization of an infectious agent by functionalized nanomaterials according to some embodiments of the present technology;

FIG. 5 schematic depiction of utilization of nanoparticles coated with peptides resembling the binding motif of the spike protein from the SARS-CoV-2 virus for encapsulating and immobilization of the co-receptor and as a consequence decrease the virus mobility, thus minimizing the risk of the virus's infecting the host cells or infecting the host to other organs;

FIG. 7 shows an example of a SARS-CoV-2 spike RBD expression construct. Different expression cassettes (shown as the XXX region) can be used for expressing the desired construct e.g. influenza H7 haemagglutinin (indicated as "Signal sequence"), Tag, spacer, and SARS-CoV-2 RBD (SEQ ID NO: 7).

DETAILED DESCRIPTION

Figure 1:
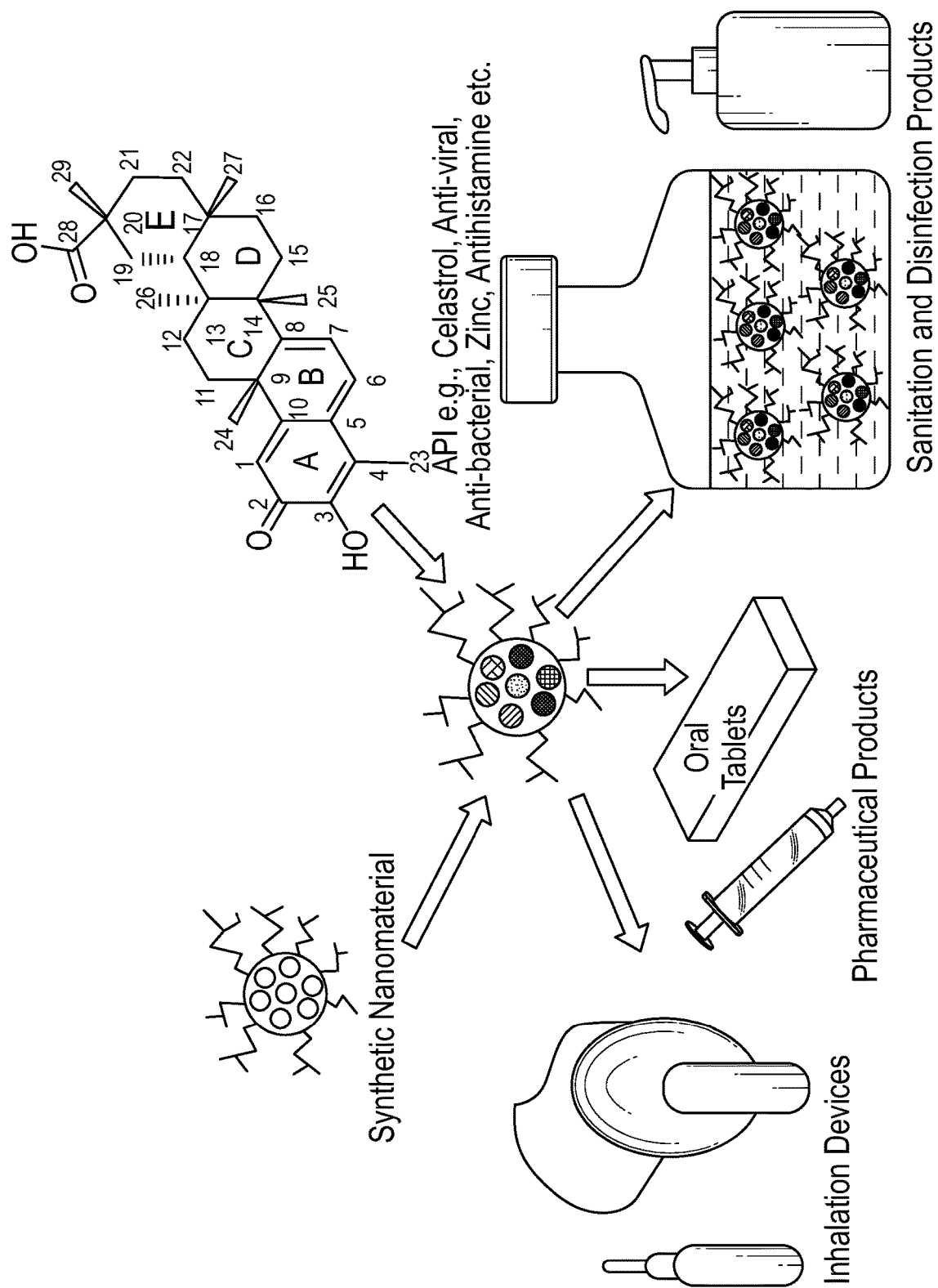
FIG. 1 is a schematic depiction of different applications of synthetized nanomaterials according to some embodiments of the present technology.

In the present context, the term "around" means, when used in connection with numerical values, that a variation of ±25%, in particular ±20%, for example ±10%, or ±5%, of the exact value is included by a literal reading of that value.

In the present context, the term "about" means, when used in connection with numerical values, that a variation of ±25%, in particular ±20%, for example ±10%, or ±5%, of the exact value is included by a literal reading of that value.

The term "polymer" is used herein in a broad sense and refers to materials, compounds, amino acids and proteins characterized by repeating moieties or units.

The term "functionalization" is used herein in a broad sense and refers to conjugating, coating, covalently and/or otherwise adding (e.g., allosterically adding) materials, compounds, drugs, amino acids and/or proteins to the synthetized particle or object.

The term "biocompatible" refers herein to "the ability of a material to perform with an appropriate host response in a specific application" (e.g., William's definition) [19].

Nanomaterials and nanomedicine can be classified according to the targeting strategies used, which can include, for instance, active or passive targeting. In some embodiments, passive targeting utilizes non-functionalized particles for accumulation in organs and tissues that are responsible for clearance of foreign objects such as macrophages, e.g., in the liver, spleen, etc. In some arrangements, tumor microenvironments typically show an enhanced permeability and retention effect (EPR), which can be a consequence of leaky and fenestrated blood vessels around tumors. Active targeting, on the other hand, uses a targeting ligand or functionalization that enhances the accumulation of the carrier at target site [15].

There are virtually endless functionalization possibilities by covalently attaching, adhering, saturating or binding (e.g., allosterically binding) molecules, polymers, proteins, amino acids, compounds and/or drugs onto the nanomaterial for achieving active targeting. One of the major advantages of functionalizing a smaller molecule to a larger entity, e.g., antibody or hydrophobic molecules to a nanomaterial, is to increase the combined objects stability and/or solubility and/or possible minimize the unwanted immunologic reaction [15].

Described herein are carriers (e.g., fabricated nanomaterials or other carriers) used for inhibiting or improving the ability to inhibit, at least partially, pathogen entry of certain pathogens or other unwanted organisms, in particular coronaviruses (e.g., SARS-CoV-2), influenzas, rhinoviruses, noroviruses, respiratory syncytial viruses and other viruses causing respiratory infection to the host organism. Accordingly, such nanomaterials or other carriers can be advantageously used to limit or reduce the replication and spread of a disease or virus.

Embodiments disclosed herein have capabilities of carrying or otherwise delivering or providing anti-pathogenic pharmaceuticals or other materials, such as anti-viral drugs, in the carrier (e.g., nanomaterial) to reduce the replication and growth of the infectious agent.

Embodiments disclosed herein pertain to the fabrication of man-made (e.g., fabricated) carriers or materials (e.g., in the nano- and/or microscale) that are configured to at least partially saturate and bind to receptors, proteins and/or macromolecules at the cellular level in order to reduce the likelihood (e.g., prevent) and reduce (e.g., minimize) pathogens (e.g., coronavirus) binding to and/or entering into receptors and/or target tissues of the host. In some embodiments, the synthesized carrier (e.g., nanomaterial) can be stored and loaded onto a medical device capable of releasing (e.g., on-demand, specific amounts) the synthesized carrier system to specific tissue. Such medical devices or other devices or systems include, without limitation, inhalation devices, oral tablets, injectable substances, lotions or creams and/or any other device, system or component, as desired or required.

In one aspect or embodiment, a synthetic carrier, particle or object is configured to at least partially hinder or impede the spread of the COVID-19 disease by competitive inhibition and to deliver an API, drug or molecule to targeted cells and/or tissues with increased or improved efficacy. In some embodiments, the use of such carriers, particles or objects is configured to have few or minimal side effects for creating a hostile environment for the virus or other targeted pathogen. According to some arrangements, the carrier or particle (e.g., the mimetic nanoparticle) is functionalized with, in one non-limiting example, hexapeptide resembling that of the RBD from SARS-CoV-2. This can, according to some embodiments, allow high binding affinity to the ACE2 receptor at the lining of the respiratory system, thus blocking, at least partially, a route (e.g., a primary route) of infection. In some embodiments, this approach virtually eliminates the problem associated with mutations of the viral strain, because the specific target is the human receptor and not the constantly evolving coronavirus. This may be especially significant, for instance, in light of the impactful SARS-CoV-2 mutations that have appeared starting in 2021 and beyond, which have and will have a significant impact on the state of world health. Alternatively or simultaneously, ACE2 receptor binding moieties or antibodies designed to bind and immobilize the virus at specific sites can be used.

Therefore, in some embodiments, as noted above and discussed in greater detail herein, carriers (e.g., particles, obstacles, etc.) are configured to prevent or reduce the likelihood of infection by pathogens using one or more principles or mechanisms. For example, in some arrangements, the carriers are sized, shaped and otherwise configured to prevent or reduce the likelihood of pathogen infection by competitive inhibition (e.g., blocking receptors).

In another aspect or embodiment, a carrier (e.g., a synthetic particle or object) is configured to deliver its "cargo" or content to targeted cell population. For example, in some arrangements, the carrier comprises a core material that can be "loaded" or otherwise provided with (e.g., into or onto) drugs, API and/or other molecules or materials. Such substances provided in and/or on the carrier can be targeted with higher efficacy to specific cells and tissues using, for example, functionalization (e.g., protrusions that are capable of binding to host cell structures such as receptors that facilitates carrier uptake at said cells enabling targeted therapeutics). Thus, potentially, the therapeutic effect of the drug can be improved, increased or otherwise enhanced, e.g., by accumulating the local dosage in specific cells, reducing at least some side-effects of the drug (e.g., by reducing off-target effect in unwanted cells and/or the like).

In another aspect or embodiment, a carrier (e.g., a synthetic particle or object) is configured to hinder, at least partially, the spread of influenza or the "flu" by competitive inhibition and/or immobilizing the virus. As noted above, in some arrangements, the size of the carrier (e.g., the particle or object) is similar or substantially similar to the size of the virus or other pathogen being targeted. For example, a diameter or other cross-sectional dimension of the carrier can be 50% to 200% (e.g., 50-200, 50-100, 50-150, 50-200, 100-150, 150-200%, values and ranges between the foregoing, etc.) of the diameter or other cross-sectional dimension of influenza or other targeted virus or pathogen.

In some embodiments, the carrier is loaded with or otherwise comprises an API, drug, molecule and/or other materials to be delivered to target cells and tissues with increased efficacy and with minimal or reduced side effects, while creating a hostile environment for the virus. However, in other arrangements, the carrier (e.g., particle or object) does not contain any API, drug or other molecule that is intended to be delivered to targeted cells and tissues. Even in such embodiments, the carriers or particles can be configured to reduce the likelihood of infection (e.g., by preventing the actual virus from binding to and infecting targeted cells of the host). This can be accomplished by immobilizing the targeted virus (e.g., using a carrier that is configured to bind to the targeted pathogen) and/or by blocking receptor (or other binding sites or portions) of host cells. The mimetic carrier or particle can be functionalized with, for example and without limitation, protein fragments resembling HA and NA binding moiety. In such embodiments, high binding affinity to the host sialic acid receptors at the lining of the respiratory system if facilitated, thereby at least partially blocking a route (e.g., the primary route) of infection. Alternatively or simultaneously, sialic acid receptor binding moieties or antibodies designed to, at least partially, bind and immobilize the virus at one or more host receptor binding moieties, receptor binding domains and/or other sites can be used.

In another aspect, a carrier (e.g., a synthetic particle or object) mimics (or is configured or adapted to mimic), for example, Rhinoviruses in order to hinder, at least partially, the spread of the major causative agent of the common cold by competitive inhibition. In some embodiments, the appropriate API, drug or molecule is delivered to target cells and tissues with increased efficacy and with minimal or reduced side effects while creating a hostile environment for the virus. The mimetic particle (e.g., carrier) can be functionalized with, for example, but not limited to, VP1 and VP2 capsid protein allowing high binding affinity to the ICAM-1 and other related receptor at the lining of the respiratory system. Thus, the primary route of infection can be, at least partially, blocked. Alternatively or simultaneously, ICAM-1 receptor binding moieties or antibodies designed to bind and immobilize the virus at host receptor binding moiety, receptor binding domain or other sites can be used.

In another aspect, a carrier (e.g., a synthetic particle or object) mimics (or is configured to mimic), at least approximately or substantially, respiratory syncytial virus (RSV) in order to hinder, at least partially, the spread of influenza or the "flu," a respiratory disease, by competitive inhibition. In some embodiments, with the use of such carriers, the appropriate (e.g., desired, required, etc.) API, drug or molecule is delivered to target cells and tissues with increased efficacy and with minimal or reduced side effects while creating a hostile environment for the virus. The envisioned carrier (e.g., mimetic particle or object) functionalized with, for example and without limitation, receptor attachment protruding glycoprotein (G) allowing high binding affinity to the IGF1R receptor at the lining of the respiratory system. Accordingly, such a carrier can be configured to block, at least partially, the primary route of infection. Alternatively or simultaneously, IGF1R receptor binding moieties or antibodies designed to bind and immobilize the virus at other sites than the host receptor binding moiety can be used.

In another aspect, a carrier (e.g., a synthetic particle or object) mimics or is configured or adapted to mimic) Noroviruses. In such embodiments, the carrier can hinder, at least partially, the spread of "stomach flu" a gastroenteritis disease by competitive inhibition. In some embodiments, with the use of such carriers, the appropriate (e.g., desired, required, etc.) API, drug or molecule is delivered to the target cells and tissues with increased efficacy and with minimal or reduced side effects while creating a hostile environment for the virus. The carrier (e.g., the envisioned mimetic particle) functionalized with, for example and without limitation, VP1 containing the P2 subdomain allowing high binding affinity to the including sialic acid and histo-blood group antigens at the lining of the respiratory system. Thus, the carriers can block, at least partially, the primary route of infection. Alternatively or simultaneously, sialic acid receptor binding moieties or antibodies designed to bind and immobilize the virus at host receptor binding moiety, receptor binding domain or other sites can be used.

FIG. 1 schematically shows some non-limiting applications of synthetized carriers (e.g., nanomaterials, objects, particles, etc.) according to some embodiments of the present technology. Thus, by way of an example, the carrier (e.g., nanomaterial) can be loaded with one or more active pharmaceutical ingredients (API), such as, e.g., Celastrol, Zinc, anti-viral compounds, Interferon-Gamma modulators, etc., and then used in inhalation devices, oral tablets or injectables, or other devices or tools of administering the carriers, to name just a few. Such nanomaterials and/or micromaterials can be used to hinder, at least partially, the entry of novel coronaviruses within host cells, thereby reducing or minimizing the spreading of the disease.

Embodiments disclosed herein allow for decreasing the risk of a pathogen or pathogens, such as coronaviruses, influenzas, rhinoviruses, other viruses causing respiratory infection (e.g., SARS-CoV-2), entering its host for a temporary or prolonged duration. Accordingly, such embodiments can advantageously give a targeted treatment for the specific disease caused by the infectious agent.

In a first embodiment, a synthetic carrier is provided, which comprises biocompatible particles having a maximum size in at least one dimension in the nanometer or micrometer range. In some embodiments, said maximum size in at least one dimension is 10 to 500 nanometers (e.g., 10 to 500, 10 to 50, 10 to 100, 50 to 100, 1 to 100, 100 to 200, 200 to 300, 300 to 400, 400 to 500, 200 to 400 nanometers, values and ranges between the foregoing, etc.). In some embodiments, such carriers form or include a core and include a functionalized surface capable of binding to target areas of cell surfaces of a host. Advantageously, such binding can at least temporarily block the target areas to prevent or minimize pathogens (e.g., influenzas, rhinoviruses, coronaviruses including but not limited to SARS-CoV-2, other viruses causing respiratory infection, thereby reducing the risk of the host contracting the disease caused by the pathogen (e.g., the COVID-19 disease, diarrhea, respiratory infections, common cold, etc.).

As used herein, the term "host" means, but is not necessarily limited to, an individual mammal, in particular a human or an animal.

Figure 2:
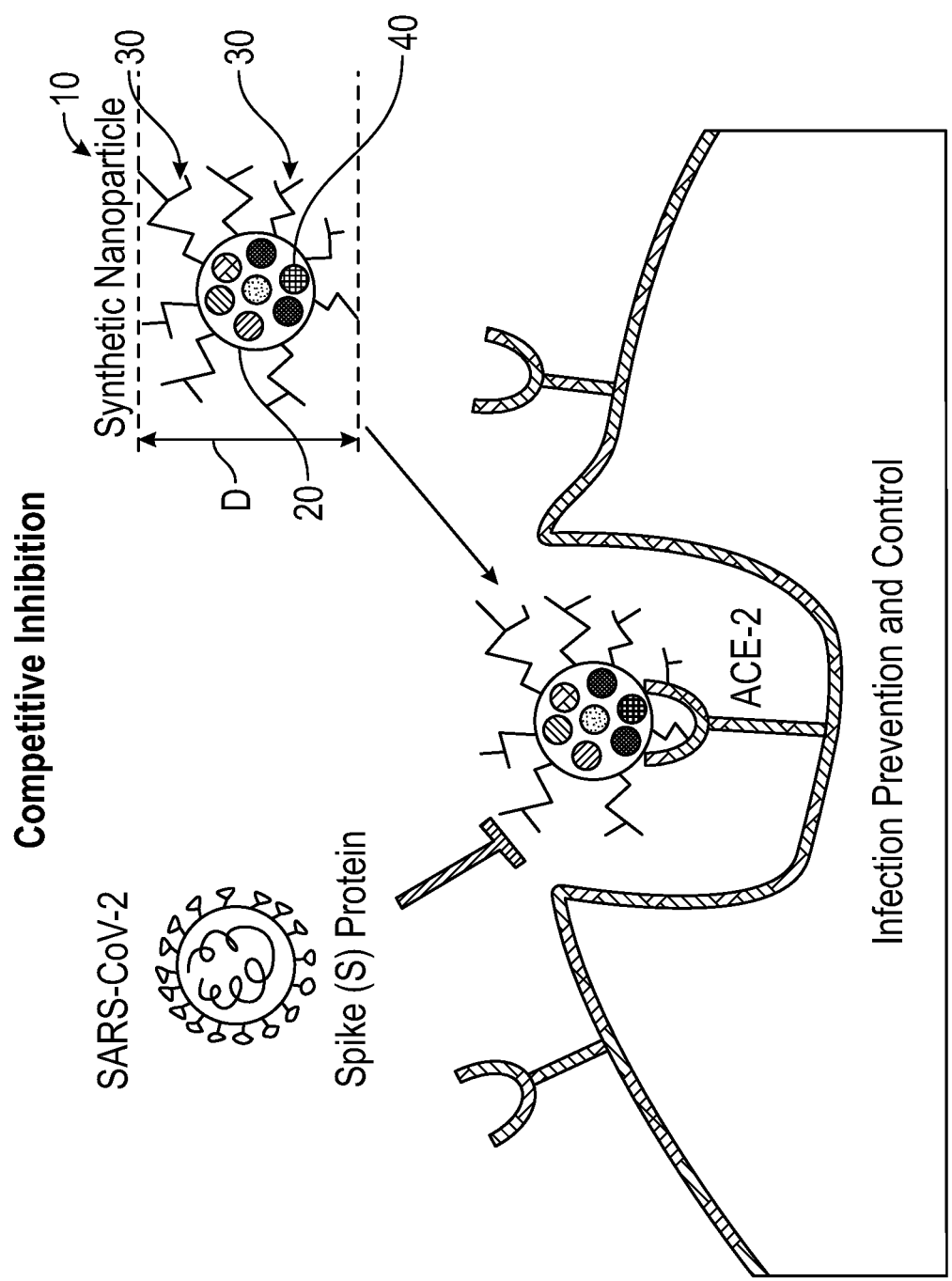
FIG. 2 is a schematic depiction of infection prevention and control by competitive inhibition using synthetic nanoparticles according to some embodiments of the present technology.

As schematically illustrated in FIG. 2, in some embodiments, the carrier 10 comprises a core 20 and a plurality of surface features 30 related to the core. As disclosed herein, the surface features can include protrusions that resemble or mimic, at least partially, spike proteins or other protrusions or features of a target virus or other pathogen. With continued reference to FIG. 2, the carrier 10 can be "loaded" or otherwise provided with one or more materials or other substances (e.g., APIs, other pharmaceuticals or agents, etc.) 40. As disclosed herein, such materials 40 can be delivered by the carrier to or near the site of a targeted virus or other pathogen for improved treatment (e.g., therapeutic treatment, infection prevention or mitigation, etc.).

In some embodiments, the synthetic carrier comprises a "nano" material which can be of nano- or micrometer or larger size. In some arrangements, the synthetic carrier has a size in at least one dimension which is in the nanometer scale. In some arrangements, the synthetic carrier has a size in at least one dimension which is in the micrometer scale. For example, such a size in at least one dimension is schematically depicted in FIG. 2 as dimension D. In other embodiments, the carrier has a size in at least one dimension that is outside the nanometer or micrometer range, as desired or required. For instance, the carrier can have a size in at least one dimension which is smaller than one nanometer (e.g., in the picometer range or smaller) or greater than one millimeter, depending on the targeted pathogen or other factors. The nanomaterial or other synthetic carrier can be formed as a particle, spheroid, cubical, cigar-shaped, elongated, triangle, sharp and pointy, a sheet and film and/or any configuration or shape.

According to some embodiments, a maximum cross-sectional dimension of the core 20 of the carrier 10 is 10% to 1000% (e.g., 10 to 1000, 500 to 1000, 10 to 500, 50 to 150, 10 to 300, 100 to 500, 10 to 100, 75 to 125%, values between the foregoing, etc.) of a maximum cross-sectional dimension of the pathogen (e.g., virus, bacterium, other pathogen, etc.).

In some embodiments, the synthetic carrier has a maximum size in at least one dimension which is smaller than 2500 µm (e.g., less than 2500 µm, less than 2000 µm, less than 1500 µm, less than 1000 µm, less than 500 µm, less than 100 µm, less than 50 µm, less than values between the foregoing, etc.). In one embodiment, the material has a maximum size in at least one dimension which is smaller than 10 µm (e.g., less than 10 µm, less than 5 µm, less than 1 µm, less than values between the foregoing, etc.). In one embodiment, the material in particular nanomaterial has a maximum size in at least one dimension which is smaller than 1000 nm, in particular smaller than around 500 nm or around 100 nm or smaller than around 10 nm or smaller than around 0.2 nm.

In one embodiment, the synthetic carrier is biocompatible. For example, according to some arrangements, such a material is configured to cause no reaction or only a minor unwanted reaction in the end-user (e.g. toxicity, off-target effects, etc.).

Generally, in some embodiments, the carriers disclosed herein are synthetic, which is used interchangeably with "synthesized" to denote that they are man-made or non-natural.

Embodiments of the carriers comprise organic or inorganic materials, protein based, ferritin protein particles, lipid droplets, micelles, solid lipids, or any combination of these.

The synthetic material can be selected from inorganic and organic, monomeric and polymeric materials capable of forming biocompatible nano- or micro-sized particles as explained herein.

Examples of materials for the carriers comprise one or more of the following: synthetic polymers (e.g., thermoplastic or thermosetting materials, such as polyolefins, polyesters, including biodegradable polyesters (e.g., polylactides, polycaprolactones, etc.), polyamides, polyimides, polynitriles, etc.). Further non-limiting examples of possible materials include, for example and without limitation, silica, polysiloxanes, silicone materials which optionally may contain organic and metal residues, and/or the like. In some embodiments, silica particles are preferred, but not in all embodiments.

According to some embodiments, the carrier comprises amino acids, proteins, salts and minerals and/or similar molecules or materials, as desired or required.

In one embodiment, the material, which forms the core structure of the carrier, is manufactured or otherwise obtained using one or more of the following: 3D printing, microfluidics, sol-gel methods (e.g., bottom-up methods or top-down methods of fabrication), genetically engineered organism producing specific proteins or amino acids that can either self-assembly such as ferritin protein particles or conjugate to larger entities any other method or technique, and/or combinations thereof.

In one embodiment, the core material comprises one or more materials, such as, for example, mesoporous silica nanoparticles with ordered mesostructures of pores. Such pores can be loaded with different drugs. The most common methods for drug loading to particles is either by physical adsorption using a highly saturated drug solution (e.g., a hydrophobic solvent such as cyclohexane with a hydrophobic drug) or an aqueous solution for water-soluble drugs. In some embodiments, loading further includes covalently conjugating the molecule to the particle surface using, for example, thiol chemistry and/or attracting the cargo molecule by having a different charge than the particle (e.g., particles having a positive charge which will allow loading of negatively charged drug, RNA/DNA molecules).

The carriers (e.g., particles or objects) disclosed herein can be synthetized in various sizes and shapes. In one embodiment, the material forming the core of the carrier contains pores with diameters between 1 and 75 nm, such as, for example, 2 to 50 nm, 2.5 to 30 nm, 2 to 5.5 nm, other values or ranges within the foregoing. In some embodiments, determining the hydrodynamic size using dynamic light scattering (DLS) makes it possible to confirm redispersibility of particle. In some arrangements, the morphology and particle diameter can be measured by either scanning electron microscope (SEM) or transmission electron microscopy (TEM). In order to determine surface area, pore size and pore volume, N2-sorption measurements can be used. The size and volume of the of the mesopores can be detected using small angle X-ray (SAXRD), according to some embodiments. The drug loading is, in some embodiments, measured by Thermogravimetric analysis (TGA) and alternatively or additionally measured by UV/vis spectroscopy measurements at a wavelength of 425 nm. Any alternative method or technology of forming the carriers and/or determining measurements can be used, either in addition to or in lieu of those disclosed herein, as desired or required.

In one embodiment, the core material comprises mesoporous silica nanoparticles (MSNs).

In one embodiment, the material compromises a nanoparticle core with coated targeting ligands with a possibility of (or configured to allow for) loading the particle with API, drugs, molecules, proteins and amino acids, RNA or DNA and compounds of interest.

In one embodiment, the material compromises a nanoparticle core and/or microparticle core with coated and/or functionalized targeting ligands with a possibility of (or configured to allow for) loading the particle into or onto with API, drugs, molecules, proteins and amino acids, RNA or DNA and compounds of interest.

Thus, in one embodiment, an nano and/or micro sized particle for example solid lipid particle (e.g., palmitate-based or stearylamine and the matrix lipid Compritol) having a net positive charge can be decorated/coated with negative molecules, such as RNA or DNA encoding for example interferon gamma for targeted delivery.

Thus, in one embodiment, the nanomaterial compromises a core particle or object functionalized with targeting moieties, drugs, amino acids, protein or any combination thereof, such as hybrid materials containing but not limited to 1,2-Dioleoyl-3-trimethylammonium propane (DOTAP), Cholesterol (Chol), Dioleoylphosphatidylethanolamine (DOPE) and/or 1,2-Distearoyl-sn-glycero-3-phosphorylethanolamine (DSPE), polyethylene glycol (PEG) (e.g. DOTAP:Chol:DOPE:PEG or DOTAP:Chol:DSPE:PEG) loaded with, for example and without limitation, RNA and/or DNA. In some embodiments, the object is preferably loaded with an active substance, drug or API.

In some embodiments of the present application and the technologies disclosed herein, two ways of synthetizing nanomaterials or other carriers are in particular employed. These include the top-down and the bottom-up approach or hybrid approach where some of the particle components are done with one approach and another component with another approach. In other embodiments, however, carriers can be synthesized or otherwise manufactured using other methods or approaches, as desired or required.

In the top-down approach, for example, the building materials have larger dimensions than the final product, which means that the materials undergo physical stresses, such as, e.g., grinding, milling etc., in order to be reduced in size. This process can lead to surface imperfections that could give rise to some variations in the final product that affect particle distribution in the host and binding kinetics.

In some embodiments, the bottom-up method starts by using smaller building blocks in solution transforming gradually to the final product, which can provide a more cost-efficient way of producing nanomaterials and/or micromaterials. Common bottom-up methods include, for example, co-precipitation, template synthesis and sol-gel method where the building blocks are often copolymers, colloids and liquid crystals and self-assembling components such as ferritin protein particles.

The carrier or particle system comprising of a core and functionalization can be characterized, in some arrangements, using Scanning electron microscopy and/or electron microscopy to confirm the size, monodispersity, morphology and non-agglomerated state of the particles. In some embodiments, to find (e.g., accurately, approximately) the amount of drug loading in the particle if the drug is fluorescent, particles can be dispersed in ethanol for complete drug elution. The concentration of drug can be determined by UV/vis spectroscopy measurements at a wavelength of 425 nm, for example with Celastrol. In some embodiments, from such measurements, the drug loading amount can be calculated or approximated. The mesoscopic ordering of the particles can be detected by powder-XRD using a Kratky compact small-angle system or similar X-ray diffraction (XRD) methods. In some embodiments, the hydrodynamic size of the particles can be determined by dynamic light scattering, and the mesoporosity by nitrogen sorption measurements. Thermogravimetric analysis can be used in order to estimate the amount of PEI, sugar motifs, FA or MTX or other organic content functionalized to the particle. In some embodiments, thermogravimetric analysis can be used to estimate the amount of organic contact or other molecule and/or drug content functionalized to the particle.

In one embodiment, inhibiting the spread of the virus SARS-CoV-2, influenza, rhinovirus, other viruses causing respiratory infection and/or any other virus includes using a carrier (e.g., a mesoporous silica nanoparticle, lipid nanoparticle, protein-based nanoparticle or any combination thereof with similar size as the virus). In some embodiments, such nanoparticles or other carriers are configured to be strategically provided or otherwise administered to a host in one or more ways (e.g., via inhalation, oral ingestion, intravenous injection, topical application, etc.), as desired or required. In some arrangements, the carriers (e.g., nanoparticles) include a size of 1 to 200 nm (e.g., 1 to 200, 10 to 120, 50 to 100, 90 to 110, 100 nm, values between the foregoing ranges, etc.). In some embodiments, the carriers include a size of 0.01 to 1000 nm (e.g., 0.01 to 1000, 10 to 1000, 50 to 1000, 100 to 1000, 1 to 500, 500 to 1000, 200 to 800, 400 to 600 nm, values between the foregoing ranges, etc.). In some embodiments, the carriers include a size of 0.2 to 100 nm (e.g., 0.2 to 100, 1 to 10, 2 to 20, 5 to 50, 10 to 100 nm, values between the foregoing ranges, etc.). Further, the nanoparticles can be fabricated using the bottom-up sol-gel method or top-down method.

In some embodiments, by using known viral genetic information, such as known viral (e.g., coronaviral, influenza viral, rhinoviral and/or other viral, etc.) genetic information, it is possible to produce similar peptides present in targeted viruses. For example, peptides or other structures can be similar or substantially similar to those found in viral glycoprotein spikes and/or protein protrusions, thus, in some arrangements, mimicking (e.g., at least substantially or approximately) at least some of the viral surface properties that assist with the binding of the carrier to certain receptors (e.g., ACE2 N-terminal helix or sialic acid, histo-blood group antigens, ICAM-1, IGF1R, other target receptors ACE2, etc.). In some arrangements, the carrier can include amino acid sequences found in the viral receptor binding domain (RBD) or the viral receptor binding motif (RBM) in the S protein, HA or NA or VP other decorated proteins that could be used or functionalizing the particle with similar (e.g., substantially similar) or identical peptides. Alternatively or additionally, the carrier's ability to at least partially inhibit entry of viruses can be enhanced by including organic polymers as part of the protrusion (e.g., of cationic polyamidoamine dendrimer (PAMAM)) or by predicting an amino acid sequence or polymer for producing a surface coating which is similar in surface charge as the viral surface or by attaching targeting motifs which are known to bind to the target receptor allowing selective internalization in target cells [6-9,20].

In one embodiment, the carriers disclosed in the present application or variations thereof comprise mesoporous silica particles. In some embodiments, such carriers preferably include a spherical or substantially spherical form or shape. In some arrangements, the particles or other carriers are provided with a plurality of protruding (e.g., relative to a spherical or substantially spherical core) peptide structures in the form of protein spikes or protein fragments/protrusions on their surfaces. In some embodiments, each of the particles include 5 to 500 protruding peptide structures (e.g., 5 to 500, 0 to 100, 100 to 200, 200 to 300, 300 to 400, 400 to 500, 100 to 500, 200 to 500, 300 to 500, 0 to 200, 0 to 300, 0 to 400, 0 to 500, values between the foregoing ranges and values, etc.). In some embodiments, each of the particles include 1 to 1000 protruding peptide structures (e.g., 1 to 1000, 0 to 100, 100 to 200, 200 to 300, 300 to 400, 400 to 500, 100 to 500, 200 to 500, 300 to 500, 100 to 600, 200 to 600, 300 to 600, 400 to 600, 500 to 600, 100 to 700, 200 to 700, 300 to 700, 400 to 700, 500 to 700, 600 to 700, 100 to 800, 200 to 800, 300 to 800, 400 to 800, 500 to 800, 600 to 800, 700 to 800, 100 to 900, 200 to 900, 300 to 900, 400 to 900, 500 to 900, 600 to 900, 700 to 900, 800 to 900, 100 to 1000, 200 to 1000, 300 to 1000, 400 to 1000, 500 to 1000, 600 to 1000, 700 to 1000, 800 to 1000, 900 to 1000, 0 to 200, 0 to 300, 0 to 400, 0 to 500, 0 to 600, 0 to 700, 0 to 800, 0 to 900, 0 to 1000, values between the foregoing ranges and values, etc.).

In one embodiment, the surface features or other members that protrude from a core of the carrier (e.g., spikes) have a length of about 1 to 200 nm (e.g., 1 to 200, 1 to 100, 2 to 80, 5 to 50, 20 to 100, 50 to 100, 100 to 200 nm, values between the foregoing, etc.). In some embodiments, the surface features or other members that protrude from a core of the carrier (e.g., spikes) have a length of 0.2 to 100 nm (e.g., 0.2 to 100, 1 to 10, 2 to 20, 5 to 50, 10 to 100 nm, values between the foregoing ranges, etc.). In some embodiments, the length includes the actual length of a spike or other protrusion is the total liner length of such a spike or protrusion. However, in other embodiments, the length includes the distance from the spherical or other core of the carrier to the outermost radial distance of the protrusion.

In some embodiments, allowing the carrier (e.g., synthetic particle) to compete with viral particles, such as coronaviruses (e.g., the SARS-CoV-2 virus, variants thereof, etc.), influenzas, rhinoviruses, Respiratory Syncytial Viruses (RSVs), noroviruses, other viruses, etc.) for the same receptor and/or other binding site or portion of a host cell (e.g., ACE2, sialic acid, histo-blood group antigens, ICAM-1, IGF1R receptor, etc.) can function as a hindrance and/or other obstacle (e.g., allosteric regulation or hinder, other competitive or non-competitive inhibition, etc.) for the viral particle to bind to the receptor or other site or portion. This can advantageously minimize or reduce the likelihood of endocytosis of the virus or other pathogen, thereby lowering the risk of infecting the host cell.

One embodiment of the principle of competitive inhibition is schematically illustrated in FIG. 2. As shown, by way of an example, in some embodiments, a host receptor (e.g., ACE2) is responsible for mediating the SARS-CoV-2 infection responsible for coronavirus disease 19 (e.g., COVID-19). In some configurations, by binding carriers (e.g., the novel synthetic nanoparticles, other particles, objects, etc.) to that reception site (e.g., receptor), to the specific host receptors motifs and/or other any other site or portions of the host cell, infection (e.g., caused by the SARS-CoV-2 viruses, other viruses, etc.) can be advantageously prevented, controlled and/or otherwise mitigated.

With continued reference to FIG. 2, by way of an example, a host receptor (e.g., ACE2) responsible for mediating the infection resulting in a specific disease is generally depicted (schematically). In some embodiments, by binding a carrier (e.g., a novel synthetic particle, object, etc.) to that specific area or to the specific host receptors motifs, the infection caused by the specific virus, viruses and/or other pathogen can be prevented and controlled (e.g., the likelihood of infection can be reduced or otherwise mitigated, etc.). The competitive inhibition can be utilized against different viruses and/or other pathogens (such as, for example and without limitation, influenzas, rhinoviruses, RSVs, noroviruses, other respiratory and gastrointestinal viruses, other viruses or pathogens, etc.).

Based on, for example, the foregoing, in an embodiment, carriers (e.g., synthetic nanoparticles, other particles, etc.) are selected such that they resemble, at least partially, coronaviruses (e.g., SARS-CoV-2), influenzas, rhinoviruses, noroviruses, other common cold viruses and/or any other viruses or pathogens, as desired or required. In some embodiments, preferably, synthetic nanoparticles are enhanced or otherwise optimized, at least partially, for competitive inhibition. For example, the particle morphology, size, surface properties and/or any other properties or features of such particles can be modified to achieve higher (or otherwise improve) affinity for the target receptor angiotensin converting enzyme 2 (ACE2) and/or TMPRSS2, sialic acid, histo-blood group antigens, ICAM-1, IGF1R or other target receptors. Thus, the binding affinity for the specific receptor can be advantageously increased, thereby blocking the internalization of the viral envelope more efficiently and potentially prolonging the gained viral protection [8-10].

A carrier system as described herein, wherein the carrier (e.g., synthetic nanoparticle, other particle or object, etc.) resembling a targeted virus (e.g., the SARS-CoV-2, other corona or spiked viruses, influenza, rhinoviruses, noroviruses, other common cold viruses, etc.) can be enhanced or optimized for personalized medicine as variations and mutations in individuals might give rise to slightly different target receptors. Thus, the surface properties and functionalization of the carrier can be changed to match or substantially match the individual properties (e.g., mutations or variations) in target receptors and/or other binding sites or locations of a host cell for tailored therapies.

Figure 4:
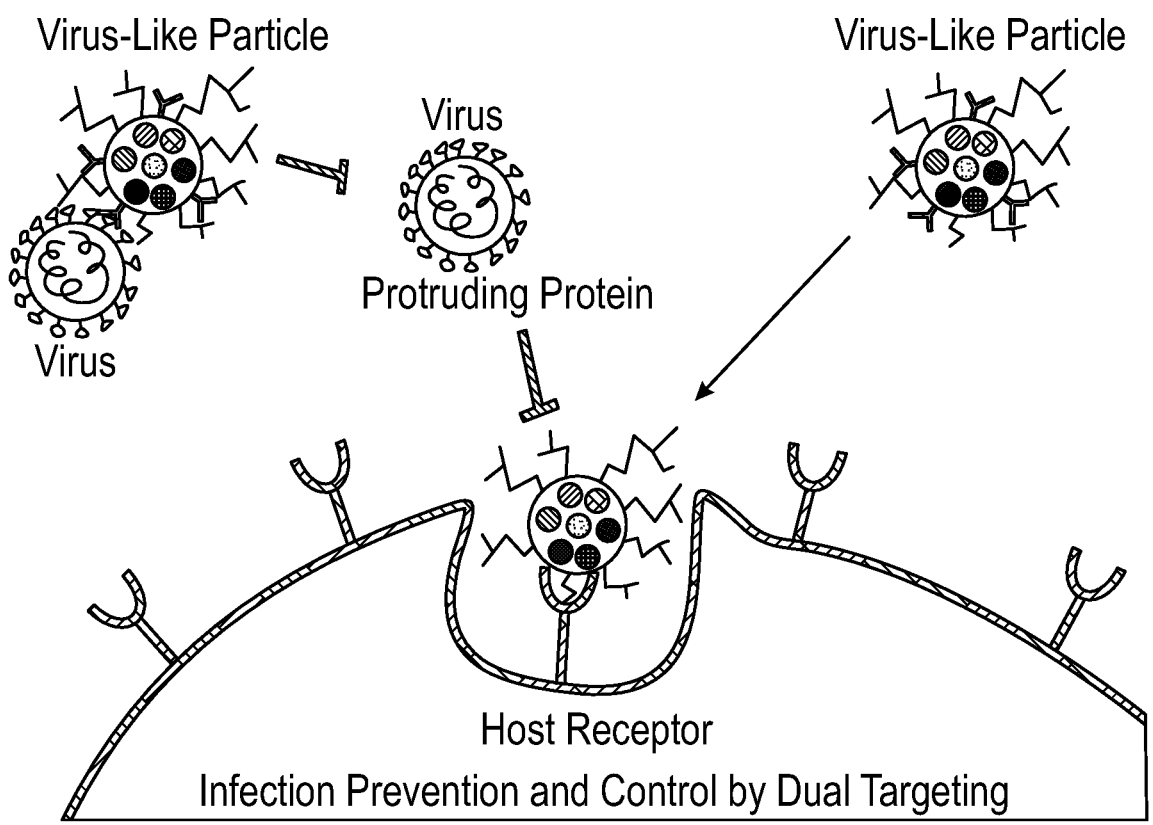
FIG. 4 is a schematic depiction of dual targeting strategy compromising both immobilization of an infectious agent and by infection prevention and control by competitive inhibition functionalized nanomaterials according to some embodiments of the present technology.
Figure 6:
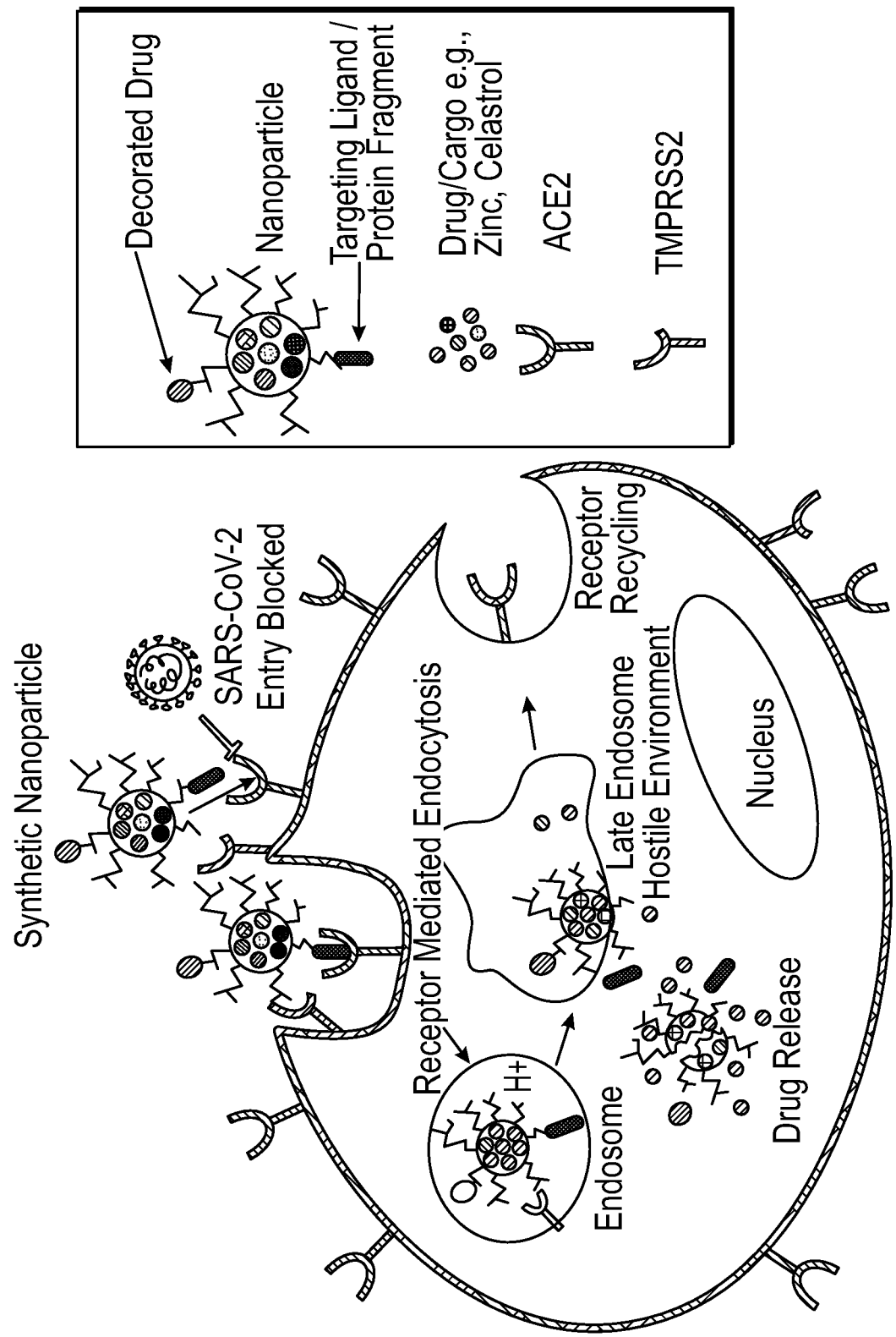
FIG. 6 is a schematic depiction of functionalized nanoparticles mimicking SARS-CoV-2 to be used as targeted intervention and therapy against COVID-19 and other respiratory diseases according to some embodiments of the present technology.

One embodiment of a targeted and/or personalized medicine is schematically illustrated in FIG. 4. As depicted, by way of an example, by designing a carrier (e.g., synthetic nanoparticle, other particle or object, etc.) that has features that resemble the selected or targeted virus or other pathogen (e.g., SARS-CoV-2, other corona or spiked viruses, influenzas, rhinoviruses, noroviruses, other common cold viruses, etc.). For example, the synthetic particles or other carriers can include spike protein fragments, protein protrusions, other protrusions, other surface features and/or any other feature or property. Accordingly, it is possible for targeted drug delivery at (e.g., at, to, near, etc.) host cells that are susceptible for the virus and/or other pathogen. In some embodiments, as discussed herein, the carrier can include (e.g., can be "loaded" or otherwise provided with) one or more drugs and/or other compounds, substances and/or materials (for example, anti-viral compounds, zinc, immune modulating drugs (e.g., Celastrol, other interferon-gamma or stimulating molecules, penicillium, Dalbavancin or other anti-bacterial compounds, drugs intended to combat virus-related pneumonia, voriconazole, isavuconazole, drugs intended to combat viral-associated pulmonary aspergillosis, anti-fungal compounds, etc.) and/or the like, as desired or required by a particular application or use.

In some embodiments, the synthetic particle or other carrier comprises (e.g., is provided with) a coating and/or functionalization that has higher affinity towards the receptor favoring the binding of the synthetic particle or other carrier than the viral one (e.g., the virus, other pathogenic or infectious agent or member, etc.).

In one embodiment, for example, the synthetic particle or other carrier comprises an amino acid sequence that is similar to that of the said viral protrusion having affinity for the same target receptor as the pathogen thus having competition for the same receptor.

In one embodiment, for example, the synthetic particle or other carrier is further optimized for improved binding to said host receptor in order to achieve improved blocking effect by competitive inhibition to the said pathogen.

In one embodiment, for example, the synthetic particle or other carrier having coating and/or functionalization of epitopes similar to that of the pathogen of interest in order to give a vaccination at target cell population.

In one embodiment, for example, silica (e.g., stable organic silica) is used as the core material that could exhibit a blocking effect that, optionally after modification of the particle, could be prolonged for hours, days or longer as it takes time for silica nanoparticles to degrade in aqueous conditions similar to the environment of the human body.

In one embodiment, for example, solid lipid particles (e.g., fabricated by a bottom-up method using microfluidics) are used as the core material for the carrier to be further coated, functionalized and/or loaded into or onto with API, epitopes, proteins, RNA/DNA, anti-virals and immune stimulating compounds such as Celastrol, interferon gamma.

In one embodiment, for example, self-assembling protein particles produced by genetically-engineered bacterial or mammalian cells producing proteins or protein fragments, such as ferritin heavy or light chain, are used as the core material for the carrier. Such particles can be further functionalized and/or loaded into or onto with other molecules, epitopes, API, epitopes, proteins, RNA/DNA, anti-virals and immune stimulating compounds such as Celastrol, interferon gamma.

According to some embodiments, the administration route of a carrier depends on the tissue that the virus has invaded. For example, if the virus or other targeted pathogen resides in the upper or lower respiratory tract, it may be preferred to use an inhalation device for administering the carriers (e.g., synthetic particles) with a desired dosage. In some arrangements, such an inhalation device can allow a desired (e.g., optimal, effective, etc.) dosage of a carrier to be provided to a targeted anatomical location on demand.

In one embodiment, there is provided an inhalation device which compromises a container (e.g., a small plastic container) with dried carriers (e.g., synthetic particles, objects, etc.) like that of a dry powder inhaler or as a meter dose inhaler where the carriers (e.g., particles) are sprayed from the inhaler as an aerosol, as an vaporizer creating a fine mist of particles and solution, as an nasal spray dispersed in an aqueous solution and/or in any other form or configuration or hybrid form, as desired or required.

In some embodiments, for improving or enhancing (e.g., maximizing) the coverage of the upper respiratory tract, an inhalation mask is used. As a result, the entry of carriers (e.g., particles) into the nasal cavity and lower respiratory tract (where epithelial cells expressing ACE2, sialic acid, histo-blood group antigens, ICAM-1, IGF1R or other receptors that may also reside) can be enhanced or otherwise improved, thereby lowering (e.g., minimizing) the risk of being infected by the virus or other pathogen, at least temporarily.

In embodiments where the viral infection is (or would be) in the gastrointestinal tract, a tablet, an orally ingestible liquid and/or any other ingestible material is the preferred route of administration of the carrier to the host or subject. The synthetic particles or other carriers of such orally administered compositions can advantageously temporarily protect, at least partially, the end-user from infection by the virus (e.g., orally, via fecal-oral transmission, etc.).

The carrier (e.g., nanomaterial, other particle or object, etc.) can also be fabricated and configured to have a high or a favorable affinity for the pathogen, thus, at least partially, encapsulating and immobilizing the threat of infection e.g. coating or functionalizing the particle with molecules that has high binding affinity towards the pathogen. Accordingly, such carriers could be used in disinfecting products (e.g., cleaning solution, hand sanitizer products, disinfecting wipes, etc.).

FIG. 3 shows, schematically and by way of an example, utilization of carriers (e.g., nanoparticles, other particles or objects, etc.) coated and/or otherwise provided with peptides resembling the binding motif of the target receptor, such as, e.g. ACE-2, sialic acid, histo-blood group antigens, ICAM-1, IGF1R or other receptors that the specific or targeted virus or other pathogen uses. For example, such targeted viruses or other pathogens include, without limitation or restrictions, coronaviruses (e.g., SARS-CoV-2), influenzas, rhinoviruses, noroviruses and other common cold viruses and/or the like. In some embodiments, as discussed throughout this application, the carriers are configured to encapsulate and/or immobilize the virus and/or other pathogen, thus minimizing or otherwise reducing the risk of the virus and/or other pathogen infecting the host.

The carrier (e.g., nanomaterial, other particle or object, etc.) can also be fabricated to have high or favorable affinity both for the pathogen. Thus, the carrier can be configured to encapsulate and immobilize the targeted virus or other pathogen. Further, as noted herein, the synthetic particle or other carrier can be provided with a coating or similar layering or component that has higher or otherwise favorable or improved affinity towards the receptor favoring the binding of the carrier (e.g., synthetic particle) relative to the affinity of the virus or other pathogen, thereby, allowing the carrier to be used in a dual targeting approach (e.g., further reducing (e.g., minimizing) the risk of contracting said disease (e.g., viral or pathogenic infection and the diseases originating therefrom).

FIG. 4 schematically shows, by way of an example only, utilization of nanoparticles or other carriers coated (or otherwise provided) with peptides resembling the binding motif of a viral protrusion protein, such as, for example, the spike protein from the SARS-CoV-2 or other coronaviruses, Hemagglutinin (HA) and Neuraminidase (NA) proteins from influenza A virus, etc. combined with peptides resembling the binding motif of host receptors (e.g., ACE2, sialic acid, histo-blood group antigens, ICAM-1, IGF1R or other receptors) of the subject. As a result, the carriers can advantageously be provided with dual targeting strategies, thereby minimizing or reducing the risk of viruses or other pathogens infecting the host.

According to some embodiments, the carrier (e.g., nanomaterial, particle or object, etc.) can be fabricated or otherwise configured to have high or favorable affinity for the targeted pathogen(s) (e.g., virus(es)) circulating co-receptors e.g. high-density lipoprotein (HDL) scavenger receptor B type 1 (SR-B1), thus immobilizing the treat which could be used as an antidote preventing further spreading of the virus in the said host.

FIG. 5 schematically shows, by way of an example only, utilization of nanoparticles or other carriers coated (and/or otherwise provided) with peptides resembling the binding motif of the spike protein from a coronavirus (e.g., the SARS-CoV-2 virus) for at least partially encapsulating and immobilizing the co-receptor. As a consequence, the mobility of the virus can be advantageously decreased, thus minimizing or otherwise reducing the risk of the targeted virus or other pathogen infecting the host or spreading the viral infection inside the said host to other organs.

Based on, for example, the above, the following represents non-limiting embodiments of the present technology:

A carrier (e.g., synthetized carrier in the nano- or microscale or any other object that has the capacity of saturating and binding to target receptors, proteins and/or macromolecules for example but not limited to ACE2, sialic acid, histo-blood group antigens, ICAM-1, IGF1R or other receptors at the surface of cells that prevents and minimize pathogen, such as influenzas, rhinoviruses, RSVs, noroviruses, coronaviruses (e.g., SARS-CoV-2), other viruses causing respiratory infection, binding and entry to the host lowering the risk of contracting the specific disease, such as COVID-19 disease, diarrhea, common cold, cytokine storm, death or generally discomfort or a combination thereof.

A carrier (e.g., a synthetized carrier in the nano- or microscale or any other object that has the capacity of binding and encapsulating the pathogen of interest, thus immobilizing, at least partially, the pathogens ability to bind and entry to the host, thereby lowering the risk of contracting the specific infectious agent).

A carrier (e.g., a carrier as above), wherein the core structure of the carrier is obtained (e.g., manufactured, fabricated, etc.), at least in part, by 3D printing, microfluidics, supercritical solution method, sol-gel method, other bottom-up and/or top-down method of fabrication self-assembling components and/or any other method or technology.

A carrier (e.g., as provided above and/or herein), where the core material is made of or comprises, however not limited to, organic or inorganic components, lipid droplets, micelles, cholesterol, amino acids, proteins, salts and minerals or other molecules.

One embodiment comprises lipid-based micelles made by, for example, cholesterol decorated with SARS-CoV-2 spike protein fragments and/or other protrusions that bind both to host receptor sites or other portions of the host cell (e.g., ACE2, TMPRSS2, etc.) and to cholesterol and its high-density lipoprotein (HDL) scavenger receptor B type 1 (SR-B1) that would facilitate ACE2-dependent entry of the nanoparticle and/or microparticle loaded with selected API for combating COVID-19 disease or other disease resulting from infection by a virus or other pathogen. In some embodiments, the cholesterol recognition amino acid consensus (CRAC) motifs near the inverted cholesterol recognition motif (CARC) have been proven to bind with SARS-CoV-2 S1 subunit and this HDL complex enhances viral entry to host cells facilitating replication [17]. Therefore, by creating a carrier (e.g., nanoparticle, other particle or object, etc.) that would compete with this spike protein-HDL interaction would potentially lower the ability of SARS-CoV-2 (or the targeted pathogen for ACE2-mediated (or other receptor-mediated) internalization, at least partially blocking viral entry to host cells and at least partially hindering replication. In one arrangements, this co-receptor incarceration could be blocked by decorating the nanoparticle with spike protein fragments from CARC-CRAC region of SARS-CoV-2 preferably but not limited to 129KKKKVCEFQFCNDPFLGVYYHKNNKKKK150 (SEQ ID No: 4) together with other amino acids for example the RBD spike fragment hexapeptide 438YKYRYL443 (SEQ ID No: 1) that binds to the ACE2 receptor creating a nanoparticle capable of blocking viral-host interaction on multiple positions loaded with selected API for targeted therapeutics (e.g., Celastrol, Zinc, ITX 5601, etc.). [8,15-18].

One embodiment comprises the use of simultaneous inhibiting and immobilizing by dual targeting approaches, where the carrier (e.g., mimetic particle) has protrusions on the outer surface that are similar to those of the virus, for example, spike protein, HA and NA or VP that would bind to the specific host receptor for inhibiting viral entry by competitive inhibition. In some embodiments, the carrier (e.g., virus-like particle) also includes surface protrusions that mimic the host component (e.g., ACE2, silicid sialic acid, histo-blood group antigens, ICAM-1, IGF1R receptors, and/or antibodies such as the monoclonal antibody bebtelovimab, etc.).

Another embodiment comprises using self-assembling recombinant protein-based nanoparticle constructs, such as, for example, SpyTag/SpyCatcher system and ferritin-based constructs [23]. Where the constructs are expressed in *E. coli*; the proteins are purified and then assembled like a two-component "superglue" into virus-like particles (VLPs) conjugated with the selected antigens, viral epitopes or fragments [24]. The carrier could be assembled using the SpyTag/SpyCatcher system or ferrtin (heavy or light chain) based particle core and then conjugated, coated and/or functionalized with the selected SARS-CoV-2 spike protein or selected hexapeptide 438YKYRYL443 derived thereof or peptides from the CARC-CRAC region or other proteins of interest. Several studies show that it is possible to construct such a VLP using SARS-CoV-2 spike protein (RBD) candidate combined with SpyCatcher technology and ferritin based particle systems [24, 25]. The selected studies using RBD-SpyVLP demonstrate that the construct is easily producible and scalable, and that the final product is thermally stable even at room temperature for several weeks [25]. The SARS-CoV-2 RBD conjugated to SpyCatcher-mi3 nanoparticle (abbreviated: RBD-mi3 NP) shows higher binding affinity for the ACE2 receptor than viral RBD monomers detected using Biolayer interferometry (BLI) kinetic assays [24]. Therefore, it appears possible to develop mimetic nanoparticles or other carriers for preventing the spreading and lowering the infection rate of novel coronaviruses with higher affinity then the RBD monomer.

The synthetic carrier or nanoparticle may comprise or be decorated with a polypeptide or protein having an amino acid sequence of the ACE2 binding sequence and/or the SARS-CoV-2 spike protein RBD or a fragment thereof. In an embodiment, the amino acid sequence of the ACE2 binding sequence and/or the SARS-CoV-2 spike protein RBD or a fragment thereof is optimized, for example such that it has a higher binding affinity for the ACE2 receptor and enhanced blocking properties that of the spike protein of the coronavirus interaction compared to the corresponding, unmodified spike protein sequence (SEQ ID No: 5). By optimizing the amino acid sequence of the ACE2 binding sequence and/or the SARS-CoV-2 spike protein RBD or a fragment thereof it is possible achieve even higher binding affinity for example with combining hexapeptides 438YKYRYL443 (SEQ ID No: 1) or 438YKYNYL443 (SEQ ID No: 3) with the optimized spike protein sequence.

In a carrier as above, according to some embodiments, the core or core material may be made of, for example, self-assembling virus-like protein nanoparticles that can be saturated with different drugs. These particles can be synthesized in various sizes and shapes.

A carrier as above, where the core material is made of, for example, mesoporous silica nanoparticles with ordered mesostructures of pores that can be loaded with different drugs and that these particles can be synthetized in various sizes and shapes.

A carrier as above, wherein the core material is functionalized with one or several of the following: peptides or proteins such as antibodies, chemical agents, active pharmaceutical ingredients (API), organic or inorganic polymers or molecules.

A functionalized carrier as above, wherein the carrier with its functionalization provides a method of specifically bind to receptors, proteins and macromolecules at the cellular level in order to prevent and minimize pathogen entry to the host target tissues by competitive inhibition.

A functionalized carrier as above, wherein the carrier with its functionalization provides a method of specifically bind to receptors, proteins and macromolecules at the cellular level in order to prevent and minimize SARS-CoV-2, influenzas, rhinoviruses, respiratory syncytial virus, norovirus and other viruses causing respiratory infection entry to the host target receptors by competitive inhibition.

A carrier system as above, wherein the carrier with its functionalization provides a method of loading drugs, API, molecules, peptides inside or onto the carrier system.

A carrier system as above, where the functionalized and drug loaded carrier system can be used for targeted drug delivery of anti-pathogenic, anti-viral or anti-microbial compounds in order to decrease the growth of the infectious agent.

A carrier system as above, where the functionalized and drug loaded carrier system can be used for targeted drug delivery of, anti-viral compounds in order to decrease the replication rate of the coronavirus.

A carrier system as above, wherein the synthetic nanoparticle resembling the SARS-CoV-2 virus is loaded into or onto the nanoparticle for further enchanting the anti-viral properties of the invention. For example, Zinc which has been shown to reduce viral replication in its host cells, can be employed [21]. Also, viscosity modulators, antihistamines, Celastrol and/or immunosuppressors can be used in the COVID-19 disease for minimizing the cytokine storm that potentially is dangerous to some patients [18,21,22].

A carrier system as above, wherein the synthetic nanoparticle resembling the SARS-CoV-2, influenzas, rhinoviruses and other viruses causing respiratory infection is loaded with proteome inhibitors or new molecular entities developed in the future for efficiently deliver the compounds in the target tissues with minimal off-target effects.

A carrier system as above, wherein the synthetic nanoparticle is decorated with molecules that has high affinity towards the SARS-CoV-2 virus or influenzas, rhinoviruses and viruses causing respiratory infection e.g. proteins resembling that of the ACE-2, sialic acid, histo-blood group antigens, ICAM-1, IGF1R receptor or any other pathogen of interest in order to bind and immobilize the infectious agent preventing or minimizing the potential risk of host entry.

A carrier system as above, wherein the synthetic nanoparticle resembling the SARS-CoV-2 virus, or any other pathogen for example influenzas, rhinoviruses and viruses causing respiratory infection is decorated with epitopes to be used as a vaccination at target cell populations.

A carrier system as above, wherein the carrier system is loaded, stored or dispersed in a device or vessel capable of on-demand release of the carrier to the end-user.

A carrier system as above, wherein the carrier system is loaded inside a dispenser such as an inhalation device, tablet, injectable substance, cream or ointment.

A carrier system as above, wherein the man-made materials are used to immobilize specific pathogens by adding the synthetic material in sanitation products and disinfectants.

A carrier system as above for minimizing the spread of diverse pathogens by binding to the target molecule in the hos body or binding to the infectious agent itself and potently inhibit the spread of the disease. Furthermore, as a combination treatment listen in the preceding embodiments hindering the replication of the infectious agent together with giving the immune system in the host a gained advantage to fight the disease similar to vaccines or immunoregulating drugs.

Figure 7:
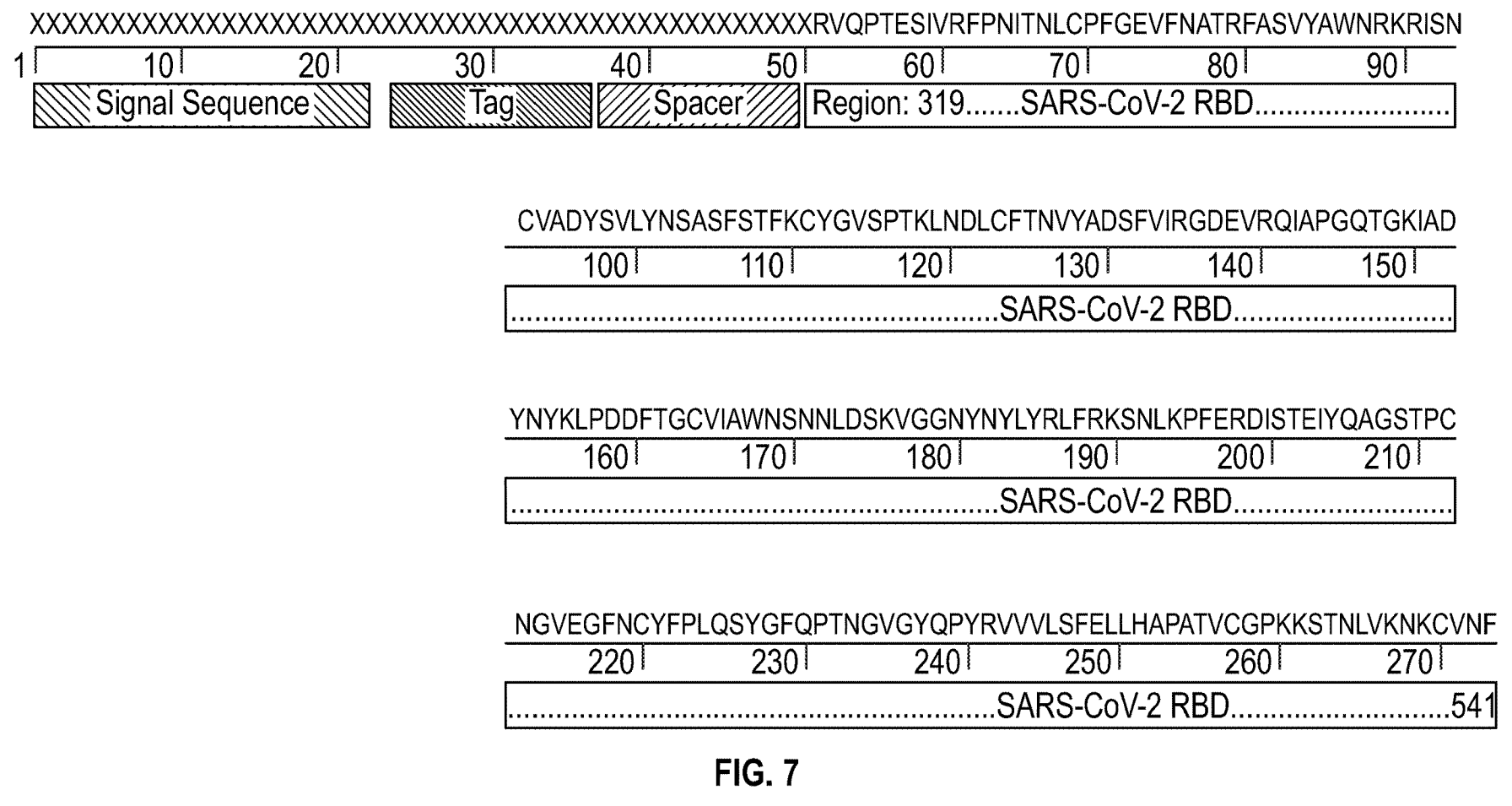

In further embodiments, the present invention is thus directed to a method for preparing a synthetic nanomaterial comprising a core object, particle, sheet, film or spheroid, tringle, star shaped, said object also compromising a coating or functionalization of organic polymers, amino acids proteins or molecules mimicking the surface of the pathogen, such as the coronavirus of interest, i.e. SARS-CoV-2 and future variants alternatively influenzas, rhinoviruses and other viruses causing respiratory infection. FIG. 7 exemplifies how the SARS-CoV-2 spike protein, and variation thereof, may be produced using a vector for producing the specific protein construct to be conjugated to the virus-like nanoparticle or synthetic carrier.

Producing a man-made material that has the capability of mimicking the pathogen of interest that has the capability of competing with the pathogen of interest for the same host target molecule, receptor, amino acid or nucleotide. Alternatively, producing a material that has the capability of binding and immobilizing the pathogen of interest minimizing the possible infection in its host.

Producing a man-made material that has the capability of mimicking the coronavirus of interest i.e., SARS-CoV-2 or influenzas, rhinoviruses and other viruses causing respiratory infection that has the capability of competing with the virus for the same host target molecule, receptor, amino acid or nucleotide e.g., ACE2 and/or TMPRSS2, sialic acid, histo-blood group antigens, ICAM-1, IGF1R receptors.

One embodiment comprises the steps of:

a) providing a core material, e.g. a nano- and/or micromaterial including nanoparticles, microparticles or any other object as disclosed herein;

b) coating or functionalizing the core material with molecules, polymers, amino acids, proteins, API, drugs or other material as disclosed herein;

c) loading the object with compounds, molecules, drugs, API, DNA or RNA etc.;

d) coating a second protective or functional layer on top of the object in particular for increasing its resistance that could be important in extreme environments such as the acidic environment in the stomach; and e) providing a small device, medical device, inhalation device or aerosol, sanitation product or consumer product that on-demand will release the containing synthetic material, particle or object for administration.

FIG. 7 shows an example of a SARS-CoV-2 spike RBD (receptor-binding domain) expression construct. Different expression cassettes (shown as the XXX region) can be used for expressing the desired construct e.g. influenza H7 haemagglutinin (indicated as "Signal sequence"), Tag, spacer, and SARS-CoV-2 RBD (using amino acid region 319 to 541, depicted in SEQ ID No: 5; PUBMED 32015508 [26]; the full amino acid sequence of the surface glycoprotein of SARS-CoV-2 is shown in in SEQ ID No: 6). The spike protein construct can be further optimized for ACE2 receptor interaction using other known amino acid sequences from SARS-CoV-2 variants such as but not limited to Alpha (B.1.1.7), Beta (B.1.351), Gamma (P.1), Delta (B.1.617.2), Omicron (B.1.1.529) and/or predicted amino acids or amino acid substitutions e.g. V367F [27], W436R, and/or N354D/D364Y.

FIG. 7 exemplifies how a spike protein, and variation thereof, or other viral protein, may be produced using a vector for producing the specific protein construct to be conjugated to the virus-like nanoparticle or synthetic man-made carrier. In an embodiment, the synthetic carrier or synthetic nanoparticle comprises and/or is coated with a peptide, a polypeptide or a protein having an amino acid sequence comprising (or consisting of) a sequence as set forth in any one of SEQ ID No:s 1, 2, 3, 4, 5 and/or 6. In a further embodiment, the synthetic carrier or synthetic nanoparticle comprises and/or is coated with a polypeptide or a protein having an amino acid sequence comprising (or consisting of) a sequence as set forth in SEQ ID No. 5 and/or 6, wherein the sequence optionally comprises one or more amino acid substitutions. The one or more amino acid substitutions may be selected from (but are not limited to) V367F, W436R, and/or N354D/D364Y or other amino acid substitutes consisting of new coronavirus variants of concern (VOC) having higher affinity for the target receptor (table 1). To be used against contracting the COVID-19 disease and to release and shorten the disease progression and duration.

The following represent non-limiting embodiments of the present technology. The following is a non-exclusive list of embodiments, and as such, should not be seen to limit, in any way, the various inventions disclosed herein.

1. A method of preventing or reducing pathogen binding to target areas of cell surfaces of a host selected from mammals, comprising providing administering to the mammal a carrier comprising biocompatible particles having a maximum size in at least one dimension in the nanometer or micrometer range, forming a core, and further having a functionalized surface capable of binding to said target areas of said cell surfaces to at least temporarily block said target areas to prevent or minimize pathogen binding and thus, reducing the risk of the host contracting a disease caused by said pathogen.

2. The method according to embodiment 1, wherein the carrier has the capacity of binding and encapsulating the pathogen, thus immobilizing the pathogens ability to bind and entry to the host lowering the risk of contracting the specific infectious agent.

3. The method according to embodiment 1 or 2, wherein the core structure of the carrier is being obtained by 3D printing, microfluidics, sol-gel method or other bottom-up and/or top-down method of fabrication.

4. The method according to any of embodiments 1 to 3, wherein the core material comprises organic or inorganic components, lipid droplets, amino acids, proteins, salts and minerals or other molecules or wherein the core material comprises mesoporous silica nanoparticles, in particular mesoporous silica particles with ordered mesostructures of pores that preferably are capable of being loaded with drugs.

5. The method according to any of embodiments 1 to 4, wherein the core material is functionalized with substance selected from the group consisting of peptides, proteins such as antibodies, chemical agents, active pharmaceutical ingredients (API), organic or inorganic polymers or molecules and combinations thereof.

6. The method according to any of embodiments 1 to 5, wherein the carrier functionalized for specifically binding to receptors, proteins and macromolecules at the cellular level in order to prevent and minimize pathogen entry to the host target tissues by competitive inhibition.

7. The method according to any of embodiments 1 to 6, wherein the synthetic nanoparticle and/or microparticle is used for reducing the spread of SARS-CoV-2 virus or other viruses that causes a respiratory infection, diarrhea, common cold, influenzas or generally discomfort or a combination thereof.

8. The method according to any of embodiments 1 to 7, wherein said synthetic nanoparticle has a 3D-configuration generally matching the characteristics of the SARS-CoV-2 virus or other viruses that causes a respiratory infection, diarrhea, common cold, influenzas or generally discomfort or a combination thereof, in particular the particle is fabricated to a size of around 100 nm and coated with similar amino acids as the glycoprotein spikes or protruding proteins at the surface of the viral particle or similar molecules that mimic the surface of the viral envelope.

9. The method according to any of embodiments 1 to 8, wherein said synthetic nanoparticle resembles the SARS-CoV-2 virus, influenza viruses, rhinoviruses, common cold viruses and/or noroviruses or is optimized for competitive inhibition.

10. The method according to any of embodiments 1 to 9, wherein the synthetic carrier exhibits a modified particle morphology, size or surface properties to achieve increased affinity for the target receptor angiotensin converting enzyme 2 (ACE-2), compared with the SARS-CoV-2 virus, and/or other viruses that causes a respiratory infection, diarrhea, common cold, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

11. The method according to any of embodiments 1 to 10, wherein said synthetic nanoparticle resembling the SARS-CoV-2 virus, influenza viruses, rhinoviruses, common cold viruses and/or noroviruses is adapted for personalized medicine.

12. The method according to any of embodiments 1 to 11, wherein said the synthetic nanoparticle resembling the SARS-CoV-2 virus, influenza viruses, rhinoviruses, common cold viruses and/or noroviruses is loaded into or onto the nanoparticle for further enhancing the anti-viral properties.

13. The method according to any of embodiments 1 to 12, wherein said synthetic nanoparticle resembling the SARS-CoV-2 virus, influenza viruses, rhinoviruses, common cold viruses and/or noroviruses is loaded with vehicles or proteome inhibitors for efficiently delivering the compounds in the target tissues with minimal off-target effects.

14. The method according to any of embodiments 1 to 13, wherein the synthetic nanoparticle is decorated with molecules that have high affinity towards the SARS-CoV-2 virus or any other pathogen of interest such as influenza viruses, rhinoviruses, common cold viruses and/or noroviruses in order to bind and immobilize the infectious agent preventing or minimizing the potential risk of host entry.

15. The method according to any of embodiments 1 to 14, wherein the synthetic nanoparticle resembling the SARS-CoV-2 virus or any other pathogen such as influenza viruses, rhinoviruses, common cold viruses and/or noroviruses is coated or decorated with epitopes to be used as a vaccination at target cell populations.

16. The method according to any of embodiments 1 to 15, wherein the carrier is loaded, stored or dispersed in a device or vessel capable of on-demand release of the carrier to the end-user.

17. The method according to any of embodiments 1 to 16, wherein the carrier system is loaded inside a dispenser such as an inhalation device, tablet, injectable substance, cream or ointment.

18. The method according to any of embodiments 1 to 17, wherein the man-made materials is used for immobilizing specific pathogens by adding the synthetic material in sanitation products and disinfectants.

19. The method according to any of embodiments 1 to 18 for preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

The following embodiments are disclosed. The following is a non-exclusive list of embodiments, and as such, should not be seen to limit, in any way, the various inventions disclosed herein.

1. A synthetic carrier for use in a method of preventing or reducing pathogen binding to target areas of cell surfaces of a host, said carrier comprising biocompatible particles having a maximum size which, in at least one dimension, is in the nanometer or micrometer range, forming a core, and further having a functionalized surface capable of binding to said target areas of said cell surfaces so as to at least temporarily block said target areas to prevent or minimize pathogen binding and, thus, reducing the risk of the host contracting a disease caused by said pathogen.

2. The synthetic carrier for use in a method of preventing or reducing pathogen binding to target areas of cell structures of a host according to embodiment 1, said carrier having the capacity of binding and encapsulating the pathogen, thus immobilizing the pathogens ability to bind and entry to the host lowering the risk of contracting the specific infectious agent.

3. The synthetic carrier for use in a method of preventing or reducing pathogen binding to target areas of cell structures of a host according to embodiment 1 or 2, wherein said core structure of the carrier is being obtained by 3D printing, microfluidics, sol-gel method or other bottom-up and/or top-down method of fabrication.

4. The synthetic carrier for use in a method of preventing or reducing pathogen binding to target areas of cell structures of a host according to any one of embodiments 1 to 3, wherein the core material comprises organic or inorganic components, lipid droplets, amino acids, proteins, salts and minerals or other molecules.

5. The synthetic carrier for use in a method of preventing or reducing pathogen binding to target areas of cell structures of a host according to any one of the preceding embodiments, wherein the core material comprises inorganic silica nanoparticles, in particular mesoporous silica particles, such particles preferably having ordered mesostructures of pores that preferably are capable of being loaded with drugs.

6. The synthetic carrier for use in a method of preventing or reducing pathogen binding to target areas of cell structures of a host according to any one of the preceding embodiments, wherein said core material is functionalized with substance selected from the group consisting of peptides, proteins such as antibodies, chemical agents, active pharmaceutical ingredients (API), organic or inorganic polymers or molecules and combinations thereof.

7. The synthetic carrier for use in a method of preventing or reducing pathogen binding to target areas of cell structures of a host according to any one of the preceding embodiments, wherein said the carrier with its functionalization is used for specifically binding to receptors, proteins and macromolecules at the cellular level in order to prevent and minimize pathogen entry to the host target tissues by competitive inhibition.

8. The synthetic carrier for use in a method of preventing or reducing pathogen binding to target areas of cell structures of a host according to any one of the preceding embodiments, said method comprising loading drugs, API, molecules, peptides inside or onto the carrier system.

9. The synthetic carrier for use in a method of preventing or reducing pathogen binding to target areas of cell structures of a host according to any one of the preceding embodiments, comprising a functionalized and drug loaded carrier, said carrier being used for targeted drug delivery of anti-pathogenic, anti-viral or anti-microbial compounds in order to decrease the growth of the pathogen, such as infectious agent.

10. The synthetic carrier for use in a method of preventing or reducing pathogen binding to target areas of cell structures of a host according to any one of the preceding embodiments, wherein said synthetic nanoparticle and/or microparticle is used for reducing the spread of SARS-CoV-2 virus or other viruses that causes a respiratory infection, diarrhea, common cold, influenzas or generally discomfort or a combination thereof.

11. The synthetic carrier for use in a method of preventing or reducing pathogen binding to target areas of cell structures of a host according to any one of the preceding embodiments, wherein said synthetic nanoparticle has a 3D-configuration generally matching the characteristics of the SARS-CoV-2 virus or influenza viruses, rhinoviruses, common cold viruses and/or noroviruses, in particular the particle is fabricated to a size of around 100 nm and coated with similar amino acids as the glycoprotein spikes or other protruding proteins at the surface of the viral particle or similar molecules that mimic the surface of the viral envelope and thus binds to the same target receptor as the virus.

12. The synthetic carrier for use in a method of preventing or reducing pathogen binding to target areas of cell structures of a host according to any one of the preceding embodiments, wherein said synthetic nanoparticle resembles the SARS-CoV-2 virus or influenza viruses, rhinoviruses, common cold viruses and/or noroviruses or is optimized for competitive inhibition.

13. The synthetic carrier for use in a method of preventing or reducing pathogen binding to target areas of cell structures of a host according to embodiment 12, wherein the synthetic carrier exhibits a modified particle morphology, size or surface properties to achieve increased affinity for the target receptor angiotensin converting enzyme 2 (ACE-2) compared with the SARS-CoV-2 virus or influenza viruses, rhinoviruses, common cold viruses and/or noroviruses, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

14. The synthetic carrier for use in a method of preventing or reducing pathogen binding to target areas of cell structures of a host according to any one of the preceding embodiments, wherein said synthetic nanoparticle resembling the SARS-CoV-2 virus, or influenza viruses, rhinoviruses, common cold viruses and/or noroviruses is adapted for personalized medicine.

15. The synthetic carrier for use in a method of preventing or reducing pathogen binding to target areas of cell structures of a host according to any one of the preceding embodiments, wherein said the synthetic nanoparticle resembling the SARS-CoV-2 virus or influenza viruses, rhinoviruses, common cold viruses and/or noroviruses is loaded into or onto the nanoparticle for further enhancing the anti-viral properties.

16. The synthetic carrier for use in a method of preventing or reducing pathogen binding to target areas of cell structures of a host according to any one of the preceding embodiments, wherein said synthetic nanoparticle resembling the SARS-CoV-2 virus, or influenza viruses, rhinoviruses, common cold viruses and/or noroviruses is loaded with vehicles or proteome inhibitors for efficiently delivering the compounds in the target tissues with minimal off-target effects.

17. The synthetic carrier for use in a method of preventing or reducing pathogen binding to target areas of cell structures of a host according to any one of the preceding embodiments, wherein said synthetic nanoparticle is decorated with molecules that have high affinity towards the SARS-CoV-2 virus or any other pathogen of interest for example influenza viruses, rhinoviruses, common cold viruses and/or noroviruses in order to bind and immobilize the infectious agent preventing or minimizing the potential risk of host entry.

18. The synthetic carrier for use in a method of preventing or reducing pathogen binding to target areas of cell structures of a host according to any one of the preceding embodiments, wherein said synthetic nanoparticle resembling the SARS-CoV-2 virus or any other pathogen for example or influenza viruses, rhinoviruses, common cold viruses and/or noroviruses is coated or decorated with epitopes to be used as a vaccination at target cell populations making the administration potentially easier for the end user e.g. inhalation compared to intra muscular injection used in traditional vaccinations.

19. The synthetic carrier for use in a method of preventing or reducing pathogen binding to target areas of cell structures of a host according to any one of the preceding embodiments, wherein said carrier is loaded, stored or dispersed in a device or vessel capable of on-demand release of the carrier to the end-user.

20. The synthetic carrier for use in a method of preventing or reducing pathogen binding to target areas of cell structures of a host according to any one of the preceding embodiments, wherein said carrier system is loaded inside a dispenser such as an inhalation device, tablet, injectable substance, cream or ointment.

21. The synthetic carrier for use in a method of preventing or reducing pathogen binding to target areas of cell structures of a host according to any one of the preceding embodiments, wherein said the man-made materials is used for immobilizing specific pathogens by adding the synthetic material in sanitation products and disinfectants.

22. The synthetic carrier for use in a method of preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

23. Method of producing a synthetic carrier according to any of embodiments 1 to 22, comprising the steps of a) providing a core material, e.g. a nano- and/or micromaterial including nanoparticles, microparticles or any other object as disclosed herein;

b) coating or functionalizing the core material with molecules, polymers, amino acids, proteins, API, drugs or other material as disclosed herein;

c) loading the object with compounds, molecules, drugs, API, DNA or RNA etc.;

d) coating a second protective and/or functional layer on top of the object in particular for increasing its resistance that could be important in extreme environments such as the acidic environment in the stomach; and providing a small device, medical device, inhalation device or aerosol, sanitation product or consumer product that on-demand will release the containing synthetic material, particle or object for administration.

The following embodiments are non-limiting representative configurations of the present technology. The following is a non-exclusive list of embodiments, and as such, should not be seen to limit, in any way, the various inventions disclosed herein.

1. A method of preventing or reducing pathogen binding, in particular of preventing or reducing binding of SARS-CoV-2 or influenza viruses, rhinoviruses, common cold viruses and/or noroviruses and viral strains thereof, to target areas of cell surfaces of a host selected from mammals, comprising providing administering to the mammal a carrier comprising biocompatible particles having a maximum size in at least one dimension in the nanometer or micrometer range, forming a core, and further having a functionalized surface capable of binding to said target areas of said cell surfaces to at least temporarily block said target areas to prevent or minimize pathogen binding and thus, reducing the risk of the host contracting a disease caused by said pathogen.

2. The method according to embodiment 1, wherein the carrier has the capacity of binding and encapsulating the pathogen, thus immobilizing the pathogens ability to bind and entry to the host lowering the risk of contracting the specific infectious agent.

3. The method according to embodiment 1 or 2, wherein the carrier has the capacity of binding and encapsulating the pathogen thus immobilizing the pathogens ability to bind and enter the host and capable of binding to said target areas of said cell surfaces to at least temporarily block viral entry, thus having dual targeting strategies thus significantly hinder the pathogens ability to bind and entry to the host lowering the risk of contracting the specific infectious agent.

4. The method according to embodiment 1 to 3, wherein the core structure of the carrier is being obtained by 3D printing, microfluidics, sol-gel method or other bottom-up and/or top-down method of fabrication.

5. The method according to any of embodiments 1 to 4, wherein the core material comprises organic or inorganic components, lipid droplets, amino acids, proteins, salts and minerals or other molecules or wherein the core material comprises mesoporous silica nanoparticles, in particular mesoporous silica particles with ordered mesostructures of pores that preferably are capable of being loaded with drugs.

6. The method according to any of embodiments 1 to 5, wherein the core material is functionalized with substance selected from the group consisting of peptides, proteins such as antibodies, chemical agents, active pharmaceutical ingredients (API), organic or inorganic polymers or molecules and combinations thereof.

7. The method according to any of embodiments 1 to 6, wherein the carrier functionalized for specifically binding to receptors, proteins and macromolecules at the cellular level in order to prevent and minimize pathogen entry to the host target tissues by competitive inhibition.

8. The method according to any of embodiments 1 to 7, wherein the synthetic nanoparticle and/or microparticle is used for reducing the spread of SARS-CoV-2 virus or other viruses that causes a respiratory infection, diarrhea, common cold, influenzas or generally discomfort or a combination thereof.

9. The method according to any of embodiments 1 to 8, wherein said synthetic nanoparticle has a 3D-configuration generally matching the characteristics of the SARS-CoV-2 virus or other viruses that causes a respiratory infection, diarrhea, common cold, influenzas or generally discomfort or a combination thereof, in particular the particle is fabricated to a size of around 100 nm and coated with similar amino acids as the glycoprotein spikes at the surface of the viral particle or similar molecules that mimic the surface of the viral envelope.

10. The method according to any of embodiments 1 to 9, wherein said synthetic nanoparticle resembles the SARS-CoV-2 virus or other viruses that causes a respiratory infection, diarrhea, common cold, influenzas or generally discomfort or a combination thereof, or is optimized for competitive inhibition.

11. The method according to any of embodiments 1 to 10, wherein the synthetic carrier exhibits a modified particle morphology, size or surface properties to achieve increased affinity for the target receptor angiotensin converting enzyme 2 (ACE2) compared with the SARS-CoV-2 virus or other viruses that causes a respiratory infection, diarrhea, common cold, influenzas or generally discomfort or a combination thereof, in particular for increasing the binding affinity for the specific receptor e.g., silicid sialic acid, histo-blood group antigens, ICAM-1, IGF1R blocking the internalization of the viral envelope more efficiently and potentially prolonging the gained viral protection.

12. The method according to any of embodiments 1 to 11, wherein said synthetic nanoparticle resembling the SARS-CoV-2 virus or other viruses that causes a respiratory infection, diarrhea, common cold, influenzas or generally discomfort or a combination thereof. is adapted for personalized medicine.

13. The method according to any of embodiments 1 to 12, wherein said the synthetic nanoparticle resembling the SARS-CoV-2 virus or other viruses that causes a respiratory infection, diarrhea, common cold, influenzas or generally discomfort or a combination thereof. is loaded into or onto the nanoparticle for further enhancing the anti-viral properties.

14. The method according to any of embodiments 1 to 13, wherein said synthetic nanoparticle resembling the SARS-CoV-2 virus or other viruses that causes a respiratory infection, diarrhea, common cold, influenzas or generally discomfort or a combination thereof. is loaded with vehicles or proteome inhibitors for efficiently delivering the compounds in the target tissues with minimal off-target effects.

15. The method according to any of embodiments 1 to 14, wherein the synthetic nanoparticle is decorated with molecules that have high affinity towards the SARS-CoV-2 virus or any other pathogen of interest for example influenzas, rhinoviruses and viruses causing respiratory infection in order to bind and immobilize the infectious agent preventing or minimizing the potential risk of host entry.

16. The method according to any of embodiments 1 to 15, wherein the synthetic nanoparticle resembling the SARS-CoV-2 virus or any other pathogen for example influenzas, rhinoviruses and viruses causing respiratory infection is coated or decorated with epitopes to be used as a vaccination at target cell populations.

17. The method according to any of embodiments 1 to 16, wherein the carrier is loaded, stored or dispersed in a device or vessel capable of on-demand release of the carrier to the end-user.

18. The method according to any of embodiments 1 to 17, wherein the carrier system is loaded inside a dispenser such as an inhalation device, tablet, injectable substance, cream or ointment.

19. The method according to any of embodiments 1 to 18, wherein the man-made materials is used for immobilizing specific pathogens by adding the synthetic material in sanitation products and disinfectants.

20. The method according to any of embodiments 1 to 19 for preventing or reducing pathogen binding to target areas of cell structures of a host according to any one of the preceding embodiments, wherein said method comprises minimizing the spread of diverse pathogens by binding to the target molecule in the hos body or binding to the infectious agent itself and potently inhibit the spread of the disease.

The following embodiments are disclosed. The following is a non-exclusive list of embodiments, and as such, should not be seen to limit, in any way, the various inventions disclosed herein.

1. A synthetic carrier for use in a method of preventing or reducing binding of a pathogen to target areas of cell structures of a host, said carrier comprising biocompatible particles having a maximum size in at least one dimension in the nanometer or micrometer range, forming a core, and further having a functionalized surface, which preferably mimics that of the pathogen capable of binding to said target areas of said cell surfaces to at least temporarily block said target areas to prevent or minimize pathogen binding and thus, reducing the risk of the host contracting a disease caused by said pathogen.

2. The synthetic carrier for use in a method of preventing or reducing pathogen binding to target areas of cell structures of a host according to embodiment 1, wherein the pathogen is a coronavirus, in particular SARS-CoV-2 or viral strains derived thereof.

3. The synthetic carrier for use in a method of preventing or reducing pathogen binding to target areas of cell structures of a host according to embodiment 1, wherein the cell structures are selected from ACE2 and TMPRSS2 receptors and combinations thereof.

4. The synthetic carrier for use in a method of preventing or reducing pathogen binding to target areas of cell structures of a host according to embodiment 1 or 2, said carrier having the capacity of binding and encapsulating the pathogens co-receptors e.g., high-density lipoprotein (HDL) scavenger receptor B type 1 (SR-B1), thus immobilizing the pathogens ability to bind and entry to the host lowering the risk of contracting the specific infectious agent.

5. The synthetic carrier for use in a method of preventing or reducing pathogen coronaviruses, such as SARS-CoV-2, binding to target areas of cell structures of a host according to any of embodiments 1 to 3, wherein said core structure of the carrier is being obtained by 3D printing, microfluidics, sol-gel method or other bottom-up and/or top-down method of fabrication, and wherein the core material comprises organic or inorganic components, lipid droplets, amino acids, proteins, salts and minerals or other molecules.

6. The synthetic carrier for use in a method of preventing or reducing pathogen, in particular coronaviruses binding to target areas of cell structures of a host according to any one of the preceding embodiments, wherein the core material comprises inorganic silica nanoparticles, in particular mesoporous silica particles, such particles preferably having ordered mesostructures of pores that preferably are capable of being loaded with drugs.

7. The synthetic carrier for use in a method of preventing or reducing coronaviruses binding to target areas of cell structures of a host according to any one of the preceding embodiments, wherein said core material is functionalized with substance selected from the group consisting of peptides, proteins such as antibodies, chemical agents, active pharmaceutical ingredients (API), organic or inorganic polymers or molecules and combinations thereof, and wherein said carrier with its functionalization is preferably used for specifically binding to receptors, proteins and macromolecules at the cellular level in order to prevent and minimize novel coronaviruses such as SARS-CoV-2 entry to the host target cells by competitive inhibition.

8. The synthetic carrier for use in a method of preventing or reducing coronaviruses binding to target areas of cell structures of a host according to any one of the preceding embodiments, said method comprising loading drugs, API, molecules, peptides inside or onto the carrier system, wherein the carrier preferably comprises a functionalized and drug loaded carrier, said carrier being used for targeted drug delivery of anti-viral in order to decrease the replication of the virus inside the host cell.

9. The synthetic carrier for use in a method of preventing or reducing coronaviruses binding to target areas of cell structures of a host according to any one of the preceding embodiments, wherein said synthetic nanoparticle and/or microparticle is used for reducing the spread of SARS-CoV-2 or other coronaviruses strains and/or types derived from the SARS-CoV-2 that causes a respiratory infection, diarrhea, common cold, cytokine storm, death or generally discomfort or a combination thereof.

10. The synthetic carrier for use in a method of preventing or reducing coronaviruses binding to target areas of cell structures of a host according to any one of the preceding embodiments, wherein said synthetic nanoparticle has a 3D-configuration generally matching the characteristics of the SARS-CoV-2 virus or future variants thereof, in particular the particle is fabricated to a size of around 100-120 nm and coated with similar amino acids as the glycoprotein spikes at the surface of the viral particle or similar molecules that mimic the surface of the viral envelope e.g. spike protein and thus binds to the same target receptor as the virus.

11. The synthetic carrier for use in a method of preventing or reducing coronaviruses binding to target areas of cell structures of a host according to any one of the preceding embodiments, wherein said synthetic nanoparticle resembles the SARS-CoV-2 virus or is optimized for competitive inhibition, wherein preferably the synthetic carrier exhibits a modified particle morphology, size or surface properties to achieve increased affinity for the target receptor ACE2 and/or TMPRSS2, compared with the SARS-CoV-2 virus, in particular for increasing the binding affinity for the specific receptor blocking the internalization of the viral envelope more efficiently and potentially prolonging the gained viral protection.

12. The synthetic carrier for use in a method of preventing or reducing coronaviruses binding to target areas of cell structures of a host according to any one of the preceding embodiments, wherein said synthetic nanoparticle resembling the SARS-CoV-2 virus is adapted for personalized medicine.

13. The synthetic carrier for use in a method of preventing or reducing coronavirus binding to target areas of cell structures of a host according to any one of the preceding embodiments, wherein said synthetic nanoparticle resembling the SARS-CoV-2 virus is adapted for personalized medicine in the case of ACE2 receptor polymorphism or different animal host organisms for achieving receptor interaction.

14. The synthetic carrier for use in a method of preventing or reducing coronaviruses binding to target areas of cell structures of a host according to any one of the preceding embodiments, wherein said synthetic nanoparticle resembling the SARS-CoV-2 virus is loaded into or onto the nanoparticle for further enhancing the anti-viral properties, or wherein said synthetic nanoparticle resembling the SARS-CoV-2 virus is loaded with vehicles or proteome inhibitors for efficiently delivering the compounds in the target cell and tissues with minimal off-target effects.

15. The synthetic carrier for use in a method of preventing or reducing coronaviruses binding to target areas of cell structures of a host according to any one of the preceding embodiments, wherein said carrier is loaded, stored or dispersed in a device or vessel capable of on-demand release of the carrier to the end-user, wherein said carrier system is preferably loaded inside a dispenser such as an inhalation device, tablet, injectable substance, cream or ointment.

16. The synthetic carrier for use in a method of preventing or reducing coronaviruses binding to target areas of cell structures of a host according to any one of the preceding embodiments, wherein said synthetic nanoparticle is a self-assembling recombinant protein-based nanoparticle construct, such as a SpyTag/SpyCatcher system 17. Method of producing a synthetic carrier according to any of embodiments 1 to 16, comprising the steps of a) providing a core material, e.g. a nano- and/or micromaterial including nanoparticles, microparticles or any other object as disclosed herein;

b) coating or functionalizing the core material with molecules, polymers, amino acids, proteins, API, drugs or other material as disclosed herein;

c) loading the object with compounds, molecules, drugs, API, DNA or RNA etc.;

d) coating a second protective and/or functional layer on top of the object in particular for increasing its resistance that could be important in extreme environments such as the acidic environment in the stomach; and providing a small device, medical device, inhalation device or aerosol, sanitation product or consumer product that on-demand will release the containing synthetic material, particle or object for administration.

It will be obvious to a person skilled in the art that, as the technology advances, the inventive concept can be implemented in various ways. The invention and its embodiments are not limited to the examples described above but may vary within the scope of the claims.

REFERENCES

1. Szymanski C M, Schnaar R L, Aebi M. Bacterial and Viral Infections. 2017. In: Varki A, Cummings R D, Esko J D, et al., editors. Essentials of Glycobiology [Internet]. 3rd edition. Cold Spring Harbor (N.Y.): Cold Spring Harbor Laboratory Press; 2015-2017. Chapter 42. Available from: https://www.ncbi.nlm.nih.gov/books/NBK453060/

2. Thakur V, Asad M, Jain S, Hossain M E, Gupta A, Kaur I, Rathore S, Ali S, Khan N J, Mohmmed A. Eps15 homology domain containing protein of *Plasmodium falciparum* (PfEHD) associates with endocytosis and vesicular trafficking towards neutral lipid storage site. Biochim Biophys Acta. 2015 November; 1853(11 Pt A):2856-69. doi: 10.1016/j.bbamcr.2015.08.007.

3. Lin Li, Ting Sun, Yufei He, Wendong Li, Yubo Fan, Jing Zhang. Epitope-based peptide vaccines predicted against novel coronavirus disease caused by SARS-CoV-2. bioRxiv 2020.02.25.965434

4. Ahmed S F, Quadeer A A, McKay M R. Preliminary Identification of Potential Vaccine Targets for the COVID-19 Coronavirus (SARS-CoV-2) Based on SARS-CoV Immunological Studies. Viruses. 2020 Feb. 25; 12(3).

5. Larry R. Engelking, Chapter 6—Enzyme Kinetics. Editor(s): Larry R. Engelking, Textbook of Veterinary Physiological Chemistry (Third Edition). Academic Press, 2015, Pages 32-38, ISBN 9780123919090.

6. Shang J, Ye G, Shi K, Wan Y, Luo C, Aihara H, Geng Q, Auerbach A, Li F. Structural basis of receptor recognition by SARS-CoV-2. Nature. 2020 May; 581(7807):221-224. doi: 10.1038/s41586-020-2179-y. Epub 2020 Mar. 30. PMID: 32225175; PMCID: PMC7328981.

7. Ranga V, Niemela E, Tamirat M Z, Eriksson J E, Airenne T T, Johnson M S. Immunogenic SARS-CoV-2 Epitopes: In Silico Study Towards Better Understanding of COVID-19 Disease-Paving the Way for Vaccine Development. Vaccines (Basel). 2020 Jul. 23; 8(3):408. doi: 10.3390/vaccines8030408. PMID: 32717854; PMCID: PMC7564651.

8. Peter E K, Schug A. The Inhibitory Effect of a Coronavirus Spike Protein Fragment with ACE2. Biophys J. 2020 Aug. 27:S0006-3495(20)30670-6. doi: 10.1016/j.bpj.2020.08.022. Epub ahead of print. PMID: 32941783; PMCID: PMC7451127.

9. Devaux C A, Rolain J M, Raoult D. ACE2 receptor polymorphism: Susceptibility to SARS-CoV-2, hypertension, multi-organ failure, and COVID-19 disease outcome. J Microbiol Immunol Infect. 2020 June; 53(3):425-435. doi: 10.1016/j.jmii.2020.04.015. Epub 2020 May 6. PMID: 32414646; PMCID: PMC7201239.

10. Lam S D, Bordin N, Waman V P, Scholes H M, Ashford P, Sen N, van Dorp L, Rauer C, Dawson N L, Pang C S M, Abbasian M, Sillitoe I, Edwards S J L, Fraternali F, Lees J G, Santini J M, Orengo C A. SARS-CoV-2 spike protein predicted to form complexes with host receptor protein orthologues from a broad range of mammals. Sci Rep. 2020 Oct. 5; 10(1):16471. doi: 10.1038/s41598-020-71936-5. PMID: 33020502; PMCID: PMC7536205.

11. Alan R. Shaw, Mark B. Feinberg, 90—Vaccines, Editor(s): Robert R. Rich, Thomas A. Fleisher, William T. Shearer, Harry W. Schroeder, Anthony J. Frew, Cornelia M. Weyand, Clinical Immunology (Fourth Edition), 2013, Pages 1095-1121, ISBN 9780723436911.

12. Clercq E D, Li G, Approved Antiviral Drugs over the Past 50 Years, Clinical Microbiology Reviews June 2016, 29 (3) 695-747; DOI: 10.1128/CMR.00102-15.

13. Dou Q P, Zonder J A. Overview of proteasome inhibitor-based anti-cancer therapies: perspective on bortezomib and second generation proteasome inhibitors versus future generation inhibitors of ubiquitin-proteasome system. Curr Cancer Drug Targets. 2014; 14(6):517-36.

14. Liu J K. The history of monoclonal antibody development—Progress, remaining challenges and future innovations. Ann Med Surg (Lond). 2014 Sep. 11; 3(4):113-6.
15. Niemelä E. Nanoparticles as Targeting System for Cancer Treatment: From idea towards reality. Åbo Akademi Univeristy. Painosalama. ISBN:978-952-12-3855-0.
16. Flora G, Mittal M, Flora S J S, 26—Medical Countermeasures—Chelation Therapy, Editor(s): Flora S J S, Handbook of Arsenic Toxicology, Academic Press, 2015, Pages 589-626, ISBN 9780124186880.
17. Wei C, Wan L, Yan Q, Wang X, Zhang J, Yang X, Zhang Y, Fan C, Li D, Deng Y, Sun J, Gong J, Yang X, Wang Y, Wang X, Li J, Yang H, Li H, Zhang Z, Wang R, Du P, Zong Y, Yin F, Zhang W, Wang N, Peng Y, Lin H, Feng J, Qin C, Chen W, Gao Q, Zhang R, Cao Y, Zhong H. HDL-scavenger receptor B type 1 facilitates SARS-CoV-2 entry. Nat Metab. 2020 Nov. 26. doi: 10.1038/s42255-020-00324-0. Epub ahead of print. PMID: 33244168.
18. Caruso F, Singh M, Belli S, Berinato M, Rossi M. Interrelated Mechanism by Which the Methide Quinone Celastrol, Obtained from the Roots of *Tripterygium wilfordii*, Inhibits Main Protease 3CLpro of COVID-19 and Acts as Superoxide Radical Scavenger. Int J Mol Sci. 2020 Dec. 4; 21(23):9266. doi: 10.3390/ijms21239266. PMID: 33291769; PMCID: PMC7731079.
19. The Williams dictionary of Biomaterials, Williams D F, 1999, ISBN 0-85323-921-5
20. Sun Y, Guo F, Zou Z, et al. Cationic nanoparticles directly bind angiotensin-converting enzyme 2 and induce acute lung injury in mice. Part Fibre Toxicol. 2015; 12:4. Published 2015 Mar. 7.
21. te Velthuis A J, van den Worm S H, Sims A C, Baric R S, Snijder E J, van Hemert M J. Zn(2+) inhibits coronavirus and arterivirus RNA polymerase activity in vitro and zinc ionophores block the replication of these viruses in cell culture. PLoS Pathog. 2010 Nov. 4; 6(11):e1001176.
22. Shaffer L. 15 drugs being tested to treat COVID-19 and how they would work. Nature Medicine. doi: 10.1038/d41591-020-00019-9
23. Bruun T U J, Andersson A C, Draper S J, Howarth M. Engineering a Rugged Nanoscaffold to Enhance Plug-and-Display Vaccination. ACS Nano. 2018 Sep. 25; 12(9):8855-8866. doi: 10.1021/acsnano.8b02805. Epub 2018 Jul. 26. PMID: 30028591; PMCID: PMC6158681.
24. Yin-Feng Kang, Cong Sun, Zhen Zhuang, Run-Yu Yuan, Qing-Bing Zheng, Jiang-Ping Li, Ping-Ping Zhou, Xin-Chun Chen, Xiao Zhang, Xiao-Hui Yu, Xiang-Wei Kong, Qian-Ying Zhu, Miao Xu, Nan-Shan Zhong, Yi-Xin Zeng, Guo-Kai Feng, Chang-Wen Ke, Jin-Cun Zhao, Mu-Sheng Zeng. Rapid development of SARS-CoV-2 receptor binding domain-conjugated nanoparticle vaccine candidate. bioRxiv 2020.11.03.366138; doi: https://doi.org/10.1101/2020.11.03.366138
25. Tan T K, Rijal P, Rahikainen R, Keeble A H, Schimanski L, Hussain S, Harvey R, Hayes J W P, Edwards J C, McLean R K, Martini V, Pedrera M, Thakur N, Conceicao C, Dietrich I, Shelton H, Ludi A, Wilsden G, Browning C, Zagrajek A K, Bialy D, Bhat S, Stevenson-Leggett P, Hollinghurst P, Tully M, Moffat K, Chiu C, Waters R, Gray A, Azhar M, Mioulet V, Newman J, Asfor A S, Burman A, Crossley S, Hammond J A, Tchilian E, Charleston B, Bailey D, Tuthill T J, Graham S P, Duyvesteyn H M E, Malinauskas T, Huo J, Tree J A, Buttigieg K R, Owens R J, Carroll M W, Daniels R S, McCauley J W, Stuart D I, Huang K A, Howarth M, Townsend A R. A COVID-19 vaccine candidate using SpyCatcher multimerization of the SARS-CoV-2 spike protein receptor-binding domain induces potent neutralising antibody responses. Nat Commun. 2021 Jan. 22; 12(1):542. doi: 10.1038/s41467-020-20654-7. PMID: 33483491; PMCID: PMC7822889.
26. Wu F, Zhao S, Yu B, Chen Y M, Wang W, Song Z G, Hu Y, Tao Z W, Tian J H, Pei Y Y, Yuan M L, Zhang Y L, Dai F H, Liu Y, Wang Q M, Zheng J J, Xu L, Holmes E C, Zhang Y Z. A new coronavirus associated with human respiratory disease in China. Nature. 2020 March; 579 (7798):265-269. doi: 10.1038/s41586-020-2008-3. Epub 2020 Feb. 3. Erratum in: Nature. 2020 April; 580(7803): E7. PMID: 32015508; PMCID: PMC7094943.
27. Ou J, Zhou Z, Dai R, Zhao S, Wu X, Zhang J, Lan W, Cui L, Wu J, Seto D, Chodosh J, Zhang G, Zhang Q. V367F mutation in SARS-CoV-2 spike RBD emerging during the early transmission phase enhances viral infectivity through increased human ACE2 receptor binding affinity. bioRxiv 2020.03.15.991844; doi: https://doi.org/10.1101/2020.03.15.991844

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. The methods summarized above and set forth in further detail below describe certain actions taken by a user (e.g., a professional in some instances); however, it should be understood that they can also include the instruction of those actions by another party. Thus, actions such as "delivering" include "instructing delivering." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A carrier for reducing a likelihood of a pathogen binding to cell structures of a cell of a host, the carrier comprising:
a core;
surface features extending from an exterior surface of the core;
wherein the surface features are configured to bind to target areas of cell structures of the host to at least partially block the pathogen from binding to said target areas as a result of competitive inhibition; and
wherein the carrier binding to target areas of cell structures of the cell at least partially inhibits pathogen entry into said cell; and
a plurality of binding sites along the exterior surface, wherein the binding sites are configured to attract at least one portion of the pathogen;
wherein the binding sites are recognizable by the pathogen and are able to be bound by the pathogen, thereby at least partially immobilizing the pathogen and reducing the likelihood of the pathogen binding to target areas of cell structures of the host.

2. The carrier of claim 1, wherein the pathogen comprises a virus.

3. The carrier of claim 2, wherein the virus comprises a SARS-CoV-2 virus.

4. The carrier of claim 2, wherein the virus comprises one or more of the following: a coronavirus, an influenza virus, a rhinovirus, a norovirus, a respiratory syncytial virus (RSV), another virus that impacts the respiratory system and any other type of virus.

5. The carrier of claim 1, wherein the pathogen comprises a bacterium, a parasite, an antigen, a prion, a mold, a fungus or an allergen.

6. The carrier of claim 1, wherein the carrier is sized, shaped or otherwise configured to reach targeted portions of the host that are susceptible to infection by the pathogen.

7. The carrier of claim 6, wherein the targeted portions of the host that are susceptible to infection by the pathogen comprise the lungs or other area of the host's upper or lower respiratory tract.

8. The carrier of claim 7, wherein the carrier is configured to be delivered via the respiratory tract of the host to the targeted portions of the host that are susceptible to infection by the pathogen.

9. The carrier of claim 1, further comprising at least one component positioned at least partially on or within the carrier.

10. The carrier of claim 9, wherein the at least one component comprises an anti-viral compound, a nucleic acid, a RNA or DNA sequence, zinc or an immune stimulating molecule.

11. A carrier for reducing a likelihood of a pathogen binding to cell structures of a cell of a host, the carrier comprising:
a core;
surface features configured to bind to target areas of cell structures of the host to at least partially block the pathogen from binding to said target areas as a result of competitive inhibition, wherein the carrier binding to target areas of cell structures of the cell at least partially inhibits pathogen entry into said cell; and
plurality of binding sites along the exterior surface, wherein the binding sites are configured to attract at least one portion of the pathogen;
wherein the binding sites are recognizable by the pathogen and are able to be bound by the pathogen, thereby at least partially immobilizing the pathogen.

12. The carrier of claim 11, wherein the pathogen comprises a virus.

13. The carrier of claim 12, wherein the virus comprises a SARS-CoV-2 virus.

14. The carrier of claim 12, wherein the virus comprises one or more of the following: a coronavirus, an influenza virus, a rhinovirus, a norovirus, a respiratory syncytial virus (RSV), another virus that impacts the respiratory system and any other type of virus.

15. The carrier of claim 11, wherein the pathogen comprises a bacterium, a parasite, an antigen, a prion, a mold, a fungus or an allergen.

16. The carrier of claim 11, wherein the carrier is sized, shaped or otherwise configured to reach targeted portions of the host that are susceptible to infection by the pathogen.

17. The carrier of claim 16, wherein the targeted portions of the host that are susceptible to infection by the pathogen comprise the lungs or other area of the host's upper or lower respiratory tract.

18. The carrier of claim 17, wherein the carrier is configured to be delivered via the respiratory tract of the host to the targeted portions of the host that are susceptible to infection by the pathogen.

19. The carrier of claim 11, further comprising at least one component positioned at least partially on or within the carrier.

20. The carrier of claim 19, wherein the at least one component comprises an anti-viral compound, a nucleic acid, a RNA or DNA sequence, zinc or an immune stimulating molecule.

* * * * *